United States Patent
Jefson et al.

(10) Patent No.: US 10,421,756 B2
(45) Date of Patent: Sep. 24, 2019

(54) HETEROBICYCLIC N-AMINOPHENYL-AMIDES AS INHIBITORS OF HISTONE DEACETYLASE

(71) Applicant: Rodin Therapeutics, Inc., Boston, MA (US)

(72) Inventors: Martin R. Jefson, Stonington, CT (US); John A. Lowe, III, Stonington, CT (US); Fabian Dey, Basel (CH); Andreas Bergmann, Gauting (DE); Andreas Schoop, Grafrath (DE)

(73) Assignee: Rodin Therapeutics, Inc., Boston, MA (US)

( * ) Notice: Subject to any disclaimer, the term of this patent is extended or adjusted under 35 U.S.C. 154(b) by 0 days.

(21) Appl. No.: 15/741,609

(22) PCT Filed: Jul. 5, 2016

(86) PCT No.: PCT/US2016/040956
§ 371 (c)(1),
(2) Date: Jan. 3, 2018

(87) PCT Pub. No.: WO2017/007755
PCT Pub. Date: Jan. 12, 2017

(65) Prior Publication Data
US 2018/0194760 A1    Jul. 12, 2018

Related U.S. Application Data

(60) Provisional application No. 62/188,854, filed on Jul. 6, 2015.

(51) Int. Cl.
| | | |
|---|---|---|
| *C07D 471/04* | (2006.01) | |
| *C07D 491/08* | (2006.01) | |
| *C07D 471/08* | (2006.01) | |
| *C07D 471/10* | (2006.01) | |
| *C07D 487/04* | (2006.01) | |
| *C07D 487/08* | (2006.01) | |
| *C07D 491/10* | (2006.01) | |
| *C07D 513/04* | (2006.01) | |
| *A61P 25/28* | (2006.01) | |
| *C07D 491/107* | (2006.01) | |

(52) U.S. Cl.
CPC ............ *C07D 471/04* (2013.01); *A61P 25/28* (2018.01); *C07D 471/08* (2013.01); *C07D 471/10* (2013.01); *C07D 487/04* (2013.01); *C07D 487/08* (2013.01); *C07D 491/08* (2013.01); *C07D 491/10* (2013.01); *C07D 491/107* (2013.01); *C07D 513/04* (2013.01)

(58) Field of Classification Search
CPC ................. C07D 471/04; A61P 25/26
USPC ........................................................ 514/256
See application file for complete search history.

(56) References Cited

U.S. PATENT DOCUMENTS

| | | |
|---|---|---|
| 5,112,824 A | 5/1992 | Baldwin et al. |
| 5,872,136 A | 2/1999 | Anthony et al. |
| 7,544,695 B2 | 6/2009 | Berk et al. |
| 7,834,026 B2 | 11/2010 | Berk et al. |
| 7,863,279 B2 | 1/2011 | Even et al. |
| 7,981,874 B2 | 7/2011 | Close et al. |
| 8,349,825 B2 | 1/2013 | Mampreian et al. |
| 8,461,189 B2 | 6/2013 | Heidebrecht, Jr. et al. |
| 8,686,020 B2 | 4/2014 | Hamblett et al. |
| 8,703,959 B2 | 4/2014 | Kutose et al. |
| 8,809,544 B2 | 8/2014 | Kutose et al. |
| 8,962,849 B2 | 2/2015 | Kutose et al. |
| 8,962,850 B2 | 2/2015 | Kutose et al. |
| 8,981,107 B2 | 3/2015 | Kutose et al. |
| 9,951,069 B1 | 4/2018 | Fuller et al. |
| 2002/0183324 A1 | 12/2002 | Jacobson et al. |
| 2003/0187026 A1 | 10/2003 | Li et al. |
| 2003/0199511 A1 | 10/2003 | Li et al. |
| 2005/0025995 A1 | 2/2005 | Cheng et al. |
| 2005/0153981 A1 | 7/2005 | Li et al. |
| 2005/0245530 A1 | 11/2005 | Borzilleri et al. |
| 2006/0173050 A1 | 8/2006 | Liu et al. |
| 2006/0235028 A1 | 10/2006 | Li et al. |
| 2006/0270686 A1 | 11/2006 | Kelly et al. |
| 2007/0004741 A1 | 1/2007 | Apodaca et al. |
| 2007/0037794 A1 | 2/2007 | Ungashe et al. |
| 2007/0135437 A1 | 6/2007 | Benjamin et al. |
| 2008/0064871 A1 | 3/2008 | Hirata et al. |
| 2008/0103182 A1 | 5/2008 | Ackermann et al. |
| 2008/0132503 A1 | 6/2008 | Moradei et al. |
| 2008/0280891 A1 | 11/2008 | Kelly et al. |
| 2009/0022047 A1 | 1/2009 | Seto et al. |
| 2009/0058982 A1 | 3/2009 | Seto et al. |
| 2009/0062297 A1 | 3/2009 | Heidebrecht et al. |
| 2009/0156825 A1 | 6/2009 | Heidebrecht, Jr. et al. |

(Continued)

FOREIGN PATENT DOCUMENTS

| | | |
|---|---|---|
| CN | 103601718 A | 2/2014 |
| CN | 103864754 A | 6/2014 |

(Continued)

OTHER PUBLICATIONS

CAS Registry No. 1072874-82-8. Entered STN: Nov. 14, 2008, 1 page.

(Continued)

*Primary Examiner* — Kahsay Habte
(74) *Attorney, Agent, or Firm* — McCarter & English, LLP; Steven G. Davis; Michael J. DeGrazia

(57) ABSTRACT

This invention provides compounds that are inhibitors of HDAC2. The compounds (e.g., compounds according to Formula (I) or any one of Compounds 100-175) accordingly are useful for treating, alleviating, or preventing a condition in a subject such as a neurological disorder, memory or cognitive function disorder or impairment, extinction learning disorder, fungal disease or infection, inflammatory disease, hematological disease, or neoplastic disease, or for improving memory or treating, alleviating, or preventing memory loss or impairment.

13 Claims, No Drawings

(56) References Cited

U.S. PATENT DOCUMENTS

| | | |
|---|---|---|
| 2009/0207712 A1 | 8/2009 | Seto et al. |
| 2009/0286782 A1 | 11/2009 | Ibrahim et al. |
| 2009/0286783 A1 | 11/2009 | Ibrahim et al. |
| 2009/0306086 A1 | 12/2009 | Ibrahim et al. |
| 2009/0306087 A1 | 12/2009 | Ibrahim et al. |
| 2010/0041670 A1 | 2/2010 | Even et al. |
| 2010/0099676 A1 | 4/2010 | Endoh et al. |
| 2011/0009365 A1 | 1/2011 | Dubois et al. |
| 2011/0021494 A1 | 1/2011 | Maier et al. |
| 2011/0105472 A1 | 5/2011 | Greul et al. |
| 2011/0118248 A1 | 5/2011 | Ungashe et al. |
| 2011/0224155 A1 | 9/2011 | Tachdjian et al. |
| 2012/0184572 A1 | 7/2012 | Song et al. |
| 2012/0295881 A1 | 11/2012 | Lange et al. |
| 2013/0210880 A1 | 8/2013 | Amberg et al. |
| 2013/0331382 A1 | 12/2013 | Hubbard et al. |
| 2014/0128391 A1 | 5/2014 | van Duzer et al. |
| 2014/0187780 A1 | 7/2014 | Kim et al. |
| 2014/0329684 A1 | 11/2014 | Muller et al. |
| 2014/0364605 A1 | 12/2014 | Li et al. |
| 2015/0057300 A1 | 2/2015 | Tafesse et al. |
| 2015/0094329 A1 | 4/2015 | Nokura et al. |
| 2015/0266866 A1 | 9/2015 | Conn et al. |
| 2015/0322076 A1 | 11/2015 | Chen et al. |
| 2016/0096833 A1 | 4/2016 | Emmitte et al. |
| 2018/0009818 A1 | 1/2018 | Miyazaki et al. |
| 2018/0194769 A1 | 7/2018 | Jefson et al. |
| 2018/0215759 A1 | 8/2018 | Fuller et al. |

FOREIGN PATENT DOCUMENTS

| | | | |
|---|---|---|---|
| CN | 105777632 | A | 7/2016 |
| CN | 106946890 | A | 7/2017 |
| DE | 4212748 | A1 | 10/1993 |
| EP | 2712655 | A1 | 4/2014 |
| GB | 2515785 | A | 1/2015 |
| GB | 2516303 | A | 1/2015 |
| JP | H11049676 | A | 2/1999 |
| JP | H11209366 | A | 8/1999 |
| JP | 2003-192673 | A | 7/2003 |
| JP | 2003-300940 | A | 10/2003 |
| JP | 2008-179067 | A | 8/2008 |
| JP | 2008-179068 | A | 8/2008 |
| JP | 2009-023986 | A | 2/2009 |
| JP | 2009-209090 | A | 9/2009 |
| JP | 2012-107001 | A | 6/2012 |
| JP | 2013-020223 | A | 1/2013 |
| JP | 6-208961 | B2 | 6/2013 |
| JP | 2014-101353 | A | 6/2014 |
| WO | 1992/01675 | A2 | 2/1992 |
| WO | 1996/11929 | A1 | 4/1996 |
| WO | 1996/11930 | A1 | 4/1996 |
| WO | 1996/18617 | A1 | 6/1996 |
| WO | 1996/21660 | A1 | 7/1996 |
| WO | 1996/23783 | A1 | 8/1996 |
| WO | 1996/32938 | A1 | 10/1996 |
| WO | 1997/08167 | A1 | 3/1997 |
| WO | 1997/15557 | A1 | 5/1997 |
| WO | 1997/36901 | A1 | 10/1997 |
| WO | 1998/55472 | A1 | 12/1998 |
| WO | 1999/65897 | A1 | 12/1999 |
| WO | 2000/002860 | A1 | 1/2000 |
| WO | 2000/055114 | A1 | 9/2000 |
| WO | 2001/021597 | A1 | 3/2001 |
| WO | 2002/014315 | A2 | 2/2002 |
| WO | 2002/020011 | A2 | 3/2002 |
| WO | 2002/026708 | A1 | 4/2002 |
| WO | 2002/032900 | A2 | 4/2002 |
| WO | 2002/046172 | A2 | 6/2002 |
| WO | 2002/053160 | A1 | 7/2002 |
| WO | 2002/068417 | A2 | 9/2002 |
| WO | 2002/089738 | A2 | 11/2002 |
| WO | 2003/042190 | A1 | 5/2003 |
| WO | 2003/051366 | A2 | 6/2003 |
| WO | 2003/055447 | A2 | 7/2003 |
| WO | 2003/059269 | A2 | 7/2003 |
| WO | 2003/062224 | A1 | 7/2003 |
| WO | 2003/095437 | A1 | 11/2003 |
| WO | 2004/000318 | A2 | 12/2003 |
| WO | 2004/000820 | A2 | 12/2003 |
| WO | 2004/016597 | A2 | 2/2004 |
| WO | 2004/045518 | A2 | 6/2004 |
| WO | 2004/071426 | A2 | 8/2004 |
| WO | 2004/072033 | A2 | 8/2004 |
| WO | 2005/009988 | A1 | 2/2005 |
| WO | 2005/014580 | A1 | 2/2005 |
| WO | 2005/016862 | A1 | 2/2005 |
| WO | 2005/079802 | A1 | 9/2005 |
| WO | 2005/095386 | A1 | 10/2005 |
| WO | 2005/097740 | A1 | 10/2005 |
| WO | 2005/121093 | A1 | 12/2005 |
| WO | 2006/019833 | A1 | 2/2006 |
| WO | 2006/044975 | A2 | 4/2006 |
| WO | 2006/051311 | A1 | 5/2006 |
| WO | 2006/065479 | A2 | 6/2006 |
| WO | 2006/067445 | A2 | 6/2006 |
| WO | 2006/067446 | A1 | 6/2006 |
| WO | 2006/076644 | A2 | 7/2006 |
| WO | 2006/077168 | A1 | 7/2006 |
| WO | 2006/080884 | A1 | 8/2006 |
| WO | 2006/084017 | A2 | 8/2006 |
| WO | 2006/120133 | A2 | 11/2006 |
| WO | 2006/128129 | A2 | 11/2006 |
| WO | 2006/128172 | A2 | 11/2006 |
| WO | 2006/130403 | A1 | 12/2006 |
| WO | 2006/135604 | A2 | 12/2006 |
| WO | 2006/137772 | A1 | 12/2006 |
| WO | 2007/002313 | A2 | 1/2007 |
| WO | 2007/008541 | A1 | 1/2007 |
| WO | 2007/049158 | A2 | 5/2007 |
| WO | 2007/050980 | A2 | 5/2007 |
| WO | 2007/055374 | A1 | 5/2007 |
| WO | 2007/056341 | A1 | 5/2007 |
| WO | 2007/061880 | A1 | 5/2007 |
| WO | 2007/061978 | A1 | 5/2007 |
| WO | 2007/064797 | A2 | 6/2007 |
| WO | 2007/071598 | A1 | 6/2007 |
| WO | 2007/087129 | A2 | 8/2007 |
| WO | 2007/087130 | A2 | 8/2007 |
| WO | 2007/118137 | A1 | 10/2007 |
| WO | 2007/119463 | A1 | 10/2007 |
| WO | 2007/122830 | A1 | 11/2007 |
| WO | 2007/125984 | A1 | 11/2007 |
| WO | 2007/126765 | A2 | 11/2007 |
| WO | 2007/129044 | A1 | 11/2007 |
| WO | 2007/129052 | A1 | 11/2007 |
| WO | 2007/138072 | A2 | 12/2007 |
| WO | 2007/139002 | A1 | 12/2007 |
| WO | 2007/143557 | A2 | 12/2007 |
| WO | 2008/005457 | A2 | 1/2008 |
| WO | 2008/009963 | A2 | 1/2008 |
| WO | 2008/010985 | A2 | 1/2008 |
| WO | 2008/011611 | A2 | 1/2008 |
| WO | 2008/012418 | A1 | 1/2008 |
| WO | 2008/013963 | A2 | 1/2008 |
| WO | 2008/016643 | A2 | 2/2008 |
| WO | 2008/024970 | A2 | 2/2008 |
| WO | 2008/024978 | A2 | 2/2008 |
| WO | 2008/036272 | A1 | 3/2008 |
| WO | 2008/047229 | A2 | 4/2008 |
| WO | 2008/053913 | A1 | 5/2008 |
| WO | 2008/067874 | A1 | 6/2008 |
| WO | 2008/074788 | A1 | 6/2008 |
| WO | 2008/078837 | A1 | 7/2008 |
| WO | 2008/092199 | A1 | 8/2008 |
| WO | 2008/093024 | A2 | 8/2008 |
| WO | 2008/115262 | A2 | 9/2008 |
| WO | 2008/115719 | A1 | 9/2008 |
| WO | 2008/119015 | A2 | 10/2008 |
| WO | 2008/129280 | A1 | 10/2008 |
| WO | 2008/139152 | A1 | 11/2008 |
| WO | 2008/145843 | A1 | 12/2008 |
| WO | 2008/151184 | A1 | 12/2008 |
| WO | 2008/151211 | A1 | 12/2008 |

(56) References Cited

FOREIGN PATENT DOCUMENTS

| | | |
|---|---|---|
| WO | 2008/154221 A2 | 12/2008 |
| WO | 2009/005638 A2 | 1/2009 |
| WO | 2009/022171 A1 | 2/2009 |
| WO | 2009/032861 A1 | 3/2009 |
| WO | 2009/037001 A2 | 3/2009 |
| WO | 2009/052319 A1 | 4/2009 |
| WO | 2009/078992 A1 | 6/2009 |
| WO | 2009/100406 A2 | 8/2009 |
| WO | 2009/109710 A1 | 9/2009 |
| WO | 2009/115267 A2 | 9/2009 |
| WO | 2009/156484 A2 | 12/2009 |
| WO | 2010/006191 A1 | 1/2010 |
| WO | 2010/007046 A2 | 1/2010 |
| WO | 2010/007756 A1 | 1/2010 |
| WO | 2010/008739 A2 | 1/2010 |
| WO | 2010/032147 A2 | 3/2010 |
| WO | 2010/034838 A2 | 4/2010 |
| WO | 2010/046780 A2 | 4/2010 |
| WO | 2010/068863 A2 | 6/2010 |
| WO | 2010/075376 A2 | 7/2010 |
| WO | 2010/088574 A1 | 8/2010 |
| WO | 2010/108921 A1 | 9/2010 |
| WO | 2010/111527 A1 | 9/2010 |
| WO | 2010/112520 A1 | 10/2010 |
| WO | 2010/127855 A1 | 11/2010 |
| WO | 2010/137350 A1 | 12/2010 |
| WO | 2010/151747 A1 | 12/2010 |
| WO | 2011/008931 A2 | 1/2011 |
| WO | 2011/012661 A1 | 2/2011 |
| WO | 2011/072275 A2 | 6/2011 |
| WO | 2011/073328 A1 | 6/2011 |
| WO | 2011/082400 A2 | 7/2011 |
| WO | 2011/119869 A1 | 9/2011 |
| WO | 2011/125568 A1 | 10/2011 |
| WO | 2011/133920 A1 | 10/2011 |
| WO | 2011/134925 A1 | 11/2011 |
| WO | 2012/003405 A1 | 1/2012 |
| WO | 2012/004217 A1 | 1/2012 |
| WO | 2012/020131 A2 | 2/2012 |
| WO | 2012/020133 A1 | 2/2012 |
| WO | 2012/024604 A2 | 2/2012 |
| WO | 2012/061337 A1 | 5/2012 |
| WO | 2012/064559 A1 | 5/2012 |
| WO | 2012/074050 A1 | 6/2012 |
| WO | 2012/085650 A1 | 6/2012 |
| WO | 2012/085789 A1 | 6/2012 |
| WO | 2012/101062 A1 | 8/2012 |
| WO | 2012/117097 A1 | 9/2012 |
| WO | 2012/123745 A1 | 9/2012 |
| WO | 2012/127385 A1 | 9/2012 |
| WO | 2012/147890 A1 | 11/2012 |
| WO | 2012/149540 A1 | 11/2012 |
| WO | 2012/152915 A1 | 11/2012 |
| WO | 2012/154880 A1 | 11/2012 |
| WO | 2012/156918 A1 | 11/2012 |
| WO | 2012/156919 A1 | 11/2012 |
| WO | 2012/156920 A1 | 11/2012 |
| WO | 2012/166951 A1 | 12/2012 |
| WO | 2013/013815 A1 | 1/2013 |
| WO | 2013/013817 A1 | 1/2013 |
| WO | 2013/017480 A1 | 2/2013 |
| WO | 2013/024004 A1 | 2/2013 |
| WO | 2013/033068 A1 | 3/2013 |
| WO | 2013/041602 A1 | 3/2013 |
| WO | 2013/055984 A1 | 4/2013 |
| WO | 2013/059648 A1 | 4/2013 |
| WO | 2013/064884 A1 | 5/2013 |
| WO | 2013/152198 A1 | 10/2013 |
| WO | 2013/152727 A1 | 10/2013 |
| WO | 2013/163404 A1 | 10/2013 |
| WO | 2013/178816 A1 | 12/2013 |
| WO | 2013/180193 A1 | 12/2013 |
| WO | 2013/188813 A2 | 12/2013 |
| WO | 2014/000418 A1 | 1/2014 |
| WO | 2014/005125 A2 | 1/2014 |
| WO | 2014/012511 A1 | 1/2014 |
| WO | 2014/015167 A2 | 1/2014 |
| WO | 2014/025808 A1 | 2/2014 |
| WO | 2014/031928 A2 | 2/2014 |
| WO | 2014/047111 A1 | 3/2014 |
| WO | 2014/055955 A1 | 4/2014 |
| WO | 2014/056620 A1 | 4/2014 |
| WO | 2014/074906 A1 | 5/2014 |
| WO | 2014/081299 A1 | 5/2014 |
| WO | 2014/081300 A1 | 5/2014 |
| WO | 2014/081301 A1 | 5/2014 |
| WO | 2014/081303 A1 | 5/2014 |
| WO | 2014/089112 A1 | 6/2014 |
| WO | 2014/144169 A1 | 9/2014 |
| WO | 2014/146995 A1 | 9/2014 |
| WO | 2014/149164 A1 | 9/2014 |
| WO | 2014/151936 A1 | 9/2014 |
| WO | 2014/153208 A1 | 9/2014 |
| WO | 2014/164704 A2 | 10/2014 |
| WO | 2014/181287 A1 | 11/2014 |
| WO | 2014/187297 A1 | 11/2014 |
| WO | 2014/187298 A1 | 11/2014 |
| WO | 2014/190199 A1 | 11/2014 |
| WO | 2014/194270 A1 | 12/2014 |
| WO | 2015/031725 A1 | 3/2015 |
| WO | 2015/035059 A1 | 3/2015 |
| WO | 2015/051043 A1 | 4/2015 |
| WO | 2015/051458 A1 | 4/2015 |
| WO | 2015/061247 A2 | 4/2015 |
| WO | 2015/077246 A1 | 5/2015 |
| WO | 2015/110999 A1 | 7/2015 |
| WO | 2015/120800 A1 | 8/2015 |
| WO | 2015/140572 A1 | 9/2015 |
| WO | 2015/142903 A2 | 9/2015 |
| WO | 2015/157057 A1 | 10/2015 |
| WO | 2015/170218 A1 | 11/2015 |
| WO | 2016/020307 A1 | 2/2016 |
| WO | 2016/042341 A1 | 3/2016 |
| WO | 2016/057779 A2 | 4/2016 |
| WO | 2016/058544 A1 | 4/2016 |
| WO | 2016/061527 A1 | 4/2016 |
| WO | 2016/100711 A1 | 6/2016 |
| WO | 2016/133838 A1 | 8/2016 |
| WO | 2016/173557 A1 | 11/2016 |
| WO | 2016/176657 A1 | 11/2016 |
| WO | 2016/183266 A1 | 11/2016 |
| WO | 2017/007755 A1 | 1/2017 |
| WO | 2017/007756 A1 | 1/2017 |
| WO | 2017/027984 A1 | 2/2017 |
| WO | 2017/044889 A1 | 3/2017 |
| WO | 2017/046133 A1 | 3/2017 |
| WO | 2017/075694 A1 | 5/2017 |
| WO | 2017/106818 A1 | 6/2017 |
| WO | 2017/146116 A1 | 8/2017 |
| WO | 2017/156265 A1 | 9/2017 |

OTHER PUBLICATIONS

Wagner et al., Kinetically Selective Inhibitors of Histone Deacetylase 2 (HDAC2) as Cognition Enhancers. Chem Sci. Jan. 1, 2015;6(1):804-815.

Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8.

Copending U.S. Appl. No. 15/741,657, filed Jan. 3, 2018.

Copending U.S. Appl. No. 15/867,982, filed Jan. 11, 2018.

Bennett et al., Cecil Textbook of Medicine, 2th Edition, W.B. Sanders Company, Philadelphia. vol. 1, pp. 1004-1010, (1996).

CDC, CDC and Fungal Diseases. Retrieved online at: http://www.cdc.gov/ncezid/dfwed/mycotics. 2 pages, Sep. 2011.

Dorostkar et al., Analyzing dendritic spine pathology in Alzheimer's disease: problems and opportunities. Acta Neuropathol. Jul. 2015;130(1):1-19.

Gura, Systems for identifying new drugs are often faulty. Science. Nov. 7, 1997;278(5340)1041-2.

Johnson et al., Relationships between drug activity in NCI preclinical in vitro and in vivo models and early clinical trials. Br J Cancer. May 18, 2001;84(10)1424-31.

(56) References Cited

OTHER PUBLICATIONS

Kattar et al., Parallel medicinal chemistry approaches to selective HDAC1/HDAC2 inhibitor (SHI-1:2) optimization. Bioorg Med Chem Lett. Feb. 15, 2009;19(4):1168-72.

MedicineNet.com, Definition of Cancer. Retrieved online at: http://www.medterms.com. 1 page, Sep. 18, 2004.

Pearce et al., Failure modes in anticancer drug discovery and development. Cancer Drug Design and Discovery, Elsevier Inc., Stephen Neidle (Ed.). Chapter 18, pp. 424-435, (2008).

Stevens, Fungal Skin Infections. UNM School of Medicine, Continuum of Care. Retrieved online at: hsc.unm.edu/som/coc. 1 page, (2000).

Zhu et al., Investigation on the isoform selectivity of histone deacetylase inhibitors using chemical feature based pharmacophore and docking approaches. Eur J Med Chem. May 2010;45(5):1777-91.

HETEROBICYCLIC N-AMINOPHENYL-AMIDES AS INHIBITORS OF HISTONE DEACETYLASE

REFERENCE TO RELATED APPLICATIONS

This application is a § 371 national stage filing of International Application No. PCT/US2016/040956, filed Jul. 5, 2016, which claims the benefit of U.S. Provisional Application No. 62/188,854, filed Jul. 6, 2015, the entire contents of each of which are incorporated herein by reference.

BACKGROUND OF THE INVENTION

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs. Marks, P., Rifkind, R. A., Richon, V. M., Breslow, R., Miller, T., Kelly, W. K. Histone deacetylases and cancer: causes and therapies. Nat Rev Cancer, 1, 194-202, (2001); and Marks, P. A., Richon, V. M., Miller, T., Kelly, W. K. Histone deacetylase inhibitors. Adv Cancer Res, 91, 137-168, (2004). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. Langley, B., Gensert, J. M., Beal, M. F., Ratan, R. R. Remodeling chromatin and stress resistance in the central nervous system: histone deacetylase inhibitors as novel and broadly effective neuroprotective agents. Curr Drug Targets CNS Neurol Disord, 4, 41-50, (2005). A recent review has summarized the evidence that aberrant histone acetyltransferase (HAT) and histone deacetylases (HDAC) activity may represent a common underlying mechanism contributing to neurodegeneration. Moreover, using a mouse model of depression, Nestler has recently highlighted the therapeutic potential of histone deacetylation inhibitors (HDAC5) in depression. Tsankova, N. M., Berton, O., Renthal, W., Kumar, A., Neve, R. L., Nestler, E. J. Sustained hippocampal chromatin regulation in a mouse model of depression and antidepressant action. Nat Neurosci, 9, 519-525, (2006).

There are 18 known human histone deacetylases, grouped into four classes based on the structure of their accessory domains. Class I includes HDAC1, HDAC2, HDAC3, and HDAC8 and has homology to yeast RPD3. HDAC4, HDAC5, HDAC7, and HDAC9 belong to class IIa and have homology to yeast. HDAC6 and HDAC10 contain two catalytic sites and are classified as class IIb. Class III (the sirtuins) includes SIRT1, SIRT2, SIRT3, SIRT4, SIRT5, SIRT6, and SIRT7. HDAC11 is another recently identified member of the HDAC family and has conserved residues in its catalytic center that are shared by both class I and class II deacetylases and is sometimes placed in class IV.

In contrast, HDACs have been shown to be powerful negative regulators of long-term memory processes. Non-specific HDAC inhibitors enhance synaptic plasticity as well as long-term memory (Levenson et al., 2004, J. Biol. Chem. 279:40545-40559; Lattal et al., 2007, Behav Neurosci 121: 1125-1131; Vecsey et al., 2007, J. Neurosci 27:6128; Bredy, 2008, Learn Mem 15:460-467;Guan et al., 2009, Nature 459:55-60; Malvaez et al., 2010, Biol. Psychiatry 67:36-43; Roozendaal et al., 2010, J. Neurosci. 30:5037-5046). For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition have considerable therapeutic potential for many memory and cognitive disorders.

Currently, the role of individual HDACs in long-term memory has been explored in two recent studies. Kilgore et al. 2010, Neuropsychopharmacology 35:870-880 revealed that nonspecific HDAC inhibitors, such as sodium butyrate, inhibit class I HDACs (HDAC1, HDAC2, HDAC3, HDAC8) with little effect on the class IIa HDAC family members (HDAC4, HDAC5, HDAC7, HDAC9). This suggests that inhibition of class I HDACs may be critical for the enhancement of cognition observed in many studies. Indeed, forebrain and neuron specific over expression of HDAC2, but not HDAC1, decreased dendritic spine density, synaptic density, synaptic plasticity and memory formation. (Guan et al., 2009, Nature, 459:55-60). In contrast, HDAC2 knockout mice exhibited increased synaptic density, increased synaptic plasticity and increased dendritic density in neurons. These HDAC2 deficient mice also exhibited enhanced learning and memory in a battery of learning behavioral paradigms. This work demonstrates that HDAC2 is a key regulator of synaptogenesis and synaptic plasticity. Additionally, Guan et al. showed that chronic treatment of mice with SAHA (an HDAC 1, 2, 3, 6, 8 inhibitor) reproduced the effects seen in the HDAC2 deficient mice and recused the cognitive impairment in the HDAC2 overexpression mice.

Accordingly, the inhibition of the HDAC2 (selectively or in combination with inhibition of other class I HDACs) is an attractive therapeutic target. Such inhibition has the potential for enhancing cognition and facilitating the learning process through increasing synaptic and dendritic density in neuronal cell populations. In addition, inhibition of HDAC2 may also be therapeutically useful in treating a wide variety of other diseases and disorders.

DETAILED DESCRIPTION OF THE INVENTION

1. General Description of Certain Embodiments of the Invention

This invention provides compounds that are inhibitors of HDAC2. The compounds accordingly are useful for treating, alleviating, or preventing a condition in a subject such as a neurological disorder, memory or cognitive function disorder or impairment, extinction learning disorder, fungal disease or infection, inflammatory disease, hematological disease, or neoplastic disease, or for improving memory or treating, alleviating, or preventing memory loss or impairment.

In some embodiments the present invention provides a compound of Formula I:

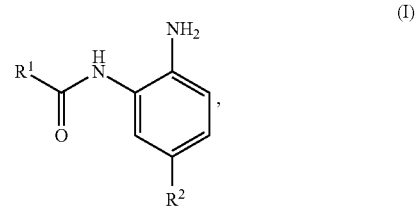

or a pharmaceutically acceptable salt thereof, wherein:
$R^1$ is an optionally substituted, bicyclic fused, spirofused or bridged, non-aromatic heterocyclyl, comprising at least two heteroatoms independently selected from N, O and S, wherein each ring of $R^1$ comprises at least one of the heteroatoms; and $R^2$ is selected from heteroaryl and para-substituted aryl, wherein $R^2$ is optionally further substituted, and $R^2$ is other than optionally substituted biphenyl and optionally substituted thiophenyl.

2. Compounds and Definitions:

Compounds of this invention include those described generally for Formula I, above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means a straight-chain or branched $C_{1-12}$ hydrocarbon which is completely saturated or which contains one or more units of unsaturation. For example, suitable aliphatic groups include linear or branched alkyl, alkenyl, alkynyl, alkylene, alkenylene, and alkynylene groups. Unless otherwise specified, in various embodiments, aliphatic groups have 1-12, 1-10, 1-8, 1-6, 1-4, 1-3, or 1-2 carbon atoms. Aliphatic groups can be unsubstituted or substituted (e.g., having 1, 2, 3, or 4 substituent groups as defined herein).

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms, and which is not aromatic. In some embodiments, the cycloaliphatic group is polycyclic (e.g., a linear fused, bridged, or spirofused polycyclic such as a linear-fused or spirofused carbocycle that is bicyclic or tricyclic, or a tricyclic bridged carbocycle). In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

As used herein, the term "halogen" or "halo" means F, Cl, Br, or I.

The terms "aryl" and "a-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Unless described to the contrary, aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic, as long as each ring is aromatic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, and/or heterocyclic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3- b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered polycyclic (e.g., bicyclic) moiety that is either saturated or partially unsaturated in at least one ring, and having, in addition to carbon atoms, one or more, preferably one to four, heteroatoms, as defined above. In some embodiments, the heterocyclic group is polycyclic (e.g., a fused, bridged, or spirofused polycyclic heterocyclyl that is bicyclic or tricyclic).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. Unless otherwise specified, a heterocyclyl group may be mono-, bi-, tri-, or polycyclic, preferably mono-, bi-, or tricyclic, more preferably mono- or bicyclic. Additionally, a heterocyclic ring also includes groups in which the heterocyclic ring is fused to one or more aryl, heteroaryl and/or carbocyclic rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

An aryl or heteroaryl group may contain one or more substituents (e.g., 1, 2, 3, or 4 substituents) and thus may be "optionally substituted". In addition to the substituents defined above and herein, suitable substituents on the unsaturated carbon atom of an aryl or heteroaryl group also include and are generally selected from —halo, —$NO_2$, —CN, —$R^+$, —C($R^+$)=C($R^+$)$_2$, —C≡C—$R^+$, —$OR^+$, —$SR^o$, —S(O)$R^o$, —$SO_2R^o$, —$SO_3R^+$, —$SO_2N(R^+)_2$, —N($R^+$)$_2$, —$NR^+$C(O)$R^+$, —$NR^+$C(S)$R^+$, —$NR^+$C(O)N($R^+$)$_2$, —$NR^+$C(S)N($R^+$)$_2$, —N($R^+$)C(=$NR^+$)—N($R^+$)$_2$, —N($R^+$)C(=$NR^+$)—$R^o$, —$NR^+CO_2R^+$, —$NR^+SO_2R^o$, —$NR^+SO_2N(R^+)_2$, —O—C(O)$R^+$, —O—$CO_2R^+$, —OC(O)N($R^+$)$_2$, —C(O)$R^+$, —C(S)$R^o$, —$CO_2R^+$, —C(O)—C(O)$R^+$, —C(O)N($R^+$)$_2$, —C(S)N($R^+$)$_2$, —C(O)N($R^+$)—$OR^+$, —C(O)N($R^+$)C(=$NR^+$)—N($R^+$)$_2$, —N($R^+$)C(=$NR^+$)—N($R^+$)—C(O)$R^+$, —C(=$NR^+$)—N($R^+$)$_2$, —C(=$NR^+$)—$OR^+$, —N($R^+$)—N($R^+$)$_2$, —C(=$NR^+$)—N($R^+$)—$OR^+$, —C($R^o$)=N—$OR^+$, —P(O)($R^+$)$_2$, —P(O)($OR^+$)$_2$, —O—P(O)—$OR^+$, and —P(O)($NR^+$)—N($R^+$)$_2$, wherein $R^+$, independently, is hydrogen or an aliphatic, aryl, heteroaryl, cycloaliphatic, or heterocyclyl group, or two independent °Ccurrences of $R^+$ that are bound to the same atom are taken together with their intervening atom(s) to form an optionally substituted 5-7-membered aryl, heteroaryl, cycloaliphatic, or heterocyclyl ring. When R+ is not hydrogen, R+ may be unsubstituted or substituted with 1, 2, 3, or 4 substituent groups. Each $R^o$ is an aliphatic, aryl, heteroaryl, cycloaliphatic, or heterocyclyl group, wherein $R^o$ is unsubstituted or substituted with 1, 2, 3, or 4 substituent groups.

A carbocyclic ring or a heterocyclic ring may contain one or more substituents and thus may be "optionally substituted". Unless otherwise defined above and herein, suitable substituents on any saturated carbon of a carbocyclic ring or a heterocyclic ring are selected from those listed above for the carbon atoms of an aryl or heteroaryl group and additionally include the following: =O, =S, =C($R^*$)$_2$, =N—N($R^*$)$_2$, =N—$OR^*$, =N—NHC(O)$R^*$, =N—$NHCO_2R^o$=N—$NHSO_2R^o$ or =N—$R^*$ where $R^o$ is defined above, and each $R^*$ is independently selected from hydrogen or an $C_{1-6}$ aliphatic group that is unsubstituted or substituted with 1, 2, 3, or 4 substituent groups.

In addition to the substituents defined above and herein, optional substituents on the nitrogen of a non-aromatic heterocyclic ring also include and are generally selected from —$R^+$, —N($R^+$)$_2$, —C(O)$R^+$, —C(O)$OR^+$, —C(O)C(O)$R^+$, —C(O)$CH_2$C(O)$R^+$, —S(O)$_2R^+$, —S(O)$_2$N($R^+$)$_2$, —C(S)N($R^+$)$_2$, —C(=NH)—N($R^+$)$_2$, or —N($R^+$)S(O)$_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent °Ccurrences of $R^+$ (or any other variable similarly defined in the specification and claims herein) that are bound to the same atom, can be taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

With respect to the compounds defined by generic Formula I, unless otherwise specified, one or more hydrogens can be replaced by deuterium. Isotopic enrichments include e.g., at least 10%, 25%, 50%, 75%, 80%, 85%, 90%, 95%, 87%, 98%, 99.0%, 99.5% and 99.8%. In one embodiment, all hydrogen atoms represented in Formula I are present in natural abundance. With respect to specific compounds disclosed herein, such as those in Table 1 and in the Exemplification section, all hydrogen atoms are present in natural abundance unless otherwise specified.

It is to be understood that, when a disclosed compound has at least one chiral center, the present invention encompasses one enantiomer free from the corresponding optical isomer, racemic mixture of the compound and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

As described generally above, in some embodiments the present invention provides a compound of Formula I:

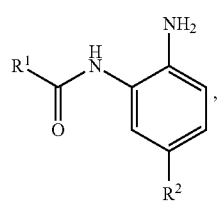

(I)

or a pharmaceutically acceptable salt thereof, wherein:

$R^1$ is an optionally substituted, bicyclic fused, spirofused or bridged, non-aromatic heterocyclyl, comprising at least two heteroatoms independently selected from N, O and S, wherein each ring of $R^1$ comprises at least one of the heteroatoms; and $R^2$ is selected from heteroaryl and para-substituted aryl, wherein $R^2$ is optionally further substituted, and $R^2$ is other than optionally substituted biphenyl and optionally substituted thiophenyl.

In some embodiments, the compound is other than

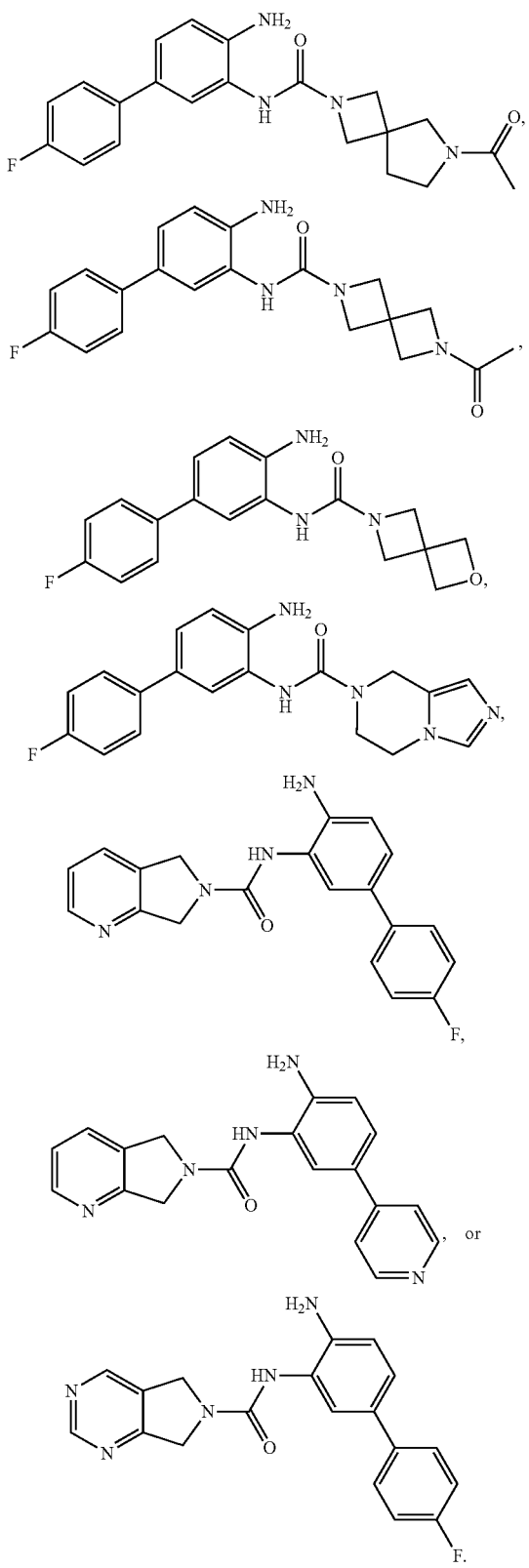

In some embodiments, $R^1$ is an optionally substituted bicyclic fused non-aromatic heterocyclyl comprising at least two heteroatoms independently selected from N, O and S, wherein each ring of $R^1$ comprises at least one of the heteroatoms.

In other embodiments, $R^1$ is an optionally substituted spirofused non-aromatic heterocyclyl (e.g., a bicyclic heterocyclyl), comprising at least two heteroatoms independently selected from N, O and S, wherein each ring of $R^1$ comprises at least one of the heteroatoms.

In other embodiments, $R^1$ is an optionally substituted bridged, non-aromatic heterocyclyl, comprising at least two heteroatoms independently selected from N, O and S, wherein each ring of $R^1$ comprises at least one of the heteroatoms.

In some embodiments, $R^1$ is unsubstituted.

In other embodiments, $R^1$ is substituted with, e.g., 1, 2, 3, or 4 independently selected substituents.

In some embodiments, $R^1$ is selected from: 6,7-dihydrothiazolo[5,4-c]pyridin-2-yl; 4,5,6,7-tetrahydrothiazolo[4,5-c]pyridin-2-yl; 4,5,6,7-tetrahydrothiazolo[5,4-c]pyridin-2-yl; 2-oxa-8-azaspiro[4.5]decan-8-yl; 1,3-dihydro-2H-pyrrolo[3,4-c]pyridin-2-yl; 2,8-diazaspiro[4.5]decan-8-yl; 2,8-diazaspiro[4.5]decan-2-yl; hexahydropyrrolo[3,4-c]pyrrol-2(1H)-yl; 5,6,7,8-tetrahydroimidazo[1,2-a]pyrazin-2-yl; 5,6,7,8-tetrahydroimidazo[1,2-a]pyridin-2-yl; 2-oxa-7-azaspiro[3.5]nonan-7-yl; 5,7-dihydro-6H-pyrrolo[3,4-b]pyrazin-6-yl; °Ctahydro-5H-pyrrolo[3,4-c]pyridin-5-yl; 5-oxa-2-azaspiro[3.5]nonan-2-yl; 5,7-dihydro-6H-pyrrolo[3,4-d]pyrimidin-6-yl; 8-oxa-2-azaspiro[4.5]decan-2-yl; 7-oxa-2-azaspiro[3.5]nonan-2-yl; 2,7-diazaspiro[3.5]nonan-2-yl; 2,7-diazaspiro[3.5]nonan-7-yl; 2,7-diazaspiro[4.4]nonan-2-yl; °Ctahydro-2H-pyrrolo[3,4-c]pyridin-2-yl; 3,8-diazabicyclo[3.2.1]octan-3-yl; 3,8-diazabicyclo[3.2.1]octan-8-yl; 3,8-diazabicyclo[3.2.1]octan-8-yl; 2,5-diazabicyclo[2.2.1]heptan-2-yl; 8-oxa-3-azabicyclo[3.2.1]octan-3-yl; 5,6,7,8-tetrahydro-4H-thiazolo[4,5-d]azepin-2-yl; 6,7-dihydro-4H-pyrano[4,3-d]thiazol-2-yl; 5,7-dihydro-6H-pyrrolo[3,4-b]pyridin-6-yl; 2-oxa-6-azaspiro[3.4]octan-6-yl; 2-oxa-6-azaspiro[3.3]heptan-6-yl; and 2,6-diazaspiro[3.4]octan-6-yl, wherein $R^1$ is optionally substituted with up to 4 independently selected substituents.

In some embodiments, $R^1$ is selected from:

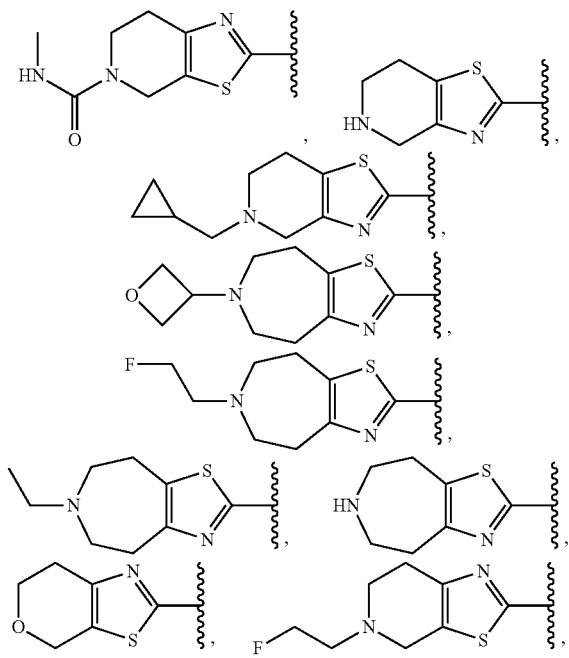

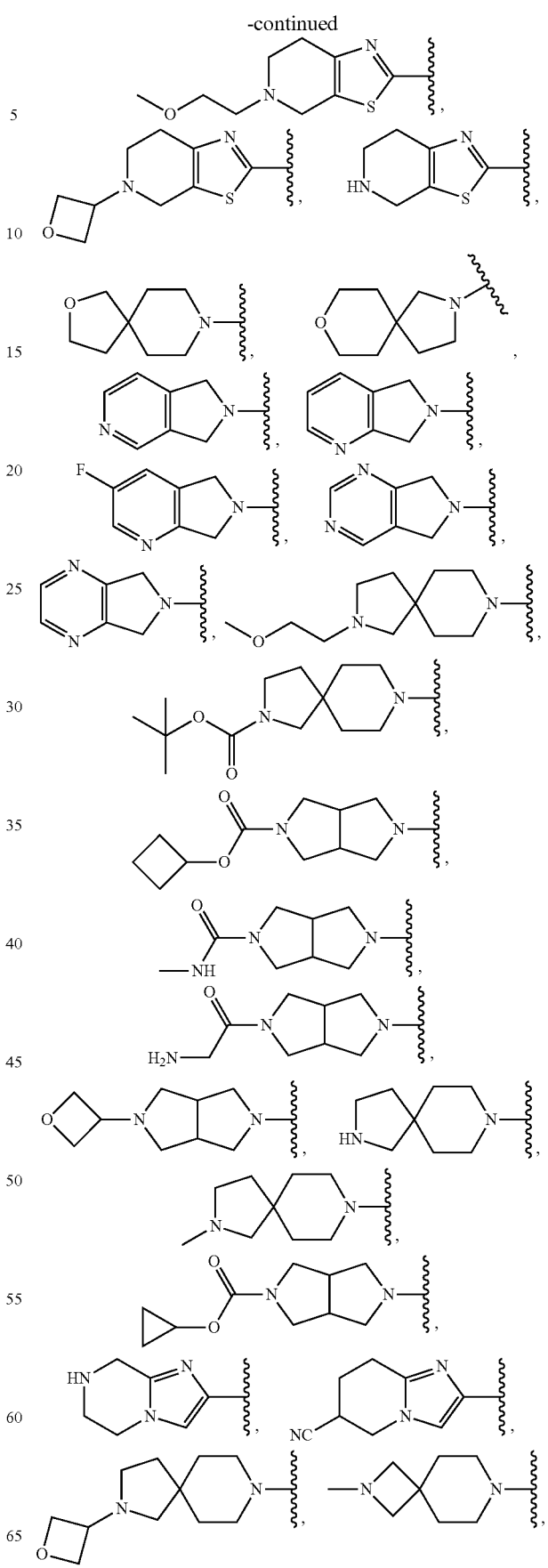

-continued
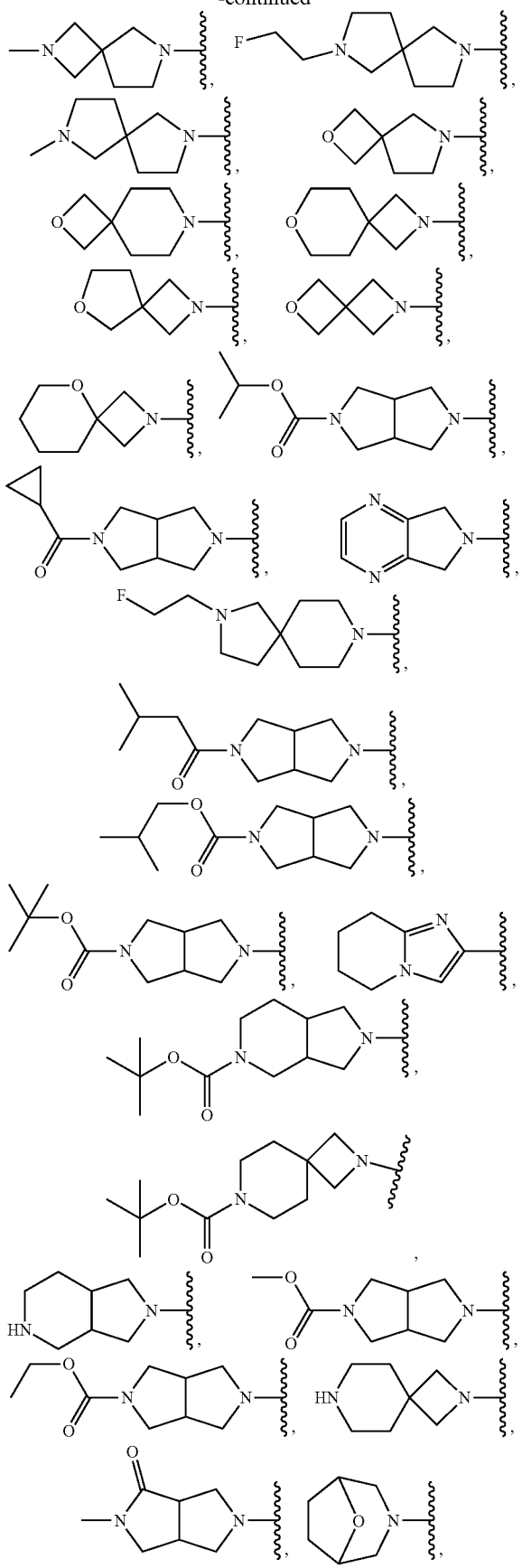
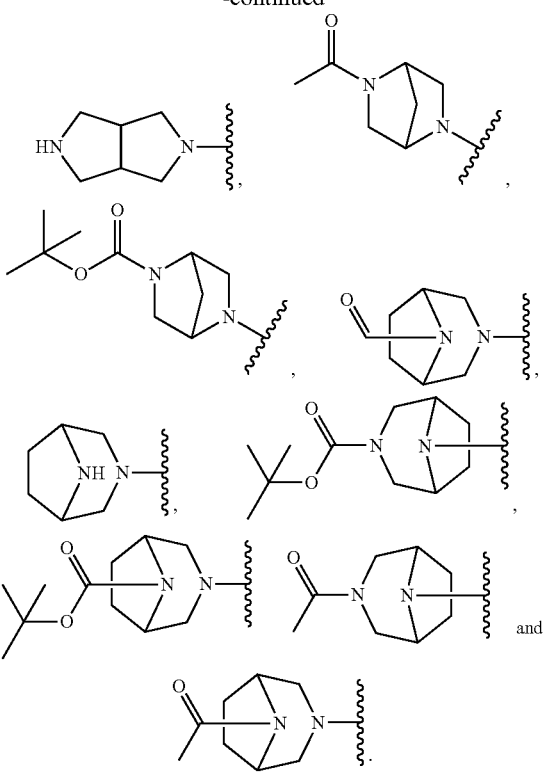
In certain embodiments, R¹ is selected from:
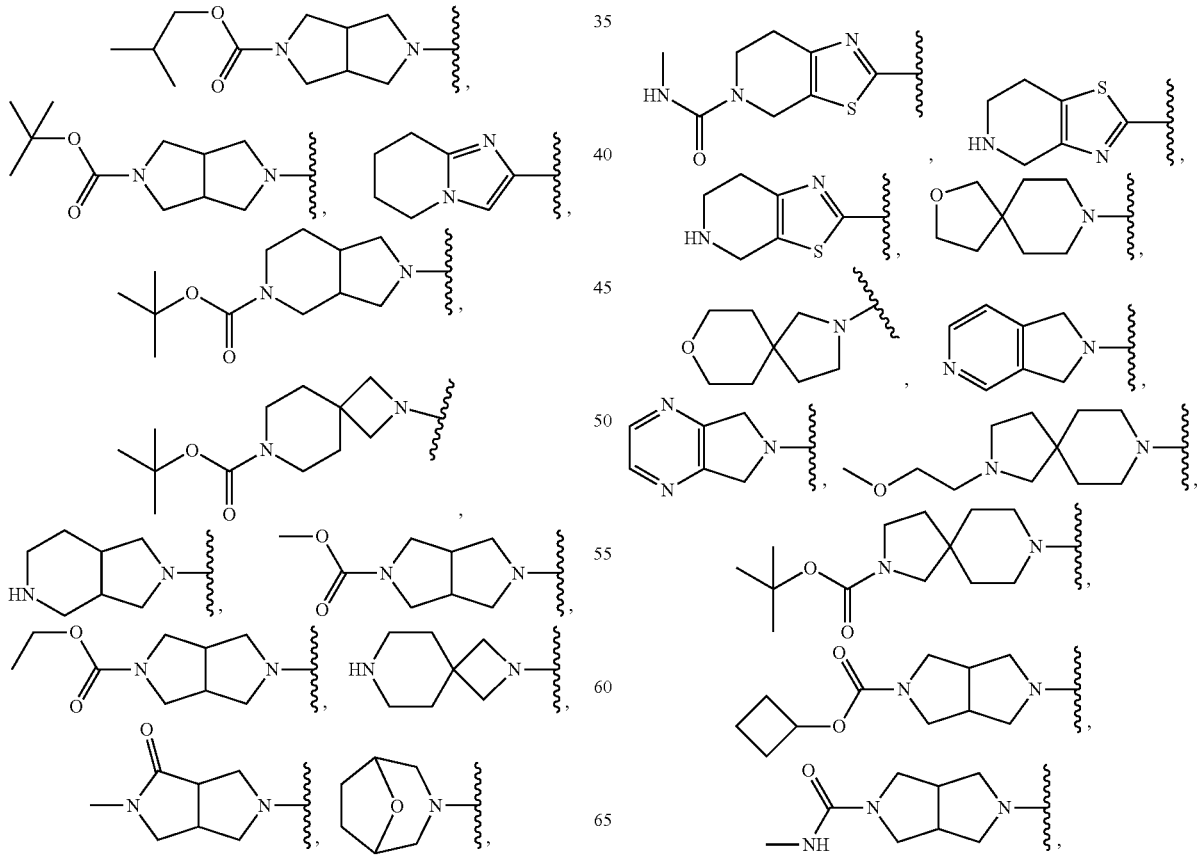

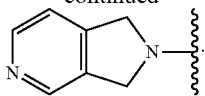

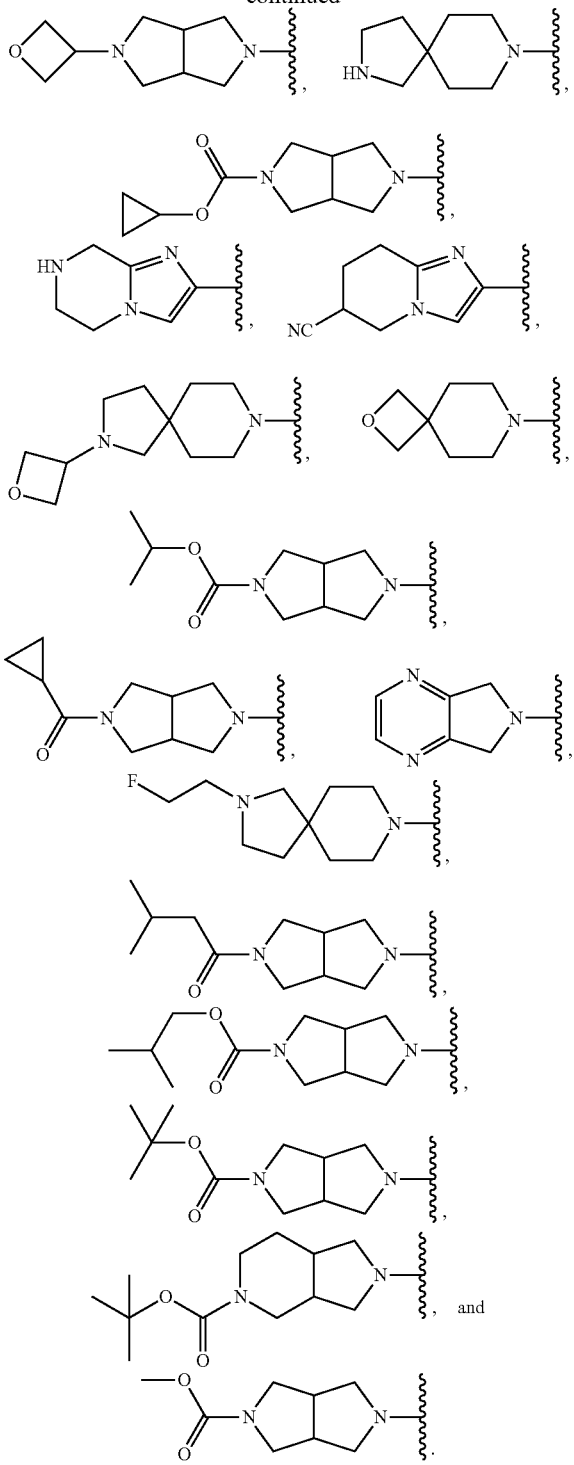

In still other embodiments, R¹ is selected from:

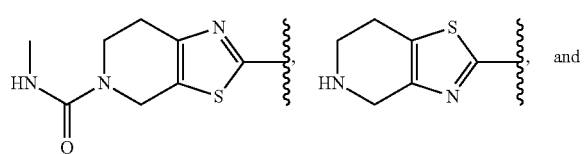

In some embodiments, R² is an optionally substituted heteroaryl that is not optionally substituted thiophenyl.

In some embodiments, R² is para-substituted aryl, wherein R² is optionally further substituted, and R² is other than optionally substituted biphenyl.

In some embodiments, R² is unsubstituted.

In other embodiments, R² is substituted with, e.g., 1, 2, 3, or 4 substituents as described herein.

In some embodiments, R² is selected from para-substituted phenyl, pyridinyl, furanyl, 1H-pyrazolyl, thiazolyl, isoxazolyl, oxazolyl, isothiazolyl, 5,6-dihydro-4H-pyrrolo[1,2-b]pyrazolyl, pyridazinyl, and pyrimidinyl, and wherein R² is optionally additionally substituted.

In other embodiments, R² is selected from 4-fluorophenyl, 4-methoxyphenyl, 4-chlorophenyl, 4-difluromethoxyphenyl, 4-cyanophenyl, 4-trifluoromethylphenyl, 2,4-difluorophenyl, 3,4-difluorophenyl, 3-chloro-4-fluorophenyl, 3,4,5-trifluorophenyl, 2-fluoro-4-trifluoromethylphenyl, 2-methyl-4-fluorophenyl, pyridin-2-yl, pyridin-3-yl, pyridin-4-yl, 5-trifluoromethylpyridin-2-yl, 6-methoxypyridin-3-yl, 6-methylpyridin-3-yl, 6-fluoropyridin-3-yl, 2-methylpyridin-4-yl, 2-fluoropyridin-4-yl, furan-2-yl, 5-methylfuran-2-yl, 5-chlorofuran-2-yl, furan-3-yl, 5-methylfuran-3-yl, 5-chlorofuran-3-yl, 1H-pyrazol-4-yl, 1-ethyl-1H-pyrazol-4-yl, 1-methyl-1H-pyrazol-4-yl, 1-cyclobutyl-1H-pyrazol-4-yl, 1,5-dimethyl-1H-pyrazol-4-yl, 2-methylthiazol-5-yl, 3-methylisoxazol-5-yl, 2-methyloxazoly-5-yl, 3-methylisothiazol-5-yl, 5,6-dihydro-4H-pyrrolo[1,2-b]pyrazol-3-yl, 6-methylpyridazin-4-yl, 6-methylpyridazin-3-yl, and pyrimidin-3-yl.

In further embodiments, R² is selected from 4-fluorophenyl, 4-methoxyphenyl, 4-chlorophenyl, 4-difluromethoxyphenyl, 4-cyanophenyl, 2,4-difluorophenyl, 3,4-difluorophenyl, pyridin-3-yl, pyridin-4-yl, furan-2-yl, furan-3-yl, and 1-methyl-1H-pyrazol-4-yl.

In still other embodiments, R² is selected from 4-fluorophenyl, 4-methoxyphenyl, 4-difluromethoxyphenyl, pyridin-4-yl, furan-2-yl, and furan-3-yl Although, as indicated above, various embodiments and aspects thereof for a variable in any of the formulas described herein (e.g., a compound according to Formula (I)) may be selected from a group of chemical moieties, the invention also encompasses as further embodiments and aspects thereof situations where such variable is: a) selected from any subset of chemical moieties in such a group; and b) any single member of such a group. Further, where various embodiments and aspects thereof are set forth individually for each variable in any of the formulas described herein (e.g., a compound according to Formula (I)), the invention encompasses all possible combinations of the different embodiments and aspects for each of the variables in the Formula.

Exemplary compounds of and useful in the present invention are set forth in Table 1 below, along with mass spectrometry and nuclear magnetic resonance data for certain compounds. In certain embodiments, the present invention provides a compound depicted in Table 1, or a pharmaceutically acceptable salt thereof.

TABLE 1

Exemplary Compounds

| No. | Structure | MS Calc. | MS found | ¹H NMR Data (400 MHz, DMSO-d$_6$) |
|---|---|---|---|---|
| 100 | 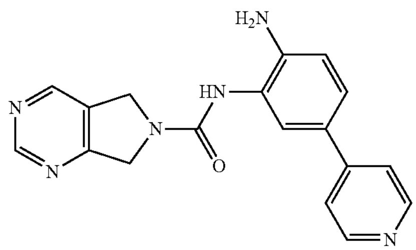 [SMILES: Nc1ccc(-c2ccncc2)cc1NC(=O)N1Cc2cncnc2C1] | 332 | 333 | δ 9.12 (s, 1H), 8.84 (s, 1H), 8.50 (d, J = 6.0 Hz, 2H), 8.21 (br, 1H), 7.92 (s, 1H), 7.58-7.55 (m, 2H), 7.45 (dd, J = 8.4 Hz, J = 2.0 Hz, 1H), 5.38 (s, 1H), 4.83 (s, 1H), 5.38 (s, 1H), 4.83 (s, 4H). |
| 101 | 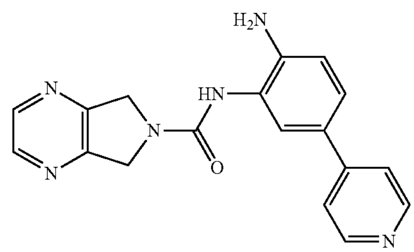 [SMILES: Nc1ccc(-c2ccncc2)cc1NC(=O)N1Cc2nccnc2C1] | 332 | 333 | δ 8.55 (s, 2H), 8.50 (d, J = 6.0 Hz, 2H), 7.93 (br, 1H), 7.58-7.55 (m, 3H), 7.46 (dd, J = 8.4 Hz, 6.0 Hz, 1H), 6.84 (d, J = 8.4 Hz, 1H), 5.38 (br, 2H), 4.84 (s, 4H). |
| 102 | 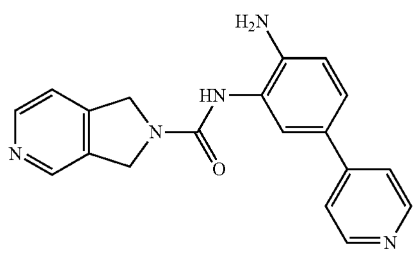 [SMILES: Nc1ccc(-c2ccncc2)cc1NC(=O)N1Cc2ccncc2C1] | 331 | 332 | δ 8.62 (s, 1H), 8.50 (t, J = 3.2 Hz, 3H), 7.85 (s, 1H), 7.58 (d, J = 2.4 Hz, 1H), 7.55 (d, J = 6.0 Hz, 2H), 7.45-7.43 (m, 2H), 6.82 (d, J = 8.4 Hz, 1H), 5.37 (s, 2H), 4.83 (d, J = 6.4 Hz, 4H). |
| 103 | 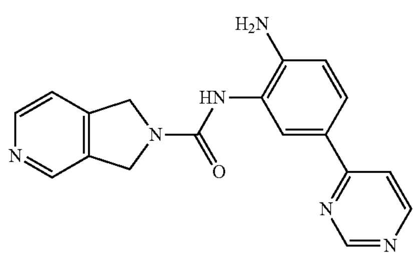 [SMILES: Nc1ccc(-c2ccncn2)cc1NC(=O)N1Cc2ccncc2C1] | 332 | 333 | δ 9.04 (s, 1H), 8.64 (d, J = 5.6 Hz, 1H), 8.62 (s, 1H), 8.50 (d, J = 5.2 Hz, 1H), 7.44 (d, J = 4.8 Hz, 1H), 6.81 (d, J = 8.4 Hz, 1H), 5.63 (s, 1H), 4.82 (d, J = 6.4 Hz, 4H). |
| 104 | 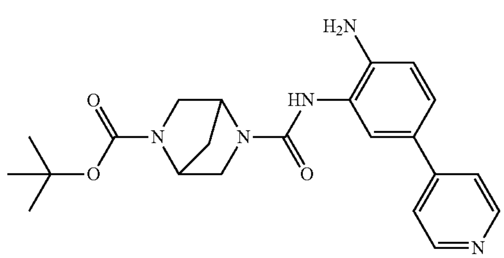 [SMILES: CC(C)(C)OC(=O)N1CC2CC1CN2C(=O)Nc1cc(-c2ccncc2)ccc1N] | 409 | 410 | δ 7.66 (s, 2H), 6.84 (s, 2H), 6.69 (s, 1H), 6.67 (br, 1H), 6.12 (br, 1H), 3.96 (s, 1H), 3.76 (s, 1H), 2.76-2.61 (m, 4H), 1.16 (s, 2H), 0.68 (s, 9H). |
| 105 | 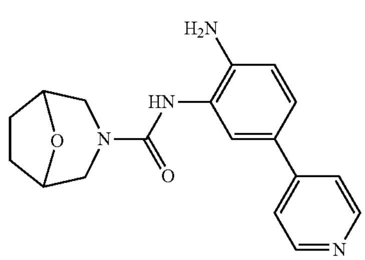 [SMILES: Nc1ccc(-c2ccncc2)cc1NC(=O)N1CC2CCC(C1)O2] | 324 | 325 | δ 8.50 (dd, J = 4.8 Hz, 1.6 Hz, 2H), 7.81 (s, 1H), 7.55 (dd, J = 4.4 Hz, 1.6 Hz, 2H), 7.49 (d, J = 2.0 Hz, 1H), 7.42-7.40 (m, 1H), 6.81 (d, J = 8.0 Hz, 1H), 5.19 (s, 2H), 4.34 (s, 2H), 3.71 (s, 1H), 3.68 (s, 1H), 3.05 (d, J = 2.0 Hz, 1H), 3.02 (d, J = 2.0 Hz, 2H), 1.79-1.77 (m, 4H). |

TABLE 1-continued

Exemplary Compounds

| No. | Structure | MS Calc. | MS found | ¹H NMR Data (400 MHz, DMSO-d₆) |
|---|---|---|---|---|
| 106 | 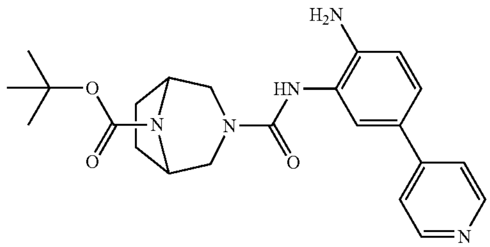 [SMILES: CC(C)(C)OC(=O)N1C2CCC1CN(C(=O)Nc1cc(-c3ccncc3)ccc1N)C2] | 423 | 424 | δ 8.49 (dd, J = 4.8 Hz, 1.6 Hz, 2H), 7.83 (s, 1H), 7.54 (dd, J = 4.8 Hz, 1.6 Hz, 2H), 7.48 (d, J = 2.0 Hz, 1H), 7.42 (dd, J = 8.4 Hz, 2.0 Hz, 1H), 6.81 (d, J = 8.0 Hz, 1H), 5.20 (s, 2H), 4.13 (s, 2H), 3.82 (d, J = 12.8 Hz, 2H), 3.00 (d, J = 13.2 Hz, 2H), 1.83 (br, 2H), 1.71 (d, J = 7.2 Hz, 2H), 1.43 (s, 9H). |
| 107 | 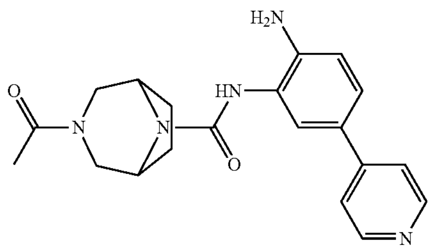 | 365 | 366 | δ 8.50 (dd, J = 4.4 Hz, 3.2 Hz, 2H), 8.12 (s, 1H), 7.56 (dd, J = 6.4 Hz, 3.2 Hz, 2H), 7.54 (d, J = 2.4 Hz, 1H), 7.42 (dd, J = 8.4 Hz, 2.0 Hz, 1H), 6.83 (d, J = 8.4 Hz, 1H), 5.20 (s, 2H), 4.41 (s, 2H), 4.09 (d, J = 12.8 Hz, 1H), 3.59 (d, J = 12.8 Hz, 1H), 3.38 (d, J = 12.0 Hz, 1H), 2.85 (d, J = 12.4 Hz, 1H), 2.04 (s, 1H), 4.09 (d, J = 12.8 Hz, 1H), 1.87 (t, J = 4.0 Hz, 2H), 1.71 (m, 1H), 1.52 (m, 1H). |
| 108 | 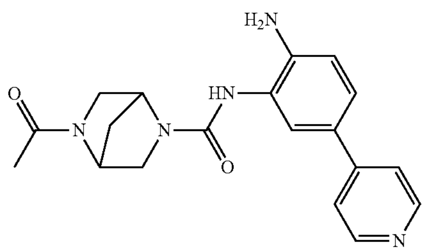 [SMILES: CC(=O)N1CC2CC1CN2C(=O)Nc1cc(-c2ccncc2)ccc1N] | 351 | 352 | δ 8.49 (d, J = 4.2 Hz, 2H), 7.74 (d, J = 10.8 1H), 7.56-7.54 (m, 3H), 7.43-7.40 (m, 1H), 6.81 (dd, J = 9.2 Hz, 1.2 Hz, 1H), 5.26 (d, J = 8.0 Hz, 2H), 4.71 (d, J = 10.0 Hz, 1H), 4.64 (d, J = 12.8 Hz, 1H), 3.51-3.27 (m, 5H), 1.90-1.76 (m, 4H). |
| 109 | 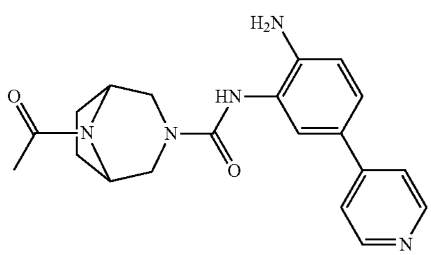 [SMILES: CC(=O)N1C2CCC1CN(C(=O)Nc1cc(-c3ccncc3)ccc1N)C2] | 365 | 366 | δ 8.50 (d, J = 6.4 Hz, 2H), 7.88 (br, 1H), 7.53 (d, J = 6.4 Hz, 2H), 7.48 (d, J = 2.0 Hz, 1H), 7.43 (dd, J = 8.4 Hz, 2.4 Hz, 1H), 6.81 (d, J = 8.4 Hz, 1H), 5.20 (br, 2H), 4.52 (d, J = 6.0 Hz, 1H), 4.30 (d, J = 6.8 Hz, 1H), 3.90-3.82 (m, 2H), 3.06-2.96 (m, 2H), 2.02 (s, 3H), 1.95-1.91 (m, 1H), 1..82-1.71 (m, 2H). |
| 110 | 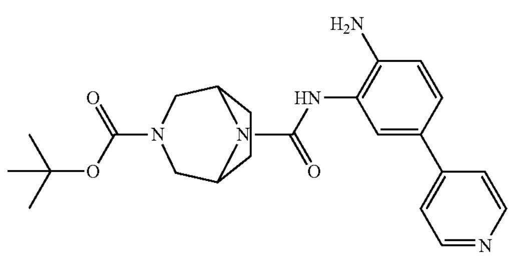 | 423 | 424 | δ 8.50 (d, J = 6.0 Hz, 2H), 8.09 (s, 1H), 7.55 (m, 3H), 7.42 (dd, J = 8.4 Hz, 2.0 Hz, 1H), 6.83 (d, J = 8.4 Hz, 1H), 5.21 (s, 2H), 4.38 (br, 2H), 3.74-3.63 (m, 2H), 3.14 (d, J = 12.4 Hz, 1H), 3.01 (d, J = 12.0 Hz, 1H), 1.87 (t, J = 4.0 Hz, 2H), 1.63-1.58 (m, 2H), 1.42 (s, 9H). |
| 111 | 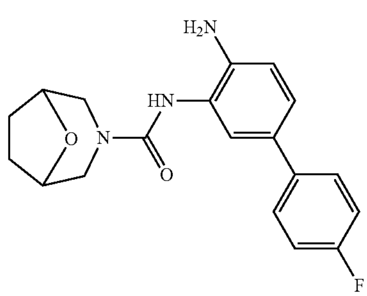 [SMILES: Nc1ccc(-c2ccc(F)cc2)cc1NC(=O)N1CC2CCC(C1)O2] | 341 | 342 | δ 7.78 (br, 1H), 7.55-7.52 (m, 2H), 7.31 (s, 1H), 7.19 (t, J = 8.0 Hz, 3H), 6.79 (d, J = 8.4 Hz, 1H), 4.91 (s, 2H), 4.33 (s, 2H), 3.71 (d, J = 12.4 Hz, 2H), 3.04 (d, J = 11.2 Hz, 2H), 1.82-1.76 (m, 4H). |

TABLE 1-continued

Exemplary Compounds

| No. | Structure | MS Calc. | MS found | ¹H NMR Data (400 MHz, DMSO-d₆) |
|---|---|---|---|---|
| 112 | 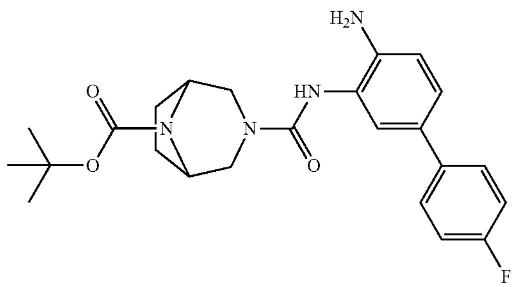 [SMILES: CC(C)(C)OC(=O)N1C2CCC1CN(C(=O)Nc1cc(-c3ccc(F)cc3)ccc1N)C2] | 440 | 441 | δ 7.83 (s, 1H), 7.55-7.52 (m, 2H), 7.30 (d, J = 2.0 Hz, 1H), 7.22-7.17 (m, 2H), 6.77 (d, J = 8.0 Hz, 1H), 4.94 (s, 2H), 4.13 (s, 2H), 3.82 (d, J = 12.0 Hz, 2H), 1.82 (s, 1H), 1.70 (d, J = 7.2 Hz, 2H), 1.43 (s, 9H). |
| 113 | 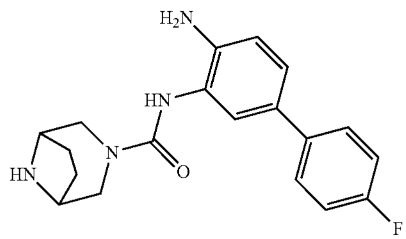 [SMILES: Nc1ccc(-c2ccc(F)cc2)cc1NC(=O)N1CC2CCC(C1)N2] | 340 | 341 | δ 7.70 (br, 1H), 7.55-7.52 (m, 2H), 7.30 (s, 1H), 7.22-7.16 (m, 3H), 6.78 (d, J = 8.4 Hz, 1H), 4.89 (br, 2H), 3.70 (d, J = 10.4 Hz, 2H), 3.37 (s, 2H), 2.94 (d, J = 11.2 Hz, 2H), 1.63 (s, 4H). |
| 114 | 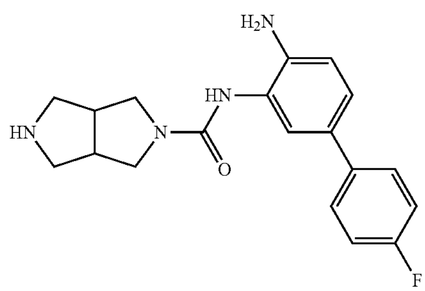 [SMILES: Nc1ccc(-c2ccc(F)cc2)cc1NC(=O)N1CC2CNCC2C1] | 340 | 341 | δ 7.56-7.52 (m, 3H), 7.35 (s, 1H), 7.22-7.17 (m, 3H), 6.78 (d, J = 8.0 Hz, 1H), 4.97 (br, 2H), 3.61 (t, J = 9.6 Hz, 2H), 3.20 (d, J = 10.8 Hz, 2H), 2.91-2.87 (m, 2H), 2.73 (s, 2H), 2.60 (d, J = 10 Hz, 2H). |
| 115 | 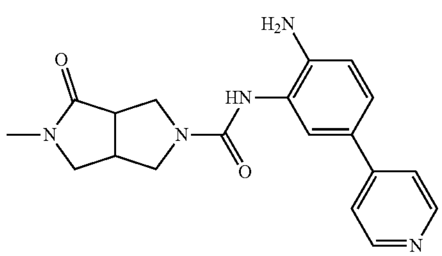 [SMILES: CN1CC2CN(C(=O)Nc3cc(-c4ccncc4)ccc3N)CC2C1=O] | 351 | 352 | δ 8.49 (d, J = 6.0 Hz, 2H), 7.65 (br, 1H), 7.55 (m, 3H), 7.41 (dd, J = 8.4 Hz, 2.0 Hz, 1H), 6.81 (d, J = 8.4 Hz, 1H), 5.25 (br, 2H), 3.83-3.73 (m, 2H), 3.59-3.50 (m, 2H), 3.18-3.06 (m, 3H), 3.02-2.97 (m, 1H), 2.76 (s, 3H). |
| 116 | 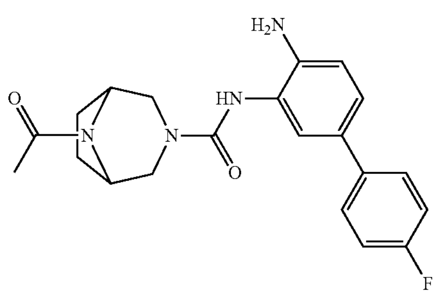 [SMILES: CC(=O)N1C2CCC1CN(C(=O)Nc1cc(-c3ccc(F)cc3)ccc1N)C2] | 382 | 383 | δ 7.87 (s, 1H), 7.56-7.52 (m, 2H), 7.29 (d, J = 1.6 Hz, 1H), 7.22-7.18 (m, 3H), 6.78 (d, J = 8.4 Hz, 1H), 4.93 (br, 2H), 4.51 (d, J = 4.0 Hz, 1H), 4.29 (d, J = 6.0 Hz, 1H), 3.91-3.82 (m, 2H), 3.05-2.95 (m, 2H), 2.02 (s, 3H), 1.94-1.89 (m, 1H), 1.81-1.69 (m, 3H). |

TABLE 1-continued

Exemplary Compounds

| No. | Structure | MS Calc. | MS found | ¹H NMR Data (400 MHz, DMSO-d₆) |
|---|---|---|---|---|
| 117 | 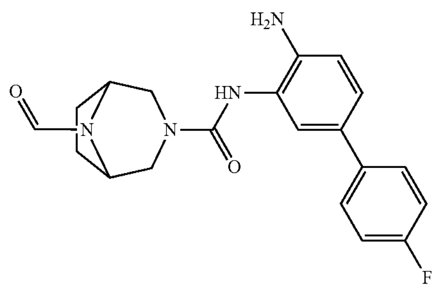 [SMILES: Nc1ccc(-c2ccc(F)cc2)cc1NC(=O)N1CC2CCC(C1)N2C=O] | 368 | 369 | δ 8.14 (s, 1H), 7.88 (s, 1H), 7.56-7.52 (m, 2H), 7.29 (d, J = 2.0 Hz, 1H), 7.22-7.18 (m, 3H), 6.78 (d, J = 8.4 Hz, 1H), 4.94 (br, 2H), 4.47 (s, 1H), 4.25 (d, J = 5.6 Hz, 1H), 3.98-3.91 (m, 2H), 3.02-2.93 (m, 2H), 1.88-1.75 (m, 4H). |
| 118 | 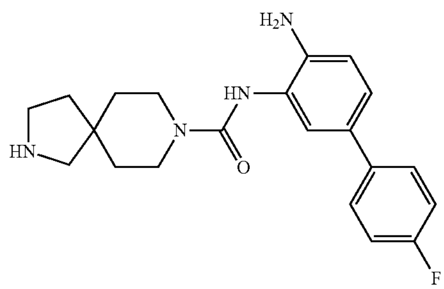 [SMILES: Nc1ccc(-c2ccc(F)cc2)cc1NC(=O)N1CCC2(CCNC2)CC1] | 368 | 369 | CD₃OD δ 7.45-7.42 (m, 2H), 7.18-7.13 (m, 2H), 6.99 (t, J = 8.8 Hz, 2H), 6.80 (d, J = 8.0 Hz, 1H), 3.51-3.46 (m, 2H), 3.43-3.38 (m, 2H), 2.90-2.86 (m, 2H), 2.65-2.64 (m, 2H), 1.63-1.60 (m, 2H), 1.53-1.50 (m, 4H). |
| 119 | 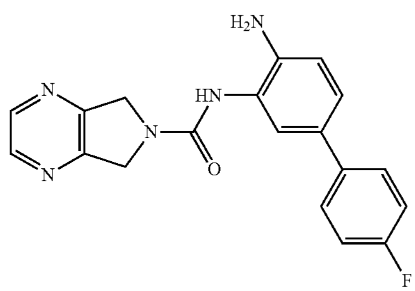 [SMILES: Nc1ccc(-c2ccc(F)cc2)cc1NC(=O)N1Cc2nccnc2C1] | 349 | 350 | δ 8.55 (s, 2H), 7.91 (s, 1H), 7.57-7.54 (m, 2H), 7.40 (d, J = 2.0 Hz, 1H), 7.25-7.21 (m, 3H), 6.81 (d, J = 8.0 Hz, 1H), 5.11 (br, 2H), 4.83 (s, 4H). |
| 120 | 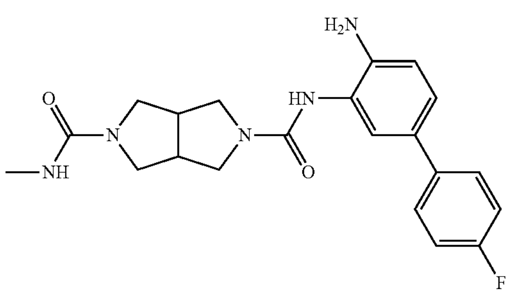 [SMILES: CNC(=O)N1CC2CN(C(=O)Nc3cc(-c4ccc(F)cc4)ccc3N)CC2C1] | 397 | 398 | δ 7.56-7.51 (m, 3H), 7.36 (d, J = 2.0 Hz, 1H), 7.22-7.17 (m, 3H), 6.77 (d, J = 8.4 Hz, 1H), 6.08 (d, J = 4.4 Hz, 1H), 5.00 (br, 2H), 3.66-3.561 (m, 2H), 3.49-3.45 (m, 2H), 3.27-3.24 (m, 2H), 3.16-3.13 (m, 2H), 2.90 (s, 2H), 2.56 (d, J = 4.4 Hz, 3H). |
| 121 | 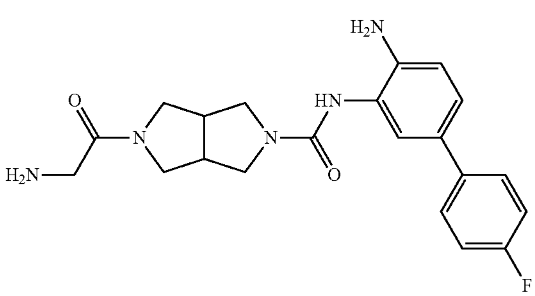 [SMILES: NCC(=O)N1CC2CN(C(=O)Nc3cc(-c4ccc(F)cc4)ccc3N)CC2C1] | 397 | 398 | δ 7.55-7.52 (m, 3H), 7.36 (d, J = 2.0 Hz, 1H), 7.22-7.17 (m, 3H), 6.78 (d, J = 8.0 Hz, 1H), 5.00 (br, 2H), 3.68-3.56 (m, 4H), 3.32-3.26 (m, 8H), 3.02-2.95 (m, 1H), 2.93-2.85 (m, 1H). |

TABLE 1-continued

Exemplary Compounds

| No. | Structure | MS Calc. | MS found | ¹H NMR Data (400 MHz, DMSO-d₆) |
|---|---|---|---|---|
| 122 | 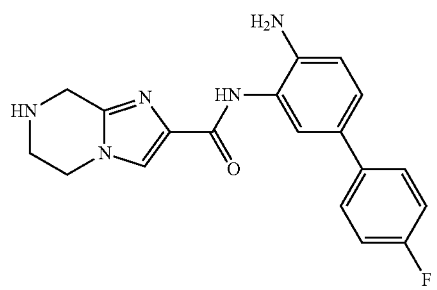 [SMILES: Nc1ccc(-c2ccc(F)cc2)cc1NC(=O)c1cn2c(n1)CNCC2] | 351 | 352 | δ 9.32 (br, 1H), 7.73 (d, J = 2.0 Hz, 1H), 7.69 (s, 1H), 7.58-7.54 (m, 2H), 7.24-7.20 (m, 3H), 6.86 (d, J = 8.4 Hz, 1H), 4.98 (br, 2H), 3.97 (t, J = 7.2 Hz, 2H), 3.90 (s, 2H), 3.06 (s, 2H), 2.80 (br, 1H). |
| 123 | 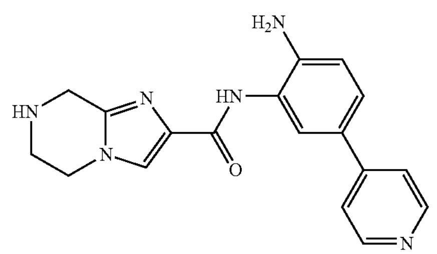 [SMILES: Nc1ccc(-c2ccncc2)cc1NC(=O)c1cn2c(n1)CNCC2] | 334 | 335 | δ 9.35 (br, 1H), 8.52 (d, J = 5.2 Hz, 2H), 7.87 (d, J = 1.2 Hz, 1H), 7.70 (s, 1H), 7.56 (d, J = 5.6 Hz, 2H), 7.44 (d, J = 8.4 Hz, 1H), 6.89 (d, J = 8.0 Hz, 1H), 5.25 (br, 2H), 3.98-3.90 (m, 4H), 3.07 (d, J = 5.6 Hz, 2H), 2.83-2.80 (m, 1H). |
| 124 | 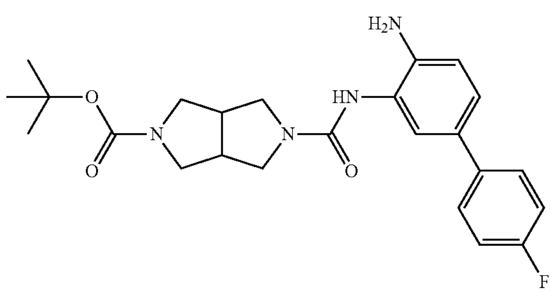 [SMILES: CC(C)(C)OC(=O)N1CC2CN(C(=O)Nc3cc(-c4ccc(F)cc4)ccc3N)CC2C1] | 440 | 441 | δ 7.55-7.52 (m, 2H), 7.49 (s, 1H), 7.36 (d, J = 2.0 Hz, 1H), 7.22-7.17 (m, 3H), 6.77 (d, J = 8.4 Hz, 1H), 5.00 (br, 2H), 3.65-3.59 (m, 2H), 3.53-3.47 (m, 2H), 3.27 (s, 2H), 3.18-3.14 (m, 2H), 2.90 (s, 2H), 1.41 (s, 9H). |
| 125 | 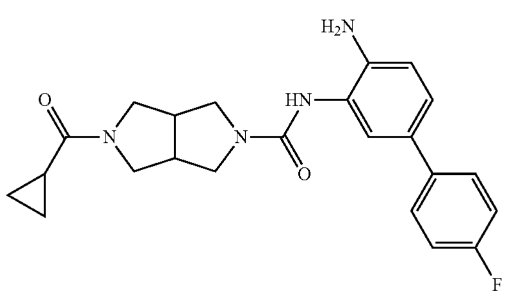 [SMILES: Nc1ccc(-c2ccc(F)cc2)cc1NC(=O)N1CC2CN(C(=O)C3CC3)CC2C1] | 408 | 409 | δ 7.55-7.51 (m, 3H), 7.37 (d, J = 2.0 Hz, 1H), 7.22-7.17 (m, 3H), 6.78 (d, J = 8.4 Hz, 1H), 5.00 (br, 2H), 3.92-3.87 (m, 1H), 3.69-3.63 (m, 2H), 3.59-3.53 (m, 2H), 3.31-3.24 (m, 3H), 3.06-2.99 (m, 1H), 2.94-2.86 (m, 1H), 1.79-1.73 (m, 1H), 0.75-0.71 (m, 4H). |
| 126 | 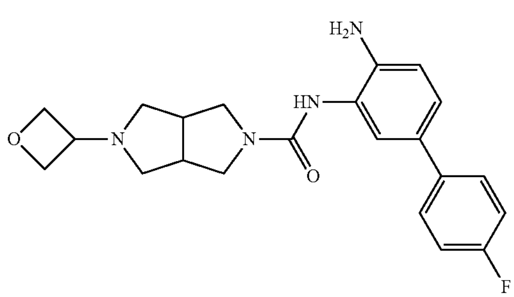 [SMILES: Nc1ccc(-c2ccc(F)cc2)cc1NC(=O)N1CC2CN(C3COC3)CC2C1] | 396 | 397 | δ 7.58-7.52 (m, 3H), 7.36 (d, J = 2.4 Hz, 1H), 7.22-7.17 (m, 3H), 6.78 (d, J = 8.4 Hz, 1H), 4.97 (br, 2H), 4.57 (t, J = 6.8 Hz, 2H), 4.45 (t, J = 5.6 Hz, 2H), 3.67-3.62 (m, 2H), 3.58-3.52 (m, 1H), 3.28 (dd, J = 10.8 Hz, 3.6 Hz, , 2H), 2.85-2.81 (m, 2H), 2.51-2.50 (m, 2H), 2.44-2.41 (m, 2H). |

TABLE 1-continued

Exemplary Compounds

| No. | Structure | MS Calc. | MS found | ¹H NMR Data (400 MHz, DMSO-d₆) |
|---|---|---|---|---|
| 127 | 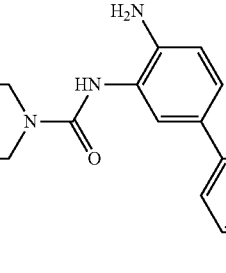 | 355 | 356 | δ 7.94 (s, 1H), 7.55-7.52 (m, 2H), 7.27 (d, J = 2.0 Hz, 1H), 7.20 (t, J = 8.8 Hz, 3H), 6.78 (d, J = 8.4 Hz, 1H), 4.89 (br, 2H), 4.34 (s, 4H), 3.37 (t, J = 5.6 Hz, 4H), 1.78 (t, J = 5.6 Hz, 4H), . |
| 128 | 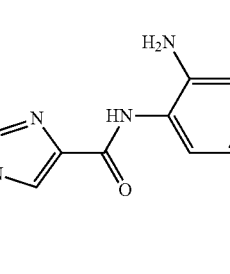 | 375 | 376 | CD₃OD δ 7.60 (s, 1H), 7.55 (d, J = 2.0 Hz, 1H), 7.48-7.44 (m, 2H), 7.19 (dd, J = 8.4 Hz, 2.4 Hz, 1H), 7.00 (t, J = 8.4 Hz, 2H), 6.85 (d, J = 8.0 Hz, 1H), 4.27 (d, J = 5.2 Hz, 2H), 3.51-3.47 (m, 1H), 2.97-2.96 (m, 2H), 2.23-2.22 (m, 2H). |
| 129 | 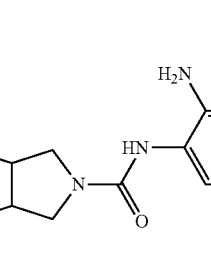 | 379 | 380 | δ 8.50-8.49 (m, 2H), 7.60 (s, 1H), 7.56-7.54 (m, 3H), 7.40 (dd, J = 8.4 Hz, 2.4 Hz, , 1H), 6.82 (d, J = 8.4 Hz, 1H), 5.25 (br, 2H), 4.57 (t, J = 6.4 Hz, 2H), 4.46 (t, J = 6.0 Hz, 2H), 3.68-3.63 (m, 2H), 3.58-3.52 (m, 1H), 3.28 (dd, J = 10.4 Hz, 3.2 Hz, 2H), 2.89-2.80 (m, 2H), 2.51-2.48 (m, 2H), 2.44-2.42 (m, 2H). |
| 130 | 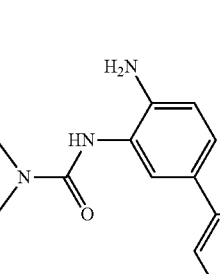 | 364 | 365 | δ 8.70 (s, 1H), 8.59 (d, J = 5.2 Hz, 1H), 7.89 (s, 1H), 7.65 (d, J = 8.8 Hz, 2H), 7.53-7.50 (m, 4H), 7.34 (d, J = 2.0 Hz, 1H), 6.90 (d, J = 8.4 Hz, 1H), 5.24 (br, 2H), 4.91 (d, J = 6.4 Hz, 4H). |
| 131 | 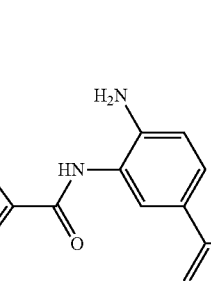 | 369 | 370 | δ 9.32 (br, 1H), 7.74 (d, J = 2.0 Hz, 1H), 7.69 (s, 1H), 7.61-7.55 (m, 1H), 7.45-7.38 (m, 2H), 7.27 (dd, J = 8.4 Hz, 2.0 Hz, 1H), 6.86 (d, J = 8.0 Hz, 1H), 5.07 (br, 2H), 3.97 (t, J = 5.2 Hz, 2H), 3.91 (d, J = 5.2 Hz, 2H), 3.07 (d, J = 5.2 Hz, 2H), 2.82-2.80 (m, 1H). |

TABLE 1-continued

Exemplary Compounds

| No. | Structure | MS Calc. | MS found | ¹H NMR Data (400 MHz, DMSO-d₆) |
|---|---|---|---|---|
| 132 | 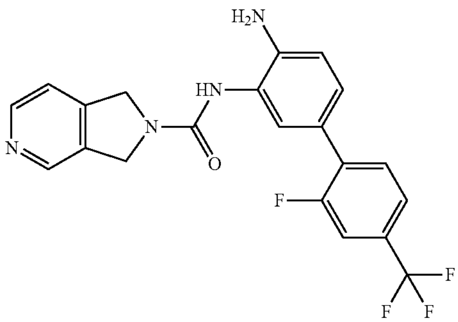 [SMILES: Nc1ccc(-c2ccc(C(F)(F)F)cc2F)cc1NC(=O)N1Cc2ccncc2C1] | 416 | 417 | CD₃OD δ 8.59 (s, 1H), 8.51 (d, J = 5.2 Hz, 1H), 7.69 (t, J = 7.6 Hz,, 1H), 7.54-7.49 (m, 3H), 7.47 (s, 1H), 7.35-7.32 (m, 1H), 6.96 (d, J = 8.4 Hz, 1H), 4.94 (d, J = 5.2 Hz, 4H) |
| 133 | 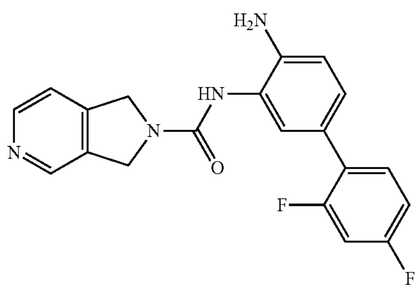 [SMILES: Nc1ccc(-c2ccc(F)cc2F)cc1NC(=O)N1Cc2ccncc2C1] | 366 | 367 | CD₃OD δ 8.59 (s, 1H), 8.50 (d, J = 5.2 Hz, 1H), 7.49-7.47 (m, 2H), 7.33-7.32 (m, 1H), 7.23-7.21 (m, 1H), 7.02-6.98 (m, 2H), 6.94 (d, J = 8.4 Hz, 1H), 4.92-4.90 (m, 4H) |
| 134 | 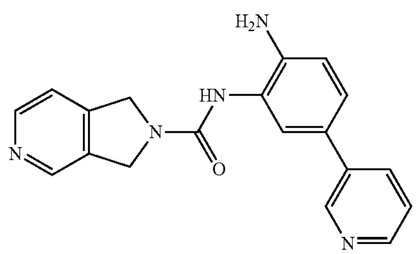 [SMILES: Nc1ccc(-c2cccnc2)cc1NC(=O)N1Cc2ccncc2C1] | 331 | 332 | CD₃OD δ 8.76 (d, J = 1.6 Hz, 1H), 8.60 (s, 1H), 8.51 (d, J = 5.2 Hz, 1H), 8.42 (dd, J = 4.8 Hz, 1.2 Hz, 1H), 8.07-8.04 (m, 1H), 7.51-7.46 (m, 3H), 7.39 (dd, J = 8.4 Hz, 2.4 Hz, 1H), 6.99 (d, J = 8.4 Hz, 1H), 4.95 (d, J = 8.4 Hz, 4H). |
| 135 | 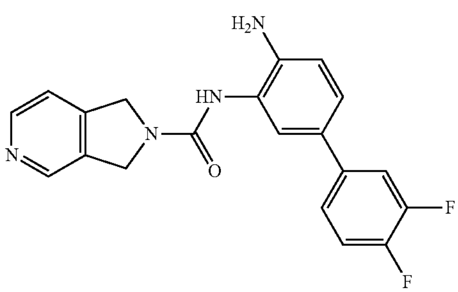 [SMILES: Nc1ccc(-c2ccc(F)c(F)c2)cc1NC(=O)N1Cc2ccncc2C1] | 366 | 367 | CD₃OD δ 8.60 (s, 1H), 8.51 (d, J = 5.2 Hz, 1H), 7.51-7.49 (m, 2H), 7.41 (d, J = 2.0 Hz, 1H), 7.36-7.34 (m, 1H), 7.33-7.26 (m, 2H), 6.94 (d, J = 8.4 Hz, 1H), 4.94 (d, J = 5.2 Hz, 4H) |
| 136 | 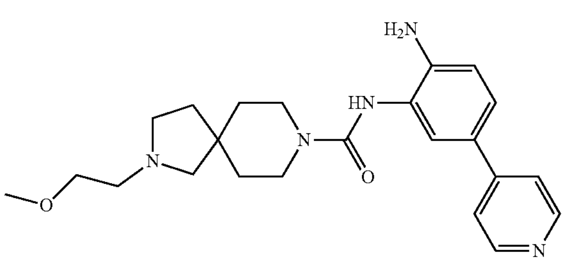 [SMILES: COCCN1CCC2(CCN(C(=O)Nc3cc(-c4ccncc4)ccc3N)CC2)C1] | 409 | 410 | δ 8.49 (d, J = 5.6 Hz, 2H), 7.91 (s, 1H), 7.54 (d, J = 5.6 Hz, 2H), 7.47 (s, 1H), 7.39 (d, J = 8.4 Hz, 1H), 6.81 (d, J = 8.4 Hz, 1H), 5.15 (br, 2H), 3.49-3.35 (m, 6H), 3.24 (s, 3H), 2.56-2.52 (m, 4H), 2.39 (s, 2H), 1.58 (t, J = 6.8 Hz, 2H), 1.51-1.44 (m, 4H). |

TABLE 1-continued

Exemplary Compounds

| No. | Structure | MS Calc. | MS found | ¹H NMR Data (400 MHz, DMSO-d₆) |
|---|---|---|---|---|
| 137 | 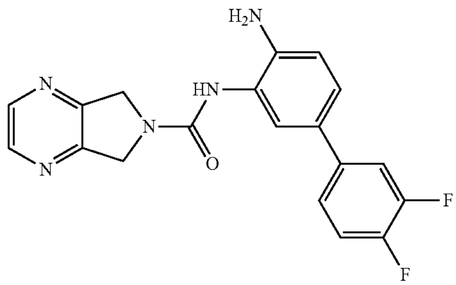 [SMILES: Nc1ccc(-c2ccc(F)c(F)c2)cc1NC(=O)N1Cc2nccnc2C1] | 367 | 368 | δ 8.56 (s, 2H), 7.91-7.86 (m, 1H), 7.60-7.54 (m, 1H), 7.60-7.36 (m, 3H), 7.29 (dd, J = 8.0 Hz, 2.0 Hz, 1H), 6.81 (d, J = 8.4 Hz, 1H), 5.20 (br, 2H), 4.84 (s, 4H). |
| 138 | 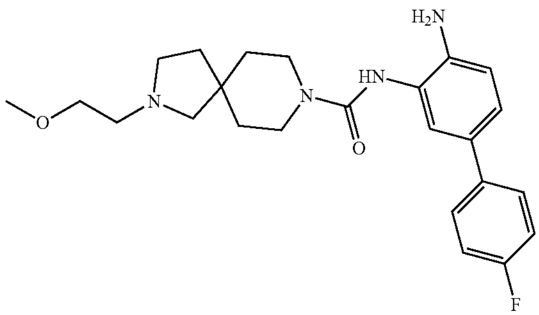 [SMILES: COCCN1CCC2(CCN(C(=O)Nc3cc(-c4ccc(F)cc4)ccc3N)CC2)C1] | 426 | 427 | δ 7.91 (s, 1H), 7.56-7.52 (m, 2H), 7.28 (d, J = 2.0 Hz, 1H), 7.22-7.17 (m, 3H), 6.77 (d, J = 8.4 Hz, 1H), 4.90 (br, 2H), 3.47-3.38 (m, 6H), 3.25-3.23 (m, 4H), 2.56-2.40 (m, 5H), 1.60-1.49 (m, 6H). |
| 139 | 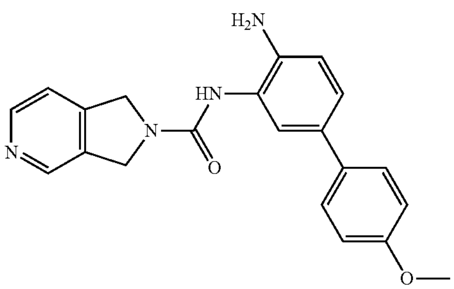 [SMILES: COc1ccc(-c2ccc(N)c(NC(=O)N3Cc4ccncc4C3)c2)cc1] | 360 | 361 | δ 8.62 (s, 1H), 8.50 (d, J = 5.2 Hz, 1H), 7.79 (s, 1H), 7.47-7.43 (m, 3H), 7.37 (d, J = 2.0 Hz, 1H), 7.18 (dd, J = 8.4 Hz, 2.4 Hz, 1H), 6.96 (d, J = 8.8 Hz, 2H), 6.78 (d, J = 8.4 Hz, 1H), 4.99 (br, 2H), 4.82 (d, J = 6.0 Hz, 4H), 3.77 (s, 3H). |
| 140 | 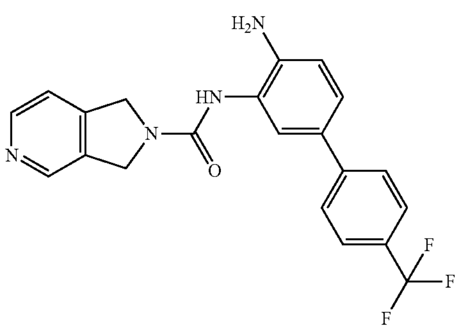 [SMILES: Nc1ccc(-c2ccc(C(F)(F)F)cc2)cc1NC(=O)N1Cc2ccncc2C1] | 398 | 399 | δ 8.62 (s, 1H), 8.51 (d, J = 4.8 Hz, 1H), 7.82 (s, 1H), 7.74 (m, 4H), 7.52 (d, J = 2.0 Hz, 1H), 7.45 (d, J = 4.8 Hz, 1H), 7.36 (dd, J = 8.4 Hz, 2.0 Hz, 1H), 6.83 (d, J = 8.4 Hz, 1H), 5.27 (br, 2H), 4.83 (d, J = 5.6 Hz, 4H) |
| 141 | 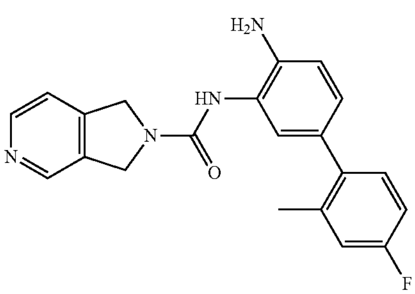 [SMILES: Cc1cc(F)ccc1-c1ccc(N)c(NC(=O)N2Cc3ccncc3C2)c1] | 362 | 363 | CD₃OD<br>δ 8.59 (s, 1H), 8.50 (d, J = 5.2 Hz, 1H), 7.49 (d, J = 4.8 Hz, 1H), 7.20-7.18 (m, 1H), 7.10 (d, J = 2.0 Hz, 1H), 7.00-6.98 (m, 2H), 6.94-6.92 (m, 2H), 4.93 (d, J = 5.2 Hz, 4H), 2.30 (s, 3H). |

TABLE 1-continued

Exemplary Compounds

| No. | Structure | MS Calc. | MS found | ¹H NMR Data (400 MHz, DMSO-d₆) |
|---|---|---|---|---|
| 142 | 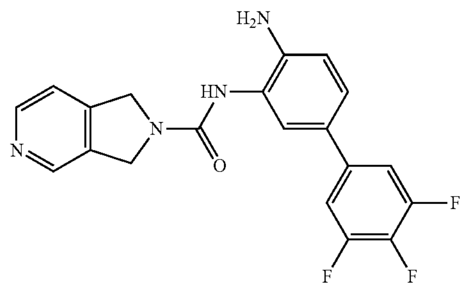 [SMILES: Nc1ccc(-c2cc(F)c(F)c(F)c2)cc1NC(=O)N1Cc2ccncc2C1] | 384 | 385 | CD₃OD<br>δ 8.60 (s, 1H), 8.51 (d, J = 4.8 Hz, 1H), 7.51 (d, J = 4.8 Hz, 1H), 7.42 (d, J = 2.0 Hz, 1H), 7.36-7.32 (m, 3H), 6.94 (d, J = 8.4 Hz, 1H), 4.95 (d, J = 6.0 Hz, 4H) |
| 143 | 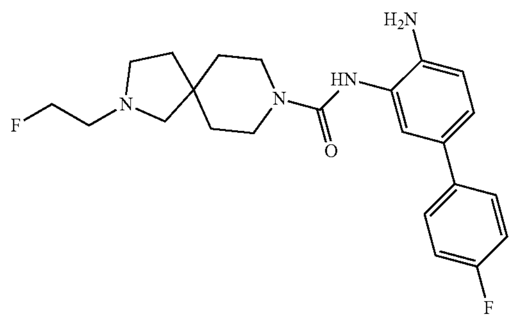 [SMILES: Nc1ccc(-c2ccc(F)cc2)cc1NC(=O)N1CCC2(CCN(CCF)C2)CC1] | 414 | 415 | δ 7.91 (s, 1H), 7.56-7.52 (m, 2H), 7.28 (d, J = 2.4 Hz, 1H), 7.22-7.17 (m, 3H), 6.77 (d, J = 8.0 Hz, 1H), 4.90 (br, 2H), 4.57 (t, J = 4.8 Hz, 1H), 4.45 (t, J = 4.8 Hz, 1H), 3.48-3.42 (m, 2H), 3.39-3.36 (m, 2H), 2.71 (t, J = 4.8 Hz, 1H), 2.64 (t, J = 5.2 Hz, 1H), 2.58 (t, J = 6.8 Hz, 2H), 2.43 (s, 2H), 1.60 (t, J = 6.8 Hz, 2H), 1.52-1.48 (m, 4H). |
| 144 | 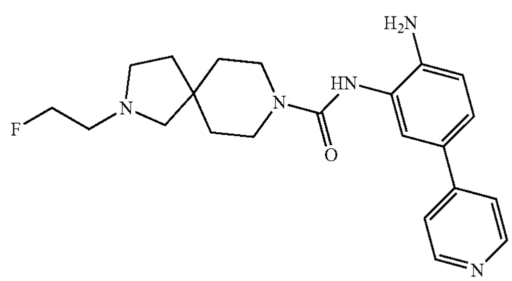 [SMILES: Nc1ccc(-c2ccncc2)cc1NC(=O)N1CCC2(CCN(CCF)C2)CC1] | 397 | 398 | δ 8.50 (m, 2H), 7.92 (s, 1H), 7.54 (m, 2H), 7.47 (d, J = 2.0 Hz, 1H), 7.40 (dd, J = 8.0 Hz, 2.4 Hz, 1H), 6.80 (d, J = 8.4 Hz, 1H), 5.16 (br, 2H), 4.57 (t, J = 4.8 Hz, 1H), 4.45 (t, J = 4.8 Hz, 1H), 3.49-3.43 (m, 2H), 3.39-3.36 (m, 2H), 2.73 (t, J = 4.8 Hz, 1H), 2.66 (t, J = 5.2 Hz, 1H), 2.60 (t, J = 6.8 Hz, 2H), 2.43 (s, 2H), 1.61 (t, J = 6.8 Hz, 2H), 1.53-1.49 (m, 4H). |
| 145 | 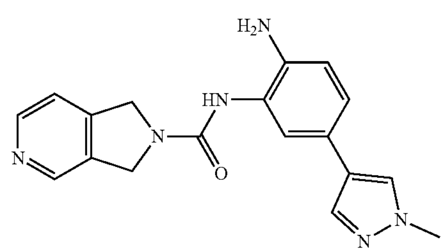 [SMILES: Cn1cc(-c2ccc(N)c(NC(=O)N3Cc4ccncc4C3)c2)cn1] | 334 | 335 | δ 8.61 (s, 1H), 8.50 (d, J = 4.8 Hz, 1H), 7.88 (s, 1H), 7.77 (s, 1H), 7.63 (s, 1H), 7.44 (d, J = 5.2 Hz, 1H), 7.27 (d, J = 2.0 Hz, 1H), 7.11 (dd, J = 8.0 Hz, 2.0 Hz, 1H), .6.71 (d, J = 8.4 Hz, 1H), 4.88 (br, 2H), 4.81 (d, J = 6.0 Hz, 4H), 3.82 (s, 3H). |
| 146 | 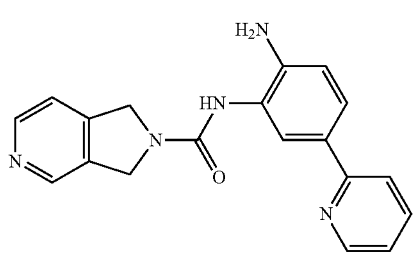 [SMILES: Nc1ccc(-c2ccccn2)cc1NC(=O)N1Cc2ccncc2C1] | 331 | 332 | CD₃OD<br>δ 8.79 (s, 1H), 8.70 (t, J = 4.8 Hz, 2H), 8.02-8.00 (m, 1H), 7.97-7.93 (m, 2H), 7.86 (dd, J = 8.4 Hz, 2.0 Hz, 1H), 7.69 (d, J = 5.2 Hz, 1H), 7.46-7.45 (m, 1H), 7.14 (d, J = 8.4 Hz, 1H), 5.13 (d, J = 6.4 Hz, 4H). |

TABLE 1-continued

Exemplary Compounds

| No. | Structure | MS Calc. | MS found | ¹H NMR Data (400 MHz, DMSO-d₆) |
|---|---|---|---|---|
| 147 | 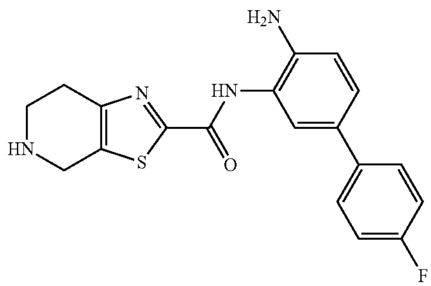 [SMILES: Nc1ccc(-c2ccc(F)cc2)cc1NC(=O)c1nc2c(s1)CNCC2] | 368 | 369 | CD₃OD<br>δ 7.64 (d, J = 2.0 Hz, 1H), 7.60-7.56 (m, 2H), 7.34 (dd, J = 8.4 Hz, 2.0 Hz, 1H), 7.13 (t, J = 8.8 Hz, 2H), 6.98 (d, J = 8.0 Hz, 1H), 4.12 (s, 2H), 3.19 (t, J = 5.6 Hz, 2H), 2.95 (t, J = 5.6 Hz, 2H). |
| 148 | 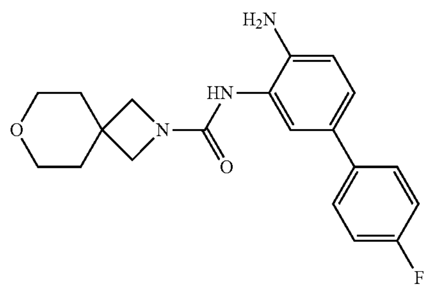 [SMILES: Nc1ccc(-c2ccc(F)cc2)cc1NC(=O)N1CC2(CCOCC2)C1] | 355 | 356 | δ 7.66 (s, 1H), 7.54-7.50 (m, 2H), 7.38 (d, J = 2.0 Hz, 1H), 7.22-7.17 (m, 3H), 6.76 (d, J = 8.0 Hz, 1H), 5.00 (br, 2H), 3.70 (s, 4H), 3.52 (t, J = 5.2 Hz, 4H), 1.70 (t, J = 5.2 Hz, 4H). |
| 149 | 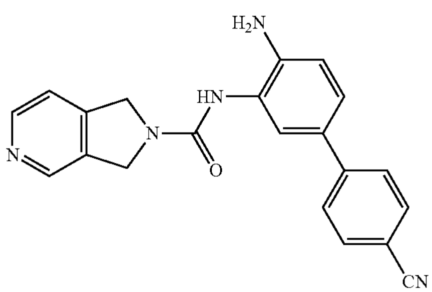 [SMILES: N#Cc1ccc(-c2ccc(N)c(NC(=O)N3Cc4ccncc4C3)c2)cc1] | 355 | 356 | δ 8.62 (s, 1H), 8.51 (d, J = 4.8 Hz, 1H), 7.82-7.80 (m, 3H), 7.75-7.74 (m, 2H), 7.54 (d, J = 2.0 Hz, 1H), 7.45 (d, J = 4.8 Hz, 1H), 7.38 (dd, J = 8.0 Hz, 2.4 Hz, 1H), 6.82 (d, J = 8.4 Hz, 1H), 5.34 (br, 2H), 4.83 (d, J = 6.8 Hz, 4H). |
| 150 | 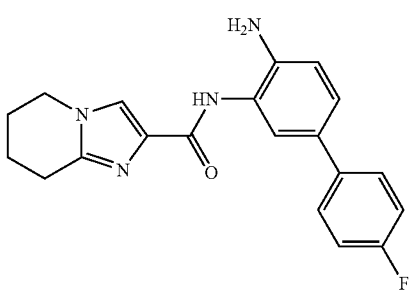 [SMILES: Nc1ccc(-c2ccc(F)cc2)cc1NC(=O)c1cn2c(n1)CCCC2] | 350 | 351 | δ 9.31 (br, 1H), 7.73 (d, J = 2.0 Hz, 1H), 7.65 (s, 1H), 7.58-7.54 (m, 2H), 7.24-7.20 (m, 3H), 6.86 (t, J = 8.0 Hz, 1H), 4.98 (br, 2H), 4.02 (t, J = 5.6 Hz, 2H), 2.80 (t, J = 5.6 Hz, 2H), 1.91-1.88 (m, 4H). |
| 151 | 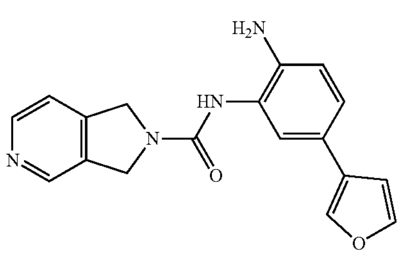 [SMILES: Nc1ccc(-c2ccoc2)cc1NC(=O)N1Cc2ccncc2C1] | 320 | 321 | δ 8.61 (s, 1H), 8.50 (d, J = 5.2 Hz, 1H), 7.93 (s, 1H), 7.79 (s, 1H), 7.66 (t, J = 1.8 Hz, 1H), 7.44 (d, J = 4.8 Hz, 1H), 7.30 (d, J = 2.0 Hz, 1H), 7.17 (dd, J = 8.0 Hz, 2.0 Hz, 1H), 6.78 (s, 1H), 6.73 (d, J = 8.4 Hz, 1H), 4.98 (br, 2H), 4.81 (d, J = 6.4 Hz, 4H). |

TABLE 1-continued

Exemplary Compounds

| No. | Structure | MS Calc. | MS found | ¹H NMR Data (400 MHz, DMSO-d$_6$) |
|---|---|---|---|---|
| 152 | 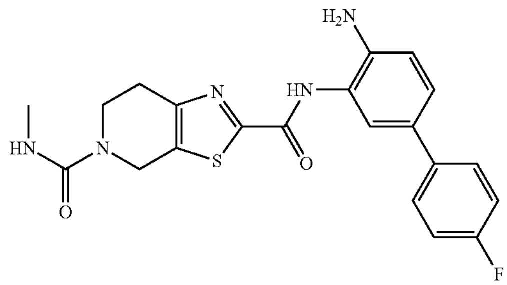 [SMILES: CNC(=O)N1CCc2nc(C(=O)Nc3cc(-c4ccc(F)cc4)ccc3N)sc2C1] | 425 | 426 | δ 10.05 (br, 1H), 7.58-7.55 (m, 3H), 7.30 (d, J = 8.4 Hz, 1H), 7.22 (t, J = 8.8 Hz, 2H), 6.86 (d, J = 8.4 Hz, 1H), 6.73 (d, J = 4.0 Hz, 1H), 5.13 (br, 2H), 4.69 (s, 2H), 3.71 (t, J = 5.2 Hz, 2H), 2.88 (s, 2H), 2.60 (d, J = 4.0 Hz, 3H). |
| 153 | 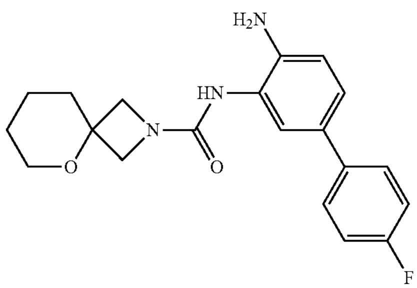 [SMILES: Nc1ccc(-c2ccc(F)cc2)cc1NC(=O)N1CC2(CCCCO2)C1] | 355 | 356 | δ 7.74 (s, 1H), 7.54-7.51 (m, 2H), 7.37 (d, J = 2.0 Hz, 1H), 7.22-7.17 (m, 3H), 6.76 (d, J = 8.0 Hz, 1H), 5.01 (br, 2H), 3.80 (s, 4H), 3.57 (t, J = 5.2 Hz, 2H), 1.70 (m, 2H), 1.61-1.55 (m, 2H), 1.46 (m, 2H). |
| 154 | 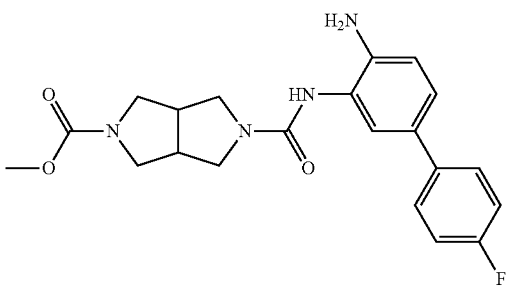 [SMILES: COC(=O)N1CC2CN(C(=O)Nc3cc(-c4ccc(F)cc4)ccc3N)CC2C1] | 398 | 399 | 7.55-7.50 (m, 3H), 7.36 (d, J = 2.0 Hz, 1H), 7.22-7.17 (m, 3H), 6.77 (d, J = 8.0 Hz, 1H), 5.00 (br, 2H), 3.65-3.54 (m, 7H), 3.28 (dd, J = 10.4 Hz, 4.0 Hz, 2H), 3.23-3.19 (dd, J = 10.4 Hz, 4.0 Hz, 2H), 2.93 (m, 2H). |
| 155 | 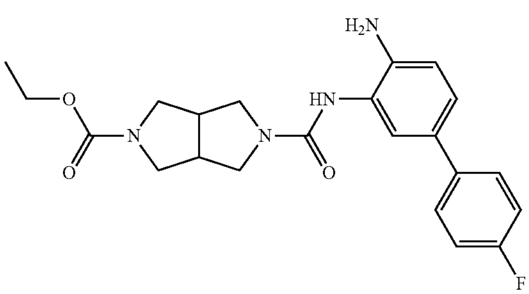 [SMILES: CCOC(=O)N1CC2CN(C(=O)Nc3cc(-c4ccc(F)cc4)ccc3N)CC2C1] | 412 | 413 | 7.55-7.50 (m, 3H), 7.36 (d, J = 2.0 Hz, 1H), 7.22-7.17 (m, 3H), 6.77 (d, J = 8.0 Hz, 1H), 5.00 (br, 2H), 4.03 (m, 2H), 3.62 (m, 2H), 3.54 (m, 2H), 3.28 (dd, J = 10.4 Hz, 4.0 Hz, 2H), 3.21 (dd, J = 10.4 Hz, 4.0 Hz, 2H), 2.92 (m, 2H), 1.85 (t, J = 7.2 Hz, 3H). |
| 156 | 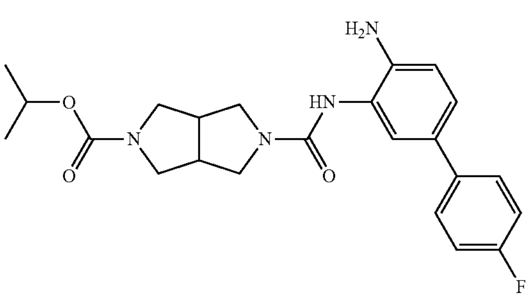 [SMILES: CC(C)OC(=O)N1CC2CN(C(=O)Nc3cc(-c4ccc(F)cc4)ccc3N)CC2C1] | 426 | 427 | 7.55-7.49 (m, 3H), 7.36 (d, J = 2.0 Hz, 1H), 7.22-7.17 (m, 3H), 6.77 (d, J = 8.0 Hz, 1H), 5.00 (br, 2H), 4.76 (m, 1H), 3.61 (m, 2H), 3.54 (m, 2H), 3.30-3.26 (m, 2H), 3.21-3.17 (m, 2H), 2.91 (m, 2H), 1.19 (d, J = 6.0 Hz, 6H). |

TABLE 1-continued
Exemplary Compounds
| No. | Structure | MS Calc. | MS found | ¹H NMR Data (400 MHz, DMSO-d₆) |
|---|---|---|---|---|
| 157 | 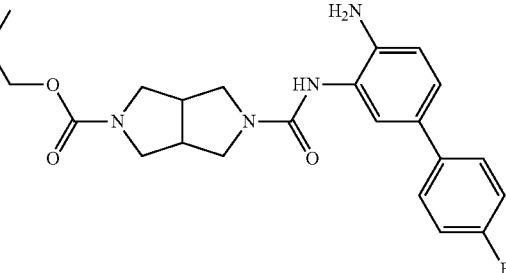 | 440 | 441 | 7.55-7.50 (m, 3H), 7.36 (d, J = 2.0 Hz, 1H), 7.22-7.17 (m, 3H), 6.77 (d, J = 8.0 Hz, 1H), 5.00 (br, 2H), 3.77 (d, J = 5.6 Hz, 2H), 3.64-3.54 (m, 4H), 3.30-3.26 (m, 2H), 3.23-3.17 (m, 2H), 2.93 (m, 2H), 1.88-1.85 (m, 1H), 0.89 (d, J = 6.8 Hz, 6H). |
| 158 | 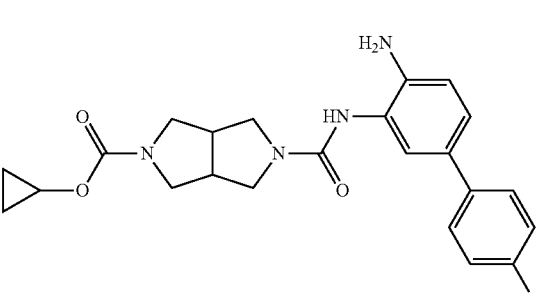 | 424 | 425 | δ 7.55-7.50 (m, 3H), 7.35 (d, J = 2.0 Hz, 1H), 7.22-7.17 (m, 3H), 6.77 (d, J = 8.0 Hz, 1H), 5.00 (s, 2H), 3.98-3.95 (m, 1H), 3.65-3.47 (m 4H), 3.29-3.12 (m, 4H), 2.90 (br, 2H), 0.64-0.61 (m, 4H). |
| 159 | 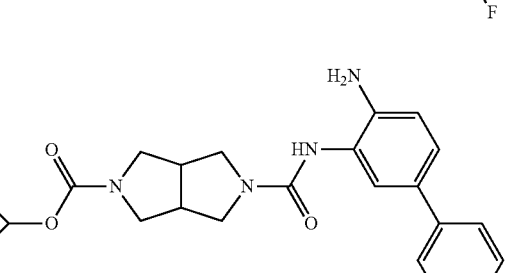 | 438 | 439 | δ 7.55-7.50 (m, 3H), 7.36 (d, J = 1.6 Hz, 1H), 7.22-7.17 (m, 3H), 6.77 (d, J = 8.4 Hz, 1H), 5.01 (s, 2H), 4.85-4.81 (m, 1H), 3.65-3.49 (m, 4H), 3.30-3.28 (m, 4H), 2.91 (br, 2H), 2.27-2.20 (m, 2H), 2.01-1.96 (m, 2H), 1.71-1.69 (m, 1H), 1.58-1.53 (m, 1H). |
| 160 | 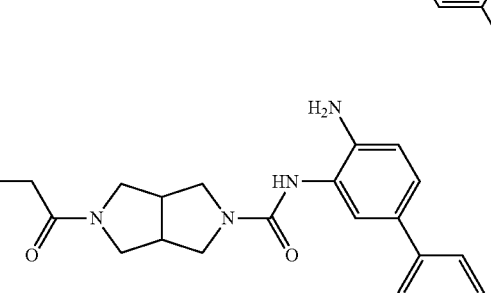 | 424 | 425 | δ 7.55-7.52 (m, 3H), 7.35 (d, J = 2.0 Hz, 1H), 7.22-7.17 (m, 3H), 6.77 (d, J = 8.4 Hz, 1H), 5.00 (s, 2H), 3.72-3.53 (m, 4H), 3.37-3.24 (m, 4H), 2.98-2.96 (m, 1H), 2.90-2.88 (m, 1H), 2.15-2.12 (m, 2H), 2.03-2.00 (m, 1H), 0.92 (s, 3H), 0.90 (s, 3H). |
| 161 | 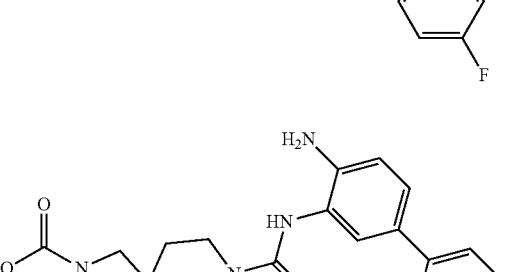 | 468 | 469 | δ 7.93 (s, 1H), 7.56-7.52 (m, 2H), 7.28 (d, J = 2.0 Hz, 1H), 7.22-7.17 (m, 3H), 6.78 (d, J = 8.4 Hz, 1H), 4.91 (s, 2H), 3.47-3.41 (m, 4H), 3.32-3.30 (m, 2H), 3.12 (s, 2H), 1.75-1.73 (m, 2H), 1.49 (s, 4H), 1.40 (s, 9H). |

TABLE 1-continued

Exemplary Compounds

| No. | Structure | MS Calc. | MS found | ¹H NMR Data (400 MHz, DMSO-d₆) |
|---|---|---|---|---|
| 162 | 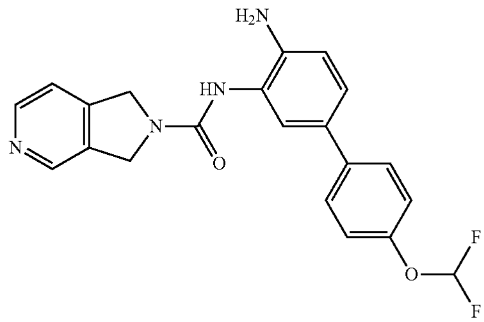 [SMILES: Nc1ccc(-c2ccc(OC(F)F)cc2)cc1NC(=O)N1Cc2ccncc2C1] | 396 | 397 | δ 8.62 (s, 1H), 8.50 (d, J = 5.2 Hz, 1H), 7.80 (s, 1H), 7.58 (d, J = 8.8 Hz, 2H), 7.45-7.42 (m, 2H), 7.25-7.18 (m, 3H), 6.80 (d, J = 8.4 Hz, 1H), 5.10 (br, 2H), 4.82 (d, J = 6.0 Hz, 4H). |
| 163 | 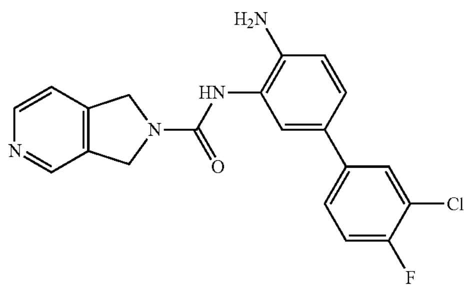 [SMILES: Nc1ccc(-c2ccc(F)c(Cl)c2)cc1NC(=O)N1Cc2ccncc2C1] | 382 | 383 | DMSO-d6 δ 8.62 (s, 1H), 8.51 (d, J = 5.2 Hz, 1H), 7.80 (s, 1H), 7.70 (dd, J = 7.2 Hz, 2.4 Hz, 1H), 7.56-7.52 (m, 1H), 7.45-7.40 (m, 3H), 7.28 (dd, J = 8.0 Hz, 2.0 Hz, 1H), 6.79 (d, J = 8.4 Hz, 1H), 5.18 (br, 2H), 4.82 (d, J = 6.4 Hz, 4H). |
| 164 | 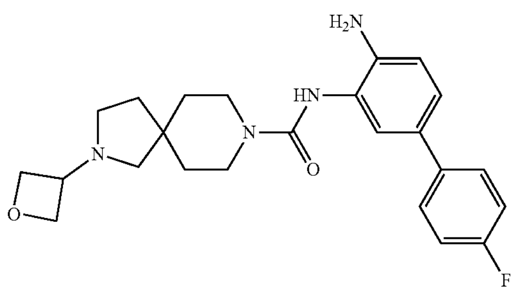 [SMILES: Nc1ccc(-c2ccc(F)cc2)cc1NC(=O)N1CCC2(CC1)CCN(C1COC1)C2] | 424 | 425 | CD₃OD δ 7.43 (dd, J = 8.8 Hz, 5.2 Hz, 2H), 7.17-7.13 (m, 2H), 7.00 (t, J = 8.8 Hz, 2H), 6.80 (d, J = 8.0 Hz, 1H), 4.63 (t, J = 6.4 Hz, 2H), 4.52 (t, J = 6.0 Hz, 2H), 3.57-3.38 (m, 5H), 2.54 (t, J = 6.8 Hz, 2H), 2.37 (s, 2H), 1.68 (t, J = 6.8 Hz, 2H), 1.58-1.55 (m, 4H). |
| 165 | 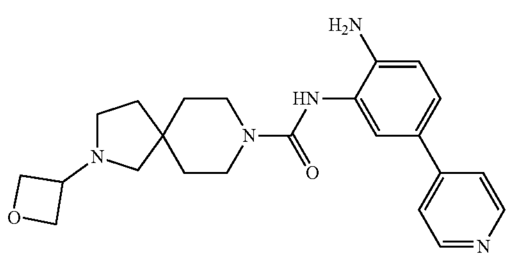 [SMILES: Nc1ccc(-c2ccncc2)cc1NC(=O)N1CCC2(CC1)CCN(C1COC1)C2] | 407 | 408 | CD₃OD δ 8.36 (d, J = 6.4 Hz, 2H), 7.53 (d, J = 6.4 Hz, 2H), 7.38-7.35 (m 2H), 6.82 (d, J = 8.4 Hz, 1H), 4.64 (t, J = 6.4 Hz, 2H), 4.52 (t, J = 6.4 Hz, 2H), 3.57-3.39 (m, 5H), 2.54 (t, J = 6.8 Hz, 2H), 2.38 (s, 2H), 1.69 (t, J = 6.8 Hz, 2H), 1.58-1.57 (m, 4H). |
| 166 | 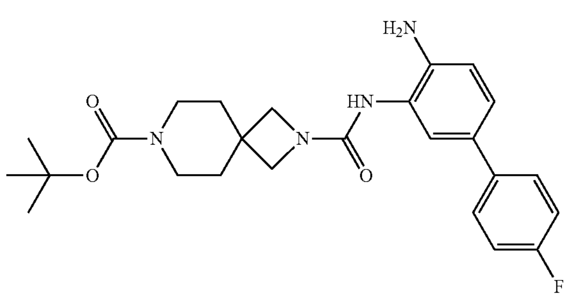 [SMILES: CC(C)(C)OC(=O)N1CCC2(CC1)CN(C(=O)Nc1cc(-c3ccc(F)cc3)ccc1N)C2] | 454 | 455 | δ 7.68 (br, 1H), 7.54-7.51 (m, 2H), 7.37 (d, J = 2.0 Hz, 1H), 7.22-7.16 (m, 3H), 6.76 (d, J = 8.4 Hz, 1H), 5.04 (br, 2H), 3.68 (s, 4H), 3.28 (s, 4H), 1.65 (t, J = 5.6 Hz, 4H), 1.40 (s, 9H). |

TABLE 1-continued

Exemplary Compounds

| No. | Structure | MS Calc. | MS found | ¹H NMR Data (400 MHz, DMSO-d₆) |
|---|---|---|---|---|
| 167 | 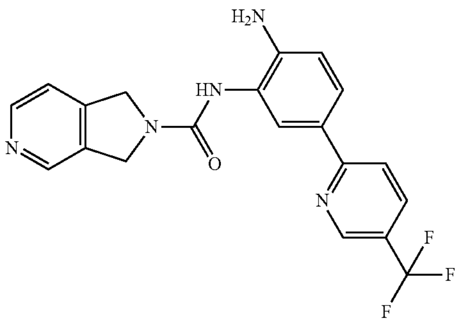 [SMILES: Nc1ccc(-c2ccc(C(F)(F)F)cn2)cc1NC(=O)N1Cc2ccncc2C1] | 399 | 400 | δ 8.88 (s, 1H), 8.62 (s, 1H), 8.10 (d, J = 5.2 Hz, 1H), 8.11 (dd, J = 8.4 Hz, J = 2.0 Hz, 1H), 7.98-7.96 (m, 2H), 7.86 (s, 1H), 7.79 (dd, J = 8.4 Hz, 2.4 Hz, 1H), 7.45 (d, J = 5.2 Hz, 1H), 6.81 (d, J = 8.8 Hz, 1H), 5.52 (br, 2H), 4.83 (d, J = 6.4 Hz, 4H). |
| 168 | 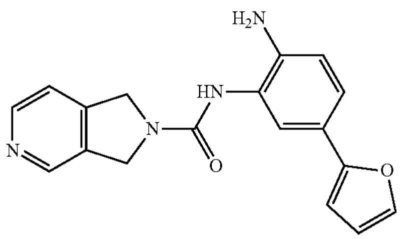 [SMILES: Nc1ccc(-c2ccco2)cc1NC(=O)N1Cc2ccncc2C1] | 320 | 321 | CD₃OD δ 8.38 (s, 1H), 8.34 (d, J = 5.2 Hz, 1H), 7.37 (d, J = 2.0 Hz, 1H), 7.31 (d, J = 1.6 Hz, 1H), 7.28 (d, J = 5.2 Hz, 1H), 7.17 (dd, J = 8.4 Hz, 2.0 Hz, 1H), 6.72 (d, J = 8.4 Hz, 1H), 6.36 (d, J = 3.6 Hz, 1H), 6.32-6.31 (m, 1H), 4.70 (d, J = 6.4 Hz, 4H). |
| 169 | 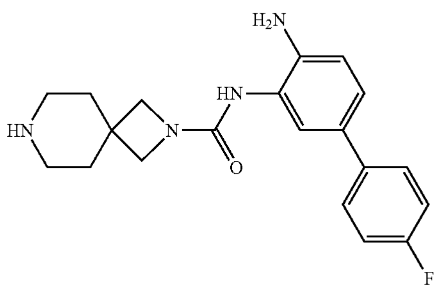 [SMILES: Nc1ccc(-c2ccc(F)cc2)cc1NC(=O)N1CC2(CCNCC2)C1] | 354 | 355 | δ 7.53 (s, 1H), 7.55-7.51 (m, 2H), 7.37 (d, J = 2.0 Hz, 1H), 7.22-7.15 (m, 3H), 6.76 (d, J = 8.4 Hz, 1H), 5.01 (s, 2H), 3.63 (s, 4H), 2.63-2.62 (m, 4H), 1.62-1.49 (m, 4H). |
| 170 | 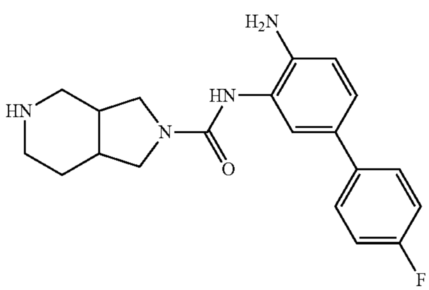 [SMILES: Nc1ccc(-c2ccc(F)cc2)cc1NC(=O)N1CC2CCNCC2C1] | 354 | 355 | δ 7.56-7.42 (m, 4H), 7.22-7.13 (m, 3H), 6.77 (t, J = 8.4 Hz, 1H), 4.98 (br, 2H), 3.39-3.28 (m, 4H), 2.78-2.74 (m, 2H), 2.67-2.63 (m, 1H), 2.21 (s, 2H), 1.96 (t, J = 4.0 Hz, 1H), 1.59-1.53 (m, 2H), 1.37-1.33 (m, 1H). |
| 171 | 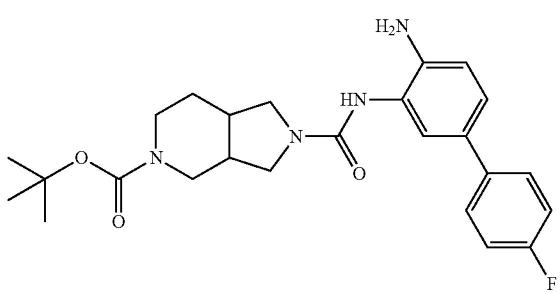 [SMILES: CC(C)(C)OC(=O)N1CCC2CN(C(=O)Nc3cc(-c4ccc(F)cc4)ccc3N)CC2C1] | 454 | 455 | δ 7.55-7.52 (m, 3H), 7.36 (d, J = 2.0 Hz, 1H), 7.22-7.16 (m, 3H), 6.77 (d, J = 8.4 Hz, 1H), 4.99 (s, 2H), 3.66-3.45 (m, 4H), 3.32-3.29 (m, 2H), 3.15-3.08 (m, 2H), 2.33 (br, 2H), 1.65-1.62 (m, 1H), 1.41 (s, 9H), 1.39-1.34 (m, 1H). |

TABLE 1-continued

Exemplary Compounds

| No. | Structure | MS Calc. | MS found | $^1$H NMR Data (400 MHz, DMSO-$d_6$) |
|---|---|---|---|---|
| 172 | 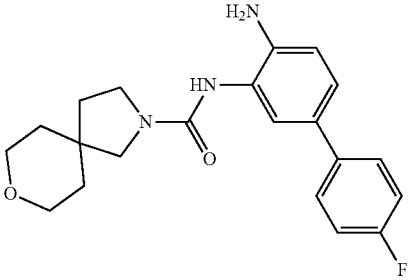 [SMILES: Nc1ccc(-c2ccc(F)cc2)cc1NC(=O)N1CCC2(CCOCC2)C1] | 369 | 370 | δ 7.56-7.52 (m, 2H), 7.50 (s, 1H), 7.37 (d, J = 2.4 Hz, 1H), 7.22-7.16 (m, 3H), 6.77 (d, J = 8.0 Hz, 1H), 4.99 (s, 2H), 3.65-3.61 (m, 2H), 3.57-3.53 (m, 2H), 3.46 (t, J = 6.8 Hz, 2H), 3.31 (s, 2H), 1.80 (t, J = 6.8 Hz, 2H), 1.52 (t, J = 5.2 Hz, 4H). |
| 173 | 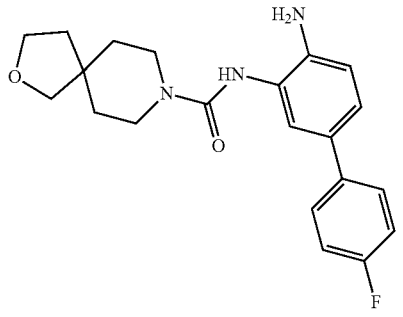 [SMILES: Nc1ccc(-c2ccc(F)cc2)cc1NC(=O)N1CCC2(CCOC2)CC1] | 369 | 370 | δ 7.94 (s, 1H), 7.56-7.52 (m, 2H), 7.28 (d, J = 2.4 Hz, 1H), 7.22-7.17 (m, 3H), 6.78 (d, J = 8.4 Hz, 1H), 4.90 (s, 2H), 3.76 (t, J = 6.8 Hz, 2H), 3.52-3.48 (m, 4H), 3.40-3.36 (m, 2H), 1.75 (t, J = 7.2 Hz, 2H), 1.52 (t, J = 5.6 Hz, 4H). |
| 174 | 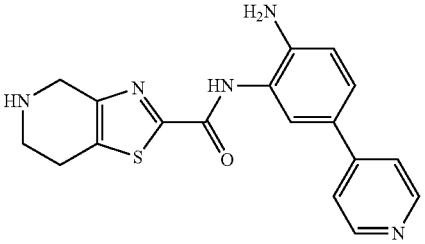 [SMILES: Nc1ccc(-c2ccncc2)cc1NC(=O)c1nc2c(s1)CCNC2] | 351 | 352 | δ 10.06 (br, 1H), 8.51 (d, J = 5.6 Hz, 2H), 7.73 (s, 1H), 7.57 (d, J = 6.0 Hz, 2H), 7.51 (dd, J = 6.8 Hz, 1.6 Hz, 1H), 6.89 (d, J = 8.4 Hz, 1H), 5.39 (br, 2H), 4.00 (s, 2H), 3.06 (t, J = 5.6 Hz, 2H), 2.90 (s, 2H). |
| 175 | 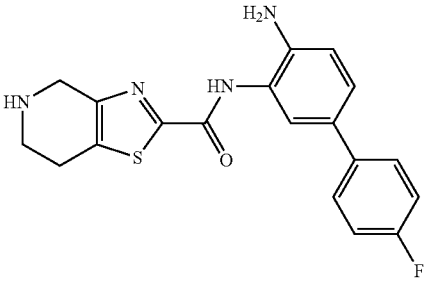 [SMILES: Nc1ccc(-c2ccc(F)cc2)cc1NC(=O)c1nc2c(s1)CCNC2] | 368 | 369 | δ 10.00 (br, 1H), 7.58-7.55 (m, 3H), 7.29 (dd, J = 8.4 Hz, 2.0 Hz, 1H), 7.22 (t, J = 8.8 Hz, 1H), 6.87 (d, J = 8.4 Hz, 1H), 5.11 (br, 2H), 3.93 (s, 2H), 2.99 (t, J = 5.2 Hz, 2H), 2.85 (t, J = 5.2 Hz, 2H), 2.68 (s, 1H). |

In some embodiments, the invention includes a pharmaceutical composition comprising a compound described herein (e.g., a compound according to Formula I or any of Compounds 100-175) or a pharmaceutically acceptable salt thereof; and a pharmaceutically acceptable carrier.

In other embodiments, the invention features a method of inhibiting HDAC activity (e.g., HDAC2 activity) in a subject comprising the step of administering to a subject in need thereof an effective amount of a compound described herein (e.g., a compound according to Formula I or any Compounds 100-175) or a pharmaceutically acceptable salt thereof, or a composition thereof.

In other embodiments, the invention features a method of treating a condition in a subject selected from a neurological disorder, memory or cognitive function disorder or impairment, extinction learning disorder, fungal disease or infection, inflammatory disease, hematological disease, and neoplastic disease, comprising administering to a subject in need thereof an effective amount of a compound described herein (e.g., a compound according to Formula I or any of Compounds 100-175) or a pharmaceutically acceptable salt thereof, or a composition thereof.

In still other embodiments, the invention features a method of improving memory in a normal subject or treating, alleviating, or preventing memory loss or impairment in a subject comprising administering to the subject in need thereof an effective amount of a compound described herein (e.g., a compound according to Formula I or any of Compounds 100-175) or a pharmaceutically acceptable salt thereof, or a composition thereof.

In certain embodiments, the condition is:
a. a cognitive function disorder or impairment associated with Alzheimer's disease, Huntington's disease, seizure induced memory loss, schizophrenia, Rubinstein Taybi syndrome, Rett Syndrome, Fragile X, Lewy body dementia, vascular dementia, frontotemporal dementia, ADHD, dyslexia, bipolar disorder and social, cognitive and learning disorders associated with autism, traumatic head injury, attention deficit disorder, anxiety disorder, conditioned fear response, panic disorder, obsessive compulsive disorder, posttraumatic stress disorder (PTSD), phobia, social anxiety disorder, substance dependence recovery, Age Associated Memory Impairment (AAMI), Age Related Cognitive Decline (ARCD), ataxia, or Parkinson's disease; or
b. a hematological disease selected from acute myeloid leukemia, acute promyelocytic leukemia, acute lymphoblastic leukemia, chronic myelogenous leukemia, myelodysplastic syndromes, and sickle cell anemia; or
c. a neoplastic disease; or
d. an extinction learning disorder selected from fear extinction and post-traumatic stress disorder.

In further embodiments, the condition is Alzheimer's disease, Huntington's disease, frontotemporal dementia, Freidreich's ataxia, post-traumatic stress disorder (PTSD), Parkinson's disease, or substance dependence recovery.

In still other embodiments, the method is a combination therapy further comprising:
a. administering to the subject an effective amount of a pharmaceutically active ingredient; and/or
b. exposing the subject to cognitive behavioral therapy (CBT), psychotherapy, behavioral exposure treatments, virtual reality exposure (VRE) and/or cognitive remediation therapy.

In other embodiments, the method is a combination therapy for treating, alleviating, and/or preventing post-traumatic stress disorder or Alzheimer's disease and the pharmaceutically active ingredient administered is selected from Aricept®, memantine, galantamine and Excelon® (rivastigmine).

In some embodiments, the invention features a method of increasing synaptic density or increasing synaptic plasticity or increasing dendritic density in a subject comprising administering to the subject in need of such increase an effective amount of a compound described herein (e.g., a compound according to Formula I or any of Compounds 100-175) or a pharmaceutically acceptable salt thereof, or a composition thereof.

In still other embodiments, a compound described herein (e.g., a compound according to Formula I or any of Compounds 100-175), a pharmaceutically acceptable salt thereof, or a compound or salt (e.g., a compound according to Formula I or any of Compounds 100-175, or a pharmaceutically acceptable salt thereof) in the pharmaceutical composition selectively inhibits HDAC2.

In certain embodiments, a compound described herein (e.g., a compound according to Formula I or any of Compounds 100-175), a pharmaceutically acceptable salt thereof, or a compound or salt (e.g., a compound according to Formula I or any of Compounds 100-175, or a pharmaceutically acceptable salt thereof) in the pharmaceutical composition compound has at least 2-, 5-, 10-, 15-, or 20-fold greater inhibition of HDAC2 as compared to one or more other HDAC isoforms.

In further embodiments, the other HDAC isoform is HDAC1.

General Synthetic Methods and Intermediates:

The compounds of the present invention can be prepared by methods known to one of ordinary skill in the art and/or by reference to the schemes shown below and the synthetic examples that follow. Exemplary synthetic routes are set forth in the Schemes below, and in the Examples.

One of ordinary skill in the art will recognize that numerous variations in reaction conditions including variations in solvent, reagents, catalysts, reaction temperatures and times are possible for each of the reactions described. Variation of order of synthetic steps and alternative synthetic routes are also possible.

The compounds of the present invention can be prepared by methods known to one of ordinary skill in the art and/or by reference to the schemes shown below and the synthetic examples that follow.

4. Uses, Formulation and Administration

Exemplary Uses

Compounds of the invention are inhibitors of class I histone deacetylases (HDAC) and in particular HDAC2, and are useful for promoting cognitive function and enhancing learning and memory formation. As a result, these compounds are useful in treating, alleviating, and/or preventing various conditions, including e.g., neurological disorders, memory and cognitive function disorders/impairments, extinction learning disorders, fungal diseases, inflammatory diseases, hematological diseases, and neoplastic diseases in humans and animals HDAC Inhibition The compounds of the present invention are useful in a variety of applications for human and animal health. The compounds of the invention are histone deacetylase (HDAC) inhibitors. A histone deacetylase inhibitor as used herein is a compound that inhibits, reduces, or otherwise modulates the activity of histone deacetylase. HDACs catalyze the removal of acetyl groups from lysine residues on proteins, including histones. HDAC inhibitors also show diverse biological functions including effecting gene expression, cell differentiation, cell cycle progression, growth arrest, and/or apoptosis. (J. Med. Chem. 2003, 46:5097 and Curr. Med. Chem. 2003, 10:2343). In various embodiments, the compounds of the invention reduce HDAC activity by at least about 50%, at least about 75%, or at least about 90% or more. In further embodiments, HDAC activity is reduced by at least about 95% or at least about 99% or more.

One aspect of the invention provides a method of inhibiting histone deacetylase in a cell, comprising contacting a cell in which inhibition of histone deacetylase is desired with an inhibition effective amount of a compound of the invention or a composition thereof. Because compounds of the invention inhibit histone deacetylase(s), they are useful research tools for in vitro study of the role of histone deacetylase in biological processes. Accordingly, in one aspect of the invention, the step of contacting the cell is performed in vitro.

The term an "inhibiting effective amount" is meant to denote a dosage sufficient to cause inhibition of activity of one or more histone deacetylase in a cell, which cell can be in a multicellular organism. The multicellular organism can be a plant, a fungus, or an animal, preferably a mammal, more preferably a human. The fungus may be infecting a plant or a mammal, preferably a human, and could therefore be located in and/or on the plant or mammal. If the histone deacetylase is in a multicellular organism, the method according to this aspect of the invention comprises administering to the organism a compound or composition of the invention. Measurement of the effect of a compound of the invention on the enzymatic activity of a histone deacetylase is achieved using known methodologies. For example, Bradner, J. et al. Nature Chemical Biology, Vol. 6, March 2010, 238-243.

The potential of HDAC inhibitors is tremendous, but the development of clinical compounds will likely require the design of isoform selective compounds to minimize side effect issues e.g., fatigue, anorexia, hematological and GI-toxicity. Isoform specific HDAC inhibitors provide advantages by reducing toxicities associated with inhibition of other HDACs. Specific HDAC inhibitors provide a higher therapeutic index, resulting in better tolerance by patients during chronic or long term treatment. While several HDAC inhibitors are now in the clinic, most of these do not show significant selectivity for individual HDAC isoforms.

The compounds of the present invention inhibit HDAC2. In some embodiments, the compound reduces the activity of other, but fewer than all histone deacetylases in the cell. In certain embodiments, the compound reduces the activity of HDAC2 to a greater extent than other histone deacetylases.

In certain embodiments, the present invention relates to the aforementioned compound, wherein the compounds of the invention are selective HDAC2 inhibitors.

In one embodiment, a compound of the invention is selective for HDAC2 and will have at least about 2-fold (e.g., at least about 5-fold, 10-fold, 15-fold, or 20-fold) greater activity to inhibit HDAC2 as compared to one or more other HDACs (e.g., one or more HDACs of class I or II). In one embodiment, a compound of the invention will have at least about 2-fold (e.g., at least about 5-fold, 10-fold, 15-fold, or 20-fold) greater activity to inhibit HDAC2 as compared to HDAC3. In one embodiment, a compound of the invention will have at least about 2-fold (e.g., at least about 5-fold, 10-fold, 15-fold, or 20-fold) greater activity to inhibit HDAC2 as compared to HDAC1. In one embodiment, a compound of the invention will have at least about 2-fold (e.g., at least about 5-fold, 10-fold, 15-fold, or 20-fold) greater activity to inhibit HDAC2 as compared to all other HDACs of a particular class of HDACs (e.g., one or more HDACs of class I or II). In one embodiment, a compound of the invention will have at least about 2-fold (e.g., at least about 5-fold, 10-fold, 15-fold, or 20-fold) greater activity to inhibit HDAC2 as compared to all other HDACs.

In another embodiment, a compound selectively inhibits HDAC2 with an $IC_{50}$ value greater than 0.0000001 μM and less than or equal to 0.1 μM, 1 μM, 5 μM, or 30 μM.

The compounds described herein (e.g., a Compound of Formula I or any of Compounds 100-175) provide an additional mechanism by which selectivity and an increased margin of safety may be obtained. In some embodiments, the compounds described herein (e.g., a Compound of Formula I or any of Compounds 100-175) partially inhibit the activity of HDAC2 within specific cells. Without being limited by theory, this partial inhibition is hypothesized to be the result of differential efficacy on HDAC2 when it resides within a multiple protein complex in the cell. The multiple protein complexes which contain HDAC2 vary between cells, with specific complexes existing within specific cell types. Accordingly, the compounds described herein (e.g., a Compound of Formula I or any of Compounds 100-175) are proposed to incompletely inhibit the activity of HDAC2 in some cells, sparing sufficient HDAC function to provide an improved margin of safety while maintaining enough inhibition to result in the desired effect.

Neurological Disorders

In one aspect, the invention provides methods and compositions for treating, alleviating, and/or preventing neurological disorders.

Recent reports have detailed the importance of histone acetylation in central nervous system ("CNS') functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525).

In one aspect, the invention provides methods and compositions for treating, alleviating, and/or preventing neurological disorders. The term "neurological disorder" as used herein includes neurological diseases, neurodegenerative diseases and neuropsychiatric disorders. A neurological disorder is a condition having as a component a central or peripheral nervous system malfunction. Neurological disorders may cause a disturbance in the structure or function of the nervous system resulting from developmental abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems).

As used herein, the term "neurodegenerative disease" implies any disorder that might be reversed, deterred, managed, treated, improved, or eliminated with agents that stimulate the generation of new neurons. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapic, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke- Korsakoff's related dementia. Neurodegenerative diseases affecting sensory neurons include Friedreich's ataxia, diabetes, peripheral neuropathy, and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

In some instances the neurological disorder is a neuropsychiatric disorder, which refers to conditions or disorders that relate to the functioning of the brain and the cognitive processes or behavior. Neuropsychiatric disorders may be further classified based on the type of neurological disturbance affecting the mental faculties. The term "neuropsychiatric disorder," considered here as a subset of "neurological disorders," refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV).

One group of neuropsychiatric disorders includes disorders of thinking and cognition, such as schizophrenia and delirium. A second group of neuropsychiatric disorders includes disorders of mood, such as affective disorders and anxiety. A third group of neuropsychiatric disorders includes disorders of social behavior, such as character defects and personality disorders. A fourth group of neuropsychiatric disorders includes disorders of learning, memory, and intelligence, such as mental retardation and dementia. Accordingly, neuropsychiatric disorders encompass schizophrenia, delirium, attention deficit disorder (ADD), schizoaffective disorder, Alzheimer's disease, Rubinstein-Taybi syndrome, depression, mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

In one embodiment, the neurological disorder is Alzheimer's disease, Huntington's disease, seizure-induced memory loss, schizophrenia, Rubinstein Taybi syndrome, Rett Syndrome, Fragile X, Lewy body dementia, vascular dementia, ADHD, ADD, dyslexia, bipolar disorder and social, cognitive and learning disorders associated with autism, traumatic head injury, or attention deficit disorder.

In another embodiment, the neurological disorder is an anxiety disorder, conditioned fear response, panic disorder, obsessive compulsive disorder, post-traumatic stress disorder, phobia, social anxiety disorder, or substance dependence recovery.

In some embodiments neurological disorders are treated or prevented by decreasing the amount of DNA damage within the neuronal cell. In some embodiments neurological disorders are treated or prevented by increasing histone deacetylase activity within the neuronal cell. In some embodiments neurological disorders are treated or prevented by decreasing histone acetyl transferase activity within the neuronal cell. In some embodiments neurological disorders are treated or prevented by increasing the activity of class I histone deacetylases.

Enhancing Cognitive Function

In one aspect, the invention provides methods and compositions for promoting cognitive function and enhancing learning and memory formation in both normal subjects as well as those suffering from memory loss and cognitive function disorders/impairments. A normal subject, as used herein, is a subject that has not been diagnosed with a disorder associated with impaired cognitive function. "Cognitive function" refers to mental processes of a subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like.

Memory Disorders/Impairment

Transcription is thought to be a key step for long-term memory processes (Alberini, 2009, Physiol. Rev. 89, 121-145). Transcription is promoted by specific chromatin modifications, such as histone acetylation, which modulate histone-DNA interactions (Kouzarides, 2007, Cell, 128:693-705). Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467).

A "memory" as used herein refers to the ability to recover information about past events or knowledge. Memories include short-term memory (also referred to as working or recent memory) and long-term memory. Short-term memories involve recent events, while long-term memories relate to the recall of events of the more distant past. Methods of assessing the ability to recall a memory are known to those of skill in the art and may involve routine cognitive tests. Enhancing or retrieving memories is distinct from learning. However, in some instances in the art learning is referred to as memory. Learning, unlike memory enhancement, refers to the ability to create new memories that had not previously existed. Thus in order to test the ability of a compound to effect the ability of a subject to learn rather than recall old memories, the compound would be administered prior to or at the same time as the memory is created. In order to test the ability of a compound to affect recall of a previously created memory the compound is administered after the memory is created and preferably after the memory is lost.

As used herein "age related memory loss" refers to any of a continuum of conditions characterized by a deterioration of neurological functioning that does not rise to the level of a dementia, as further defined herein and/or as defined by the Diagnostic and Statistical Manual of Mental Disorders: 4th Edition of the American Psychiatric Association (DSM-IV, 1994). Age related memory loss is characterized by objective loss of memory in an older subject compared to his or her younger years, but cognitive test performance that is within normal limits for the subject's age. Age related memory loss subjects score within a normal range on standardized diagnostic tests for dementias, as set forth by the DSM-IV. Moreover, the DSM-IV provides separate diagnostic criteria for a condition termed Age-Related Cognitive Decline. In the context of the present invention, as well as the terms "Age-Associated Memory Impairment" and "Age-Consistent Memory Decline" are understood to be synonymous with the age related memory loss. Age-related memory loss may include decreased brain weight, gyral atrophy, ventricular dilation, and selective loss of neurons within different brain regions. For purposes of some embodiments of the present invention, more progressive forms of memory loss are also included under the definition of age-related memory disorder. Thus persons having greater than age-normal memory loss and cognitive impairment, yet scoring below the diagnostic threshold for frank dementia, may be referred to as having a mild neurocognitive disorder, mild cognitive impairment, late-life forgetfulness, benign senescent forgetfulness, incipient dementia, provisional dementia, and the like. Such subjects may be slightly more susceptible to developing frank dementia in later life (See also US patent application 2006/008517 (Vasogen Ireland limited) which is incorporated by reference). Symptoms associated with age-related memory loss include but are not limited to alterations in biochemical markers associated with the aging brain, such as IL-1 beta, IFN-gamma, p-JNK, p-ERK, reduction in synaptic activity or function, such as synaptic plasticity, evidenced by reduction in long term potentiation, diminution of memory and learning.

As used herein "injury related memory loss" refers to a loss of memory wherein there is damage to the brain, and there may have also been neurological damage. Sources of brain injury include traumatic brain injury such as concussive injuries or penetrating head wounds, brain tumors, alcoholism, Alzheimer's disease, stroke, heart attack and other conditions that deprive the brain of oxygen, meningitis, AIDS, viral encephalitis, and hydrocephalus.

Methods for enhancing memories can include reestablishing access to memories as well as recapturing memories. The term re-establishing access as used herein refers to increasing retrieval of a memory. Although Applicants are not bound by a mechanism of action, it is believed that the compounds of the invention are effective in increasing retrieval of memories by re-establishing a synaptic network. The process of re-establishing a synaptic network may include an increase in the number of active brain synapses and or a reversal of neuronal loss.

Neurogenesis, or the birth of new neuronal cells, was thought to °Ccur only in developing organisms. However, recent research has demonstrated that neurogenesis does indeed continue into and throughout adult life. On going neurogenesis is thought to be an important mechanism underlying neuronal plasticity, enabling organisms to adapt to environmental changes and influencing learning and memory throughout life. In one aspect, the invention includes a method of increasing synaptic density in a subject comprising administering to the subject in need of such increase a compound of the invention or a pharmaceutically acceptable salt, hydrate, solvate, or prodrug thereof. In one aspect, the invention includes a method of increasing synaptic plasticity in a subject comprising administering to the subject in need of such increase a compound of the invention or a pharmaceutically acceptable salt, hydrate, solvate, or prodrug thereof. In one aspect, the invention includes a method of increasing dendritic density in neurons in a subject comprising administering to the subject in need of such increase a compound of the invention or a pharmaceutically acceptable salt, hydrate, solvate, or prodrug thereof.

The invention provides methods for enhancing memory in a subject having a memory disorder. Examples of types of memory disorders include Alzheimer's disease, absent-minded professor, absent-mindedness, amnesia, anterograde amnesia, blackout (alcohol-related amnesia), bromism, childhood amnesia, false memory syndrome, fugue state, hyperthymesia, Korsakoff's syndrome, lacunar amnesia, memory distrust syndrome, memory loss, post-traumatic amnesia, prosopamnesia, psychogenic amnesia, repressed memory, retrograde amnesia, Ribot's Law, selective memory loss, source amnesia, source-monitoring error, the seven sins of memory, tip of the tongue, transient epileptic amnesia, transient global amnesia, and twilight sleep.

In one embodiment, Alzheimer's disease is the memory disorder. Such methods optionally involve administering the inhibitor and monitoring the subject to identify recapture of a memory that was previously lost. Subjects may be monitored by routine tests known in the art.

In other embodiments the alzheimer's subject is one that has late stage Alzheimer's disease. Many of the drugs suggested for treating Alzheimer's disease are designed to treat the early stages of the disease by preventing plaque buildup. The compounds of the invention are useful for treating both early stages and late stages of dementia because they actually improve memory and cognition rather than preventing only plaque accumulation.

Cognitive Function Disorders/Impairment

The invention relates to methods of treating, alleviating, and/or preventing cognitive function disorders/impairments.

Impaired cognitive function refers to cognitive function that is not as robust as that observed in an age-matched normal subject and includes states in which cognitive function is reduced. In some cases, cognitive function is reduced by about 5%, about 10%, about 30%, or more, compared to cognitive function measured in an age-matched normal subject. Cognitive function may be promoted to any detectable degree, but in humans preferably is promoted sufficiently to allow an impaired subject to carry out daily activities of normal life.

In some embodiments, the cognitive function disorders or impairments are associated with, but not limited to, Alzheimer's disease, Huntington's disease, seizure induced memory loss, schizophrenia, Rubinstein Taybi syndrome, Rett Syndrome, Fragile X, Lewy body dementia, Vascular dementia, bipolar disorder and social, cognitive and learning disorders associated with autism, attention deficit hyperactivity disorder (ADHD), dyslexia, learning disorders, traumatic head injury, stroke induced cognitive and motor impairment, traumatic brain injury, neurodegeneration and neuronal loss mediated cognitive impairment, and attention deficit disorder.

In some embodiments, the cognitive function disorders or impairments are associated with, but not limited to, anxiety disorders, conditioned fear response, panic disorders, obsessive compulsive disorders, post-traumatic stress disorder, phobias, social anxiety disorders, substance dependence recovery or Age Associated Memory Impairment (AAMI), and Age Related Cognitive Decline (ARCD).

In some embodiments, the invention relates to methods of treating, alleviating, and/or preventing vascular dementia. Vascular dementia, also referred to as "multi-infarct dementia", refers to a group of syndromes caused by different mechanisms all resulting in vascular lesions in the brain. The main subtypes of vascular dementia are, for example vascular mild cognitive impairment, multi-infarct dementia, vascular dementia due to a strategic single infarct (affecting the thalamus, the anterior cerebral artery, the parietal lobes or the cingulate gyms), vascular dementia due to hemorrhagic lesions, small vessel disease (including, e.g. vascular dementia due to lacunar lesions and Binswanger disease), and mixed Alzheimer's Disease with vascular dementia.

In some embodiments, the invention relates to treating, alleviating, and/or preventing Huntington's disease. Huntington's disease is a neurological disease which results in cognitive decline associated with inexorable progression to death. Cognitive symptoms associated with Huntington's disease include loss of intellectual speed, attention, and short term memory and/or behavioral symptoms.

Cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." Neurotoxicol Teratol 1996; 18(4):499-504), Stroop Test, Trail Making, Wechsler Digit Span, or the CogState computerized cognitive test (see also Dehaene et al. "Reward-dependent learning in neuronal networks for planning and decision making " Brain Res. 2000;126:21729; Iverson et al. "Interpreting change on the WAIS-III/WMS-III in clinical samples. " Arch Clin Neuropsychol. 2001;16 (2):183- 91; and Weaver et al. "Mild memory impairment in healthy older adults is distinct from normal aging." Cogn. 2006;60(2):146-55). The methods of the invention may be used to promote cognitive function in a normal subject or to treat, alleviate and/or prevent a subject from having a cognitive dysfunction. A normal subject, as used herein, is a subject that has not been diagnosed with a disorder associated with impaired cognitive function.

Extinction Learning Disorders

In one aspect, the invention relates to methods of treating, alleviating, and/or preventing extinction learning disorders e.g., a fear extinction deficit.

It has been demonstrated that administration of the HDAC inhibitors sodium butyrate or trichostatin A facilitates fear extinction in mice and this enhancement mirrors that caused by commonly used behavioral manipulation and is consistent with other studies demonstrating a role for the hippocampus in the extinction of contextual fear (Lattal, et al., 2007, Behav. Neurosci. 121, 5, 1125-1131).

Compounds of the invention can be used to facilitate the psychological process of extinction learning and thus are useful for treating, alleviating, and/or preventing neuropsychiatric disorders and other related disorders. Unlike traditional anti-anxiety drugs that are administered on a chronic basis and address physiological symptoms of anxiety, the compounds of the invention can be used on a chronic or acute basis in conjunction with a second therapy e.g., psychotherapy.

In one aspect, the present invention is directed to methods for treating, alleviating, and/or preventing a subject from having a neuropsychiatric disorder. The methods comprise subjecting the subject to one or more sessions of a combination therapy protocol, where the combination therapy protocol comprises an acute administration of a therapeutically effective amount of a compound of the invention that enhances learning or conditioning in combination with a session of psychotherapy. By "acute administration" is intended a single exposure of the subject to the therapeutically effective amount of the compound that enhances learning or conditioning. In one aspect, the exposure to the compound °Ccurs within about 24 hours prior to initiating the session of psychotherapy, preferably within about 12 hours, and more preferably within about 6 hours prior to initiating the session of psychotherapy. A full course of treatment for the neuropsychiatric disorder entails at least one session of this combination therapy protocol.

For purposes of the present invention, a subject may have a single disorder, or may have a constellation of disorders that are to be treated, alleviated, and/or prevented by the methods described herein.

The neuropsychiatric disorders contemplated in the present invention include, but are not limited to, fear and anxiety disorders, addictive disorders including substance-abuse disorders, and mood disorders. Within the fear and anxiety disorder category, the invention encompasses the treatment or prevention of panic disorder, specific phobia, post-traumatic stress disorder (PTSD), obsessive-compulsive disorder, and movement disorders such as Tourette's syndrome. The disorders contemplated herein are defined in, for example, the DSM-IV (Diagnostic and Statistical Manual of Mental Disorders (4th ed., American Psychiatric Association, Washington D.C., 1994)), which is herein incorporated by reference.

Anxiety-related disorders relate to those disorders characterized by fear, anxiety, addiction, and the like. Patients with anxiety-related disorders can have a single such disorder, or can have a constellation of disorders. The anxiety-related disorders contemplated in the present invention include, but are not limited to, anxiety disorders, addictive disorders including substance-abuse disorders, mood disorders (e.g., depression and/or bipolar disorder), movement disorders such as Tourette's syndrome, psychogenic erectile dysfunction (impotence resulting from a man's inability to obtain or maintain an erection of his penis), insomnia (e.g. chronic insomnia), and eating disorders (e.g. anorexia).

Anxiety disorders include, but are not limited to, panic disorder, agoraphobia, social phobia, specific phobia, PTSD, obsessive-compulsive disorder, and generalized anxiety disorder. The disorders contemplated herein are defined in, for example, the DSM-IV (Diagnostic and Statistical Manual of Mental Disorders (4th ed., American Psychiatric Association, Washington D.C., 1994)).

Movement disorders are neurological conditions that affect the speed, fluency, quality, and ease of movement. Representative movement disorders include but are not limited to ataxia, chorea, myoclonus, dystonia, Parkinson's disease, restless leg syndrome, tics, and Tourette's syndrome. Movement disorders typically °Ccur as a result of damage or disease in the basal ganglia region of the brain. Movement disorders can result from age-related changes, medications, genetic disorders, metabolic disorders, disease, stroke, or injury. Recovery of movement after stroke or injury may be facilitated when treated according to the methods of the invention.

Addictive disorders are disorders characterized by addiction to an activity or substance, and include, for example, alcohol addiction, drug addiction, and gambling addiction.

Depression refers to the clinical condition known as major depressive disorder, and is characterized by a state of intense sadness, melancholia, or despair that has advanced to the point of being disruptive to an individual's social functioning and/or activities of daily living. Depression is alleviated if either (or both) the severity or frequency of a symptom of the depression is reduced. However, a subject can be treated for depression in accordance with the methods of the invention irrespective of whether the treatment actually was successful in alleviating the depression.

Insomnia is defined herein as the inability to fall asleep or to stay asleep for a sufficient amount of time during regular sleeping hours. It includes acute insomnia, which °Ccurs in either a transient or short term form, and chronic insomnia.

It also includes initial insomnia, defined as difficulty in falling asleep; middle insomnia, defined as awakening in the middle of the night followed by eventually falling back to sleep, but with difficulty; and terminal insomnia, defined as awakening before one's usual waking time and being unable to return to sleep.

As defined by the National Institute of Mental Health, Autism Spectrum Disorders (ASD), also widely known as Pervasive Developmental Disorders (PDDs), cause severe and pervasive impairment in thinking, feeling, language, and the ability to relate to others. These disorders are usually first diagnosed in early childhood and range from a severe form, called autistic disorder, through pervasive development disorder not otherwise specified (PDD-NOS), to a much milder form, Asperger syndrome. They also include two rare disorders, Rett syndrome and childhood disintegrative disorder.

Attention-Deficit Hyperactivity Disorder (ADHD) is one of the most common mental disorders that develop in children. Children with ADHD typically have impaired functioning in multiple settings, including home, school, and in relationships with peers. Symptoms of ADHD include impulsiveness, hyperactivity, and inattention.

Typical treatments encompassed by the present invention include combination therapies. For instance, the combination therapy may be a pharmacotherapy (i.e., a compound of the invention) and a behavioral therapy. Behavioral therapy comprises, but is not limited to, electroconvulsive seizure therapy, exercise, group therapy, talk therapy, or conditioning. In another embodiment, the behavioral therapy is cognitive-behavioral therapy. Examples of behavioral therapy that may be used in the ongoing methods are described, for example, in Cognitive-Behavioral Therapies by K. Dobson, ed., Guilford Publications, Inc., 2002; The new Handbook of Cognitive Therapy: Basics and Beyond by Judith S. S. Beck, Guilford Publications, Inc. 1995 herein incorporated by reference in their entireties. Any pharmaceutical active ingredient that is recognized by the skilled artisan as being a pharmacologic agent that enhances learning or conditioning can be used in the methods of the invention. For example, one such class of pharmaceutical active ingredients contemplated herein comprises compounds that increase the level of norepinephrine in the brain. Such compounds include those acting as norepinephrine reuptake inhibitors, for example tomoxetine, reboxetine, duloxetine, venlafaxine, and milnacipran, and those compounds that cause release of norepinephrine, for example amphetamine, dextroamphetamine, pemoline, and methylphenidate. Another class of such pharmaceutical active ingredients is those compounds that increase the level of acetylcholine in the brain, including, for example, compounds that block its breakdown. Examples of such compounds include, but are not limited to, donepezil HCl or Aricept™ and tacrine, which inhibit cholinesterase activity.

Methods of the invention also encompass the use in combination with a compound of the invention of any type of psychotherapy that is suitable for the particular psychiatric disorder for which the subject is undergoing treatment. Suitable methods of psychotherapy include exposure based psychotherapy, cognitive psychotherapy, and psychodynamically oriented psychotherapy. Methods of the invention also encompass exposing the subject to cognitive behavioral therapy (CBT), behavioral exposure treatments, virtual reality exposure (VRE) or cognitive remediation therapy.

Methods of the invention also encompass extinction training. The goal of extinction training is to pair a stimulus that previously provoked a deleterious, unwanted response with a new learning that will not lead to a negative outcome, thereby generating in a subject a new, more appropriate response to the stimulus to compete with and ideally replace the previous undesirable response. Extinction training frequently exposes a subject to a stimulus or situation in the absence of an aversive consequence, e.g., a subject that has deleterious, high anxiety responses to a given stimulus or situation is exposed to that stimulus or situation in the absence of an aversive consequence. A typical goal of extinction training is to produce new learning in the subject that results from the pairing of the original stimulus or situation with a non-deleterious outcome, thereby generating, in subsequent exposures to the stimulus, a more appropriate response in place of the unwanted response. An extinction learning event refers to a completed stimulus/response extinction training cycle.

One form of extinction training entails psychotherapy. For example, the methods of the invention contemplate treating, alleviating, and/or preventing anxiety disorders by: (i) administering psychotherapy to treat, alleviate, and/or prevent an anxiety-related disorder in a suitable human subject, and (ii) administering a therapeutically effective dose a compound of the invention to said subject on an achronic, post-training, pre-sleep basis. Suitable methods of psychotherapy include but are not limited to exposure-based psychotherapy, cognitive psychotherapy, and psychodynamically oriented psychotherapy.

One method of psychotherapy that is specifically contemplated is the use of virtual reality (VR) exposure therapy to treat, alleviate, and/or prevent an anxiety disorder using the methods of the invention.

Another method of psychotherapy that is particularly beneficial when utilized in combination with a compound or composition of the present invention is cognitive behavioral therapy ("CBT"). CBT is a form of psychotherapy that combines cognitive therapy and behavior therapy, and emphasizes the critical role of thinking in causing people to act and feel as they do. Therefore, if an individual is experiencing unwanted feelings and behaviors, CBT teaches that it is important to identify the thinking that is causing the undesirable feelings and/or behaviors and to learn how to replace this deleterious thinking with thoughts that lead to more desirable reactions. CBT is widely used to help people who are experiencing a range of mental health difficulties, some of which do not conveniently fit definitions of a particular medical affliction. CBT has been used to treat anxiety disorders, mood disorders, addictive disorders, eating disorders, insomnia, chronic pain, schizophrenia, fibromyalgia, ADHD, and autism spectrum disorders, among others. Post-extinction training pre-sleep administration of a compound of the invention, subsequent to CBT treatment, can be used to augment the effectiveness of the CBT treatment for these medical conditions.

In one embodiment, subjects suffering from social anxiety disorder undergo weekly cognitive behavioral therapy sessions to treat the affliction. After each therapy session, subjects are administered a therapeutically effective formulation of compounds of the invention on a post-extinction training pre-sleep basis. Relative to subjects treated only via cognitive behavioral therapy, or to subjects treated via cognitive behavioral therapy and a placebo, anxiety associated with social anxiety disorder is expected to be reduced to a greater extent in subjects treated with a combination of cognitive behavioral therapy and achronic administration of a compound of the invention on a post-extinction training pre-sleep basis.

In another embodiment of the invention, a compound of the invention is administered after extinction training only if the extinction training yields positive results on that day. For example, a subject undergoing cognitive behavioral therapy for PTSD is administered a compound of the invention on a post-extinction training only if the cognitive behavioral therapy was deemed to be successful, as determined by the subject and/or therapist. In one aspect, the compound is administered on a post-extinction, pre-sleep basis. In another aspect, a subject undergoing cognitive behavioral therapy for PTSD is administered a compound of the invention on a pre-extinction training. In one aspect, the compound is administered on a pre-extinction, pre-sleep basis. This method may also be useful when applied to treatment of autism spectrum disorders or attention-deficit hyperactivity disorder.

In some embodiments, the invention relates to treating a condition where the treatment comprises re-writing memories. Memories of an event often have an associated emotional component. For example, memories of a traumatic event can cause feelings of grief, guilt, or loss, as well as negative emotional responses such as anger, rage or aggression. Conversely, memories of positive events can cause joy and increase feelings of self-confidence and self-worth. During the period of time when a memory is recalled it can be modified to alter the associations and reduce or alter the emotional reactions to it. In some embodiments, HDAC inhibitors in combination with cognitive behavioral therapy or virtual reality therapy may allow the emotional associations with a memory to be re-written producing a longer term or greater therapeutic benefit.

In another embodiment of the invention, subjects afflicted with anxiety disorders such as PTSD receive extinction training using Eye Movement Desensitization and Reprocessing (EMDR), and subsequently are administered a therapeutically effective dose of a compound of the invention on a post-extinction training pre-sleep basis.

Another form of extinction training is provided by biofeedback, which is particularly useful in enabling subjects to learn to control physiological processes that normally °Ccur involuntarily, such as blood pressure, heart rate, muscle tension, and skin temperature. As used herein, "biofeedback" refers to a technique in which subjects are trained to improve their health by using signals from their own bodies to control their own physiological responses.

In one embodiment of the invention, a subject suffering from chronic pain undergoes biofeedback sessions to help alleviate the pain. Upon the conclusion of each session wherein the subject has made progress in learning/developing responses that reduce the chronic pain, the subject is administered a compound of the invention on a post-extinction training pre-sleep basis in order to consolidate the desired learning.

In another embodiment, a subject suffering from phantom limb syndrome undergoes thermal biofeedback sessions to reduce and hopefully eliminate the symptoms. After each session, the subject is administered a therapeutically effective formulation of a compound of the invention on a post-extinction training pre-sleep basis.

In another embodiment, extinction training can be provided by physical therapy, or virtual reality physical therapy such as virtual reality gait therapy. For example, a stroke victim re-learning how to walk can undergo virtual reality gait therapy, and then be administered a compound of the invention on an achronic, post-extinction training pre-sleep basis.

Another form of extinction training can be provided by pharmacotherapy. For example, a man afflicted with erectile dysfunction can have an extinction learning event based on a positive sexual outcome, including instances wherein the positive sexual outcome was achieved with the pharmacological assistance of a PDE-5 inhibitor such as sildenafil, tadalafil, vardenafil, and/or udenafil. By administering a compound of the invention on a post-extinction training pre-sleep basis to a subject with erectile dysfunction, following a successful sexual outcome wherein the subject utilized sildenafil, the heightened confidence and reduced sexual performance anxiety resulting from a successful outcome can be consolidated in said subject's psyche, thereby facilitating extinction of any deleterious performance anxiety associated with sexual intercourse.

Extinction training does not always require intervention of a trained specialist. Individuals can carry out extinction training on themselves.

Fungal Diseases or Infections

In some aspects, the invention relates to a method for treating, alleviating, and/or preventing a fungal disease or infection comprising administering to a subject a compound of the invention. The invention provides a method for treating, alleviating, and/or preventing a hospital-acquired fungal infections that attack immunocompromised patients including those with HIV and cancer. In one embodiment, the invention provides a method for treating, alleviating, and/or preventing a fungal disease in a subject not suffering from cancer.

Inflammatory Disease

In some aspects, the invention relates to a method for treating, alleviating, and/or preventing an inflammatory disease, including but not limited to stroke, rheumatoid arthritis, lupus erythematosus, ulcerative colitis and traumatic brain injuries (Leoni et al., PNAS, 99(5); 2995-3000 (2002); Suuronen et al. J. Neurochem. 87; 407-416 (2003) and Drug Discovery Today, 10: 197-204 (2005).

Neoplastic Diseases

In some aspects, the invention relates to methods of selectively inducing terminal differentiation, and arresting cell growth and/or apoptosis of neoplastic cells, thereby inhibiting proliferation of such cells. The compounds of the present invention are useful in treating, alleviating, and/or preventing cancer in a subject.

The term "cancer" refers to any cancer caused by the proliferation of neoplastic cells, such as solid tumors, neoplasms, carcinomas, sarcomas, leukemias, lymphomas and the like. In particular, cancers that may be treated, alleviated and/or prevented by the compounds of the invention include, but are not limited to: cardiac cancer, lung cancer, gastrointestinal cancer, genitourinary tract cancer, liver cancer, nervous system cancer, gynecological cancer, hematologic cancer, skin cancer, and adrenal gland cancer.

In some embodiments, the compounds of the invention relate to treating, alleviating, or preventing cardiac cancers selected from sarcoma (angiosarcoma, fibrosarcoma, rhabdomyosarcoma, liposarcoma), myxoma, rhabdomyoma, fibroma, lipoma and teratoma.

In some embodiments, the compounds of the invention relate to treating, alleviating, or preventing lung cancer selected from bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma.

In some embodiments, the compounds of the invention relate to treating, alleviating or preventing gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), and large bowel (adenocarcinoma, tubular adenoma, villous adenoma, hamartoma, leiomyoma).

In some embodiments, the compounds of the invention relate to treating, alleviating, and/or preventing genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

In some embodiments, the compounds of the invention relate to treating, alleviating, and/or preventing liver cancer selected from hepatoma (hepatocellular carcinoma), cholangiocarcinoma, hepatoblastoma, angiosarcoma, hepatocellular adenoma, and hemangioma.

In some embodiments, the compounds of the invention relate to treating, alleviating, and/or preventing bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors.

In some embodiments, the compounds of the invention relate to treating, alleviating, and/or preventing nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In some embodiments, the compounds of the invention relate to treating, alleviating, and/or preventing gynecological cancer selected from uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In some embodiments, the compounds of the invention relate to treating, alleviating, and/or preventing skin cancer selected from malignant melanoma, basal cell carcinoma, squamous cell carcinoma, Karposi's sarcoma, moles dysplastic nevi, lipoma, angioma, dermatofibroma, keloids, and psoriasis.

In some embodiments, the compounds of the invention relate to methods of treating, alleviating, and/or preventing adrenal gland cancer selected from neuroblastoma.

In some embodiments, the instant compounds are useful in the treatment, alleviation, and/or preventing of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

Hematologic Diseases

In some aspects, the invention relates to methods of treating, alleviating, or preventing hematological diseases. Hematologic diseases include abnormal growth of blood cells which can lead to dysplastic changes in blood cells and hematologic malignancies such as various leukemias. Examples of hematologic diseases include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that °Ccurs in adults. Several inherited genetic disorders and immunodeficiency states are associated with an increased risk of AML. These include disorders with defects in DNA stability, leading to random chormosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogeneous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Sickle cell disease is attributable to homozygous inheritance of a single amino acid substitution in the β-globin gene that leads to polymerization of deoxygenated hemoglobin, deformation of red blood cells, microvascular °Cclusion, hemolysis, and consequent disease manifestations, including pain, strokes, and pulmonary complications (Bunn HF, 1997, J. Med. 337:762-769). Abundant biochemical, epidemiological, and clinical evidence have shown that a high level of γ globin, the fetal form of β globin, inhibits the aberrant polymerization of sickle hemoglobin and ameliorates the disease phenotype. The only Food and Drug Administration (FDA)-approved drug for sickle cell disease, hydroxyurea, causes significant induction of fetal hemoglobin, decreased disease severity, and benefits overall mortality (Letvin et al., 1984, N Engl J Med 310:869-873; Platt O S, et al., 1984, J Clin Invest 74:652-656; Charache S, et al., 1995, N Engl J. Med 332: 317-1322; Steinberg M H, et al., 2003, JAMA 289:1645-1651). Nevertheless, hydroxyurea has bone marrow-suppressive effects and is ineffective in a significant portion of patients (Charache S, et al.; Steinberg M H, et al., 2003; Steinberg M H, 1999, N Engl J. Med 340:1021-1030). A drug that induces fetal hemoglobin more substantially with less myelosuppression would be expected to have greater therapeutic utility in sickle cell disease.

Transcriptional regulation of the human globin gene locus has been investigated intensively. Gamma-globin gene expression is influenced by transcription factors (GATA-1, EKLF, NF-E4p22, Ikaros) and chromatin modifying enzymes [SWI/SNF complex, HATs, and histone deacetylase (HDACs)] as part of multiprotein complexes, and a unique, dynamic chromatin structure termed the β-globin active chromatin hub (βACH) (8-11). Polymorphisms in BCL11A, a transcriptional repressor, alter baseline fetal hemoglobin levels, and a multiprotein complex containing BCL11a binds to the β-globin locus, resulting in repression of γ-globin expression (Menzel S, et al., 2007, Nat Genet 39:1197-1199; Lettre G, et al., 2008, Proc Natl Acad Sci USA 105:11869-11874;

Sankaran V G, et al., 2008, Science 322:1839-1842; Uda M, et al., 2008, Proc NATL Acad Sci USA 105:1620-1625; Sankaran V G, et al., 2009, Nature 460:1093-1097). Despite this granularity, discrete targets amenable to ligand discovery efforts have not been identified and functionally validated.

The induction of fetal hemoglobin is a validated strategy to improve symptoms and complications of sickle cell disease. The development of targeted therapies has been limited by the absence of discrete druggable targets. Bradner et al., 2010, PNAS, 107:28, 12617-12622 has developed a unique bead-based strategy for the identification of inducers of fetal hemoglobin transcripts in primary human erythroid cells, which includes a small-molecule screen of bioactive compounds that have been identified to have remarkable class-associated activity among histone deacetylase (HDAC) inhibitors. Using a chemical genetic strategy combining focused libraries of biased chemical probes and reverse genetics by RNA interference, Bradner et al. identified HDAC1 and HDAC2 as molecular targets mediating fetal hemoglobin induction. Isoform-selective inhibitors of HDAC1 and HDAC2 are targets for the treatment of sickle cell disease.

Pharmaceutical Compositions

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of any of the HDAC isoforms described herein.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^{30}(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the disorder, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents. In other embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Those additional agents may be administered separately from a provided combination therapy, as part of a multiple dosage regimen. Alternatively, those agents may be part of a single dosage form, mixed together with a compound of this invention in a single composition. If administered as part of a combination therapy, the two therapeutic agents may be submitted simultaneously, sequentially or within a period of time from one another normally within about one through twelve hours from one another. For example, one therapeutic agent can be administered within about one, two, three, four, five, six, seven, eight, nine, ten, eleven, or twelve hours from the other therapeutic agent or agents used in the combination therapy.

Combination therapy can be used for any of the therapeutic indications described herein. In one aspect, the invention provides a method, wherein the method is a combination therapy further comprising administering to the subject (1) a pharmaceutically active ingredient or exposing the subject to (2) cognitive behavioral therapy (CBT), (3) psychotherapy, (4) behavioral exposure treatments, (5) virtual reality exposure (VRE) or (6) cognitive remediation therapy or (7) any combination thereof. In one aspect, the invention provides a combination therapy for treating, alleviating, and/or preventing post-traumatic stress disorder (PTSD) or Alzheimer's disease in a subject comprising administering to the subject in need thereof an effective amount of (1) a compound of the invention or a pharmaceutically acceptable salt, hydrate, solvate, or prodrug thereof and (2) a pharmaceutically active ingredient administered selected from Aricept®, memantine, and galantamine.

In one aspect, the invention provides a method of treating extinction learning disorders in a subject in need thereof comprising administering to the subject an effective amount of a compound of the invention or a pharmaceutically acceptable salt, hydrate, solvate, or prodrug thereof. In one aspect, the extinction learning disorder is fear extinction deficit. In one aspect, the extinction learning disorder is post-traumatic stress disorder. In one aspect, the method is a combination therapy for treating extinction learning disorders in a subject in need thereof comprising administering to the subject (1) an effective amount of a compound of the invention or a pharmaceutically acceptable salt, hydrate, solvate, or prodrug thereof and (2) exposing the subject to cognitive behavioral therapy (CBT), psychotherapy, behavioral exposure treatments, virtual reality exposure (VRE) or cognitive remediation therapy.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

Another aspect of the invention relates to inhibiting HDAC activity in a biological sample or a patient, which method comprises administering to the patient, or contacting said biological sample with a compound described herein, or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where HDAC plays a role.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Information

Spots were visualized by UV light (254 and 365 nm). Purification by column and flash chromatography was carried out using silica gel (200-300 mesh). Solvent systems are reported as the ratio of solvents.

NMR spectra were recorded on a Bruker 400 (400 MHz) spectrometer. $^1$H chemical shifts are reported in δ values in ppm with tetramethylsilane (TMS, =0.00 ppm) as the internal standard.

LCMS spectra were obtained on an Agilent 1200 series 6110 or 6120 mass spectrometer with ESI (+) ionization mode.

Example 1

Synthesis of Compound 102

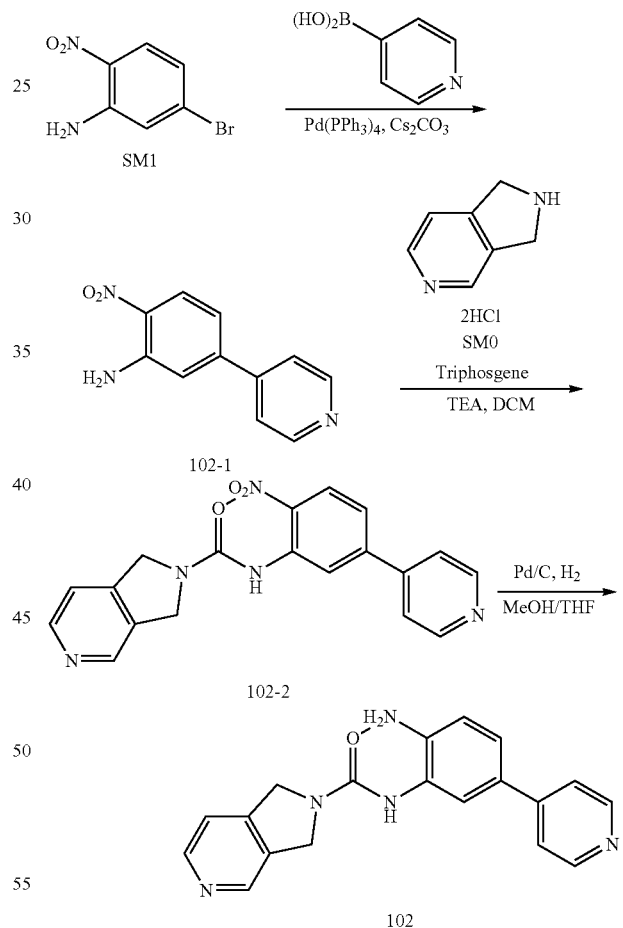

Synthesis of 102-1. A mixture of SM1 (4.32 g, 20.0 mmol), Pyridine-4-boronic acid (4.91 g, 40.0 mmol), $Cs_2CO_3$ (13.00 g, 40.0 mmol) and $Pd(PPh_3)_4$ (2.30 g, 2.0 mmol) in dioxane (100 mL) was purged by $N_2$ and stirred at 95° C. overnight. After cooling to room temperature, the solvent was removed in vacuo. The residue was purified by column chromatography on silica gel (petroleum ether: ethyl acetate (PE:EA)=5:1~1:1) to give 102-1 (2.50 g, 58%) as a yellow solid.

Synthesis of 102-2. To a solution of 102-1 (215 mg, 1.0 mmol), trimethylamine (TEA; 810 mg, 8.0 mmol) in dichloromethane (DCM; 10 mL) was added triphosgene (330 mg, 1.1 mmol) at ice bath. The mixture as warmed to room temperature and stirred for 3 h. TEA (202 mg, 2.0 mmol) and SM0 (230 mg, 1.2 mmol) was then added. The resulting solution was heated at 50° C. for 2 h. The mixture was cooled and diluted with DCM. The resultant was washed with brine, dried over $Na_2SO_4$ and concentrated in vacuo. The residue was purified by column chromatography on silica gel (DCM:MeOH=100:1~35:1) to give 102-2 (140 mg, 39%) as a yellow solid.

Synthesis of 102 A mixture of 102-2 (140 mg, 0.38 mmol), Pd/C (30 mg) in methanol (5 mL) and tetrahydrofuran (THF; 5 mL) was stirred at room temperature under $H_2$ atmosphere for 2 h. Pd/C was removed by filtraction through the Celite. The filtrate was concentrated and the residue was recrystallized with methanol to give 102 (50 mg, 39%) as a brown solid.

Compounds 100, 101, 104, 105, 106, 107, 108, 109, 110, 115, 136 and 144 were synthesized in a similar manner using the appropriately substituted amine variant of 102.

Compound 100. 62 mg, 42%, a brown solid.
Compound 101. 53 mg, 32%, a yellow solid.
Compound 104. 80 mg, 29%, a yellow solid.
Compound 105. 100 mg, 22%, a white solid.
Compound 106. 70 mg, 19%, a white solid.
Compound 107. 96 mg, 52%, a white solid.
Compound 108. 36 mg, 14%, a brown solid.
Compound 109. 26 mg, 9%, a yellow solid.
Compound 110. 150 mg, 53%, a white solid.
Compound 115. 50 mg, 27%, a yellow solid.
Compound 136. 60 mg, 29%, a white solid.
Compound 144. 65 mg, 54%, a yellow solid.

Example 2

Synthesis of Compound 103

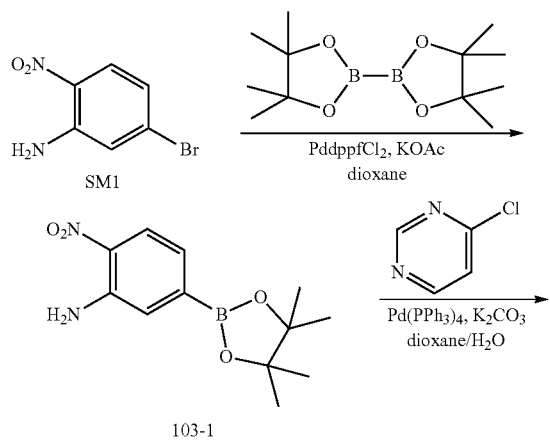

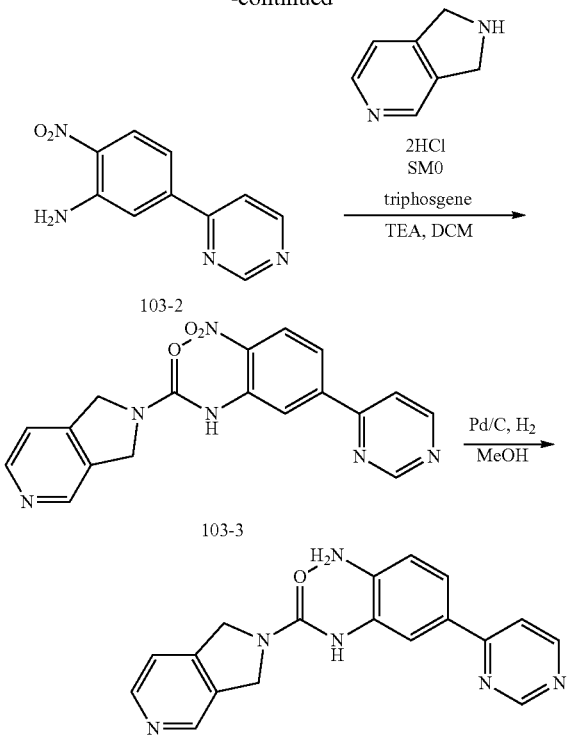

Synthesis of 103-1. A mixture of SM-1 (1.10 g, 5.0 mmol), KOAc (1.47 g, 15.0 mmol), bis(pinacolato)diboron (2.10 g, 8.0 mmol) and Pd(dppf)Cl₂ in dioxane (40 mL) was purged by $N_2$ and stirred at 95° C. for 4 h. After cooling to room temperature, the mixture was diluted with water and the resultant was extracted with EA. The combined organic layer was washed with brine, dried over anhydrous $Na_2SO_4$ and concentrated to give 103-1 (1.50 g) as a crude product, which was used directly in the next step without further purification.

Synthesis of 103-2. A mixture of 103-1 (1.50 g, 5.0 mmol), 4-chloropyrimidine (0.90 g, 6.0 mmol), $K_2CO_3$ (2.10 g, 15.0 mmol) and Pd(PPh₃)₄ (580 mg, 0.5 mmol) in dioxane/H₂O (40 mL/15 mL) was purged by $N_2$ and stirred at 95° C. overnight. After the reaction was completed according to LCMS, water was added and the mixture was extracted with EA. The combined organic layer was washed with brine, dried over anhydrous $Na_2SO_4$ and concentrated. The residue was purified by column chromatography on silica gel (PE:EA=4:1) to give 103-2 (750 mg, 69%) as a yellow solid.

Synthesis of 103-3. To a solution of 103-2 (220 mg, 1.0 mmol), TEA (810 mg, 8.0 mmol) in DCM (10 mL) was added triphosgene (330 mg, 1.1 mmol) under ice bath. The solution was warmed to room temperature and stirred for 3 hrs. TEA (202 mg, 2.0 mmol) and SM-0 (230 mg, 1.2 mmol) was then added. The resulting solution was heated at 50° C. for 2 h. The mixture was cooled and diluted with DCM. The resultant was washed with brine, dried over $Na_2SO_4$ and concentrated. The residue was purified by column chromatography on silica gel (DCM:MeOH=100:1~30:1) to give 103-3 (120 mg, 33%) as a yellow solid.

Synthesis of 103. A solution of 103-3 (120 mg, 0.33 mmol), Pd/C (30 mg) in methanol (5 mL) and THF (5 mL) was stirred at room temperature under H₂ atmosphere for 2 hr. Pd/C was removed by filtration through the celite. The filtrate was concentrated and the residue was purified by Pre-HPLC to give 103 (30 mg, 39%) as a yellow solid.

Example 3

Synthesis of Compound 122

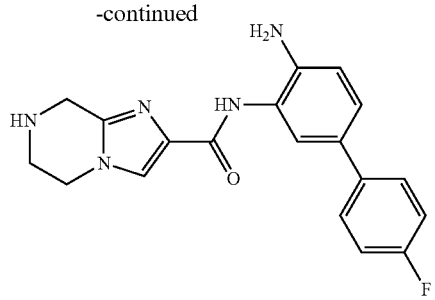

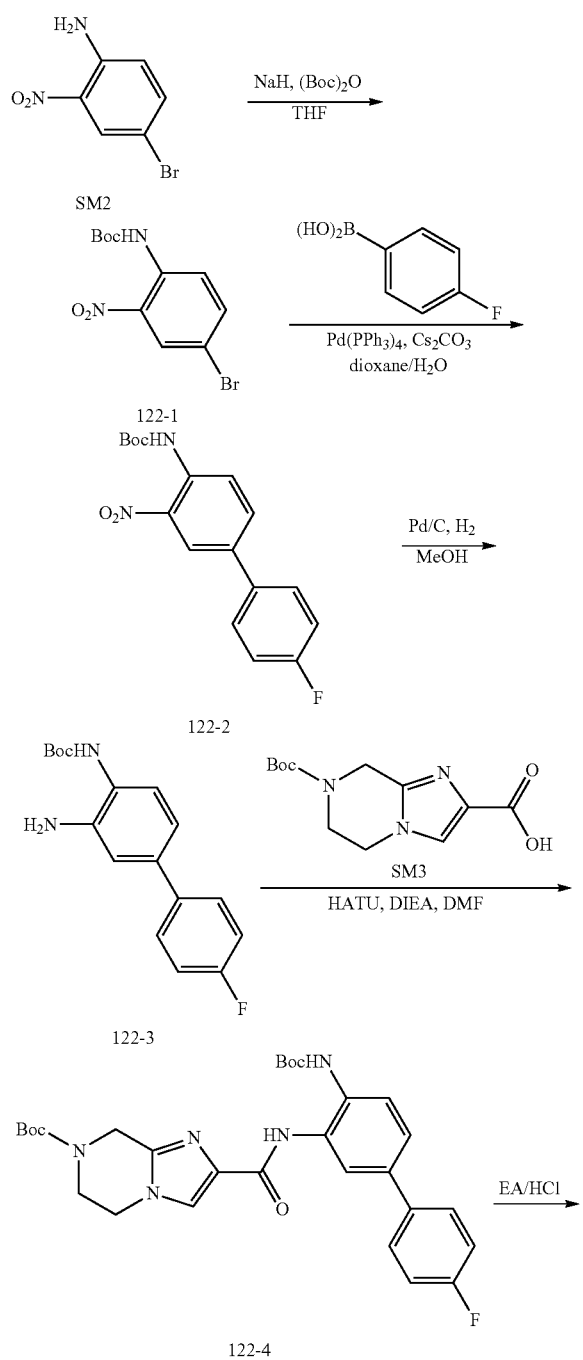

Synthesis of 122-1. To a solution of SM-2 (5.00 g, 23.0 mmol) in THF (150 mL) was added NaH (1.80 g, 46.0 mmol) under ice bath. The solution was stirred for 1 h at the same temperature and then (Boc)₂O (6.00 g, 27.6 mmol) was added. The resulting solution was warmed to room temperature and continued to stir for 2 h. After the reaction was completed, the solvent was concentrated in vacuo. The residue was dissolved with EtOAc (100 mL) and the resulting solution was washed with brine (30 mL×3). The organic layer was dried over anhydrous Na₂SO₄ and concentrated in vacuo. The residue was purified by column chromatography on silica gel (PE:EtOAc=100:1~50:1) to give 122-1 (4.00 g, 55%) as a yellow solid.

Synthesis of 122-2. To a mixture of 122-1 (4.00 g, 12.7 mmol), 4-fluorophenylboronic acid (2.67 g, 19.1 mmol) and Cs₂CO₃ (4.11 g, 25.4 mmol) in dioxane/H₂O (80 mL/16 mL) was added Pd(PPh₃)₄(1.47 g, 1.3 mmol) under N₂ atmosphere. The mixture was stirred at 95° C. for 2 h and then concentrated in vacuo. The residue was dissolved with EtOAc (100 mL) and the resulting mixture was washed with brine (30 mL×3). The combined organic layers were dried over anhydrous Na₂SO₄ and concentrated in vacuo. The residue was purified by column chromatography on silica gel (PE:EtOAc=100:1-20:1) to give 122-2 (3.00 g, 72%) as a yellow solid.

Synthesis of 122-3. A mixture of 122-2 (3.00 g, 9.0 mmol) and Pd/C (0.50 g) in MeOH (60 mL) was stirred at room temperature for 2 h under H₂ atmosphere. Pd/C was removed by filtration through the celite. The filtrate was concentrated to give 122-3 (1.70 g, 62%) as a yellow solid.

Synthesis of 122-4. A mixture of 122-3 (1.70 g, 5.6 mmol), SM-3 (1.36 g, 5.1 mmol), DIPEA (1.32 g, 10.2 mmol) and HATU (2.91 g, 7.7 mmol) in DMF (30 mL) was stirred at room temperature overnight. The mixture was diluted with water (100 mL) and then extracted with EtOAc (40 mL×3). The combined organic layer was washed with brine (40 mL×3), dried over anhydrous Na₂SO₄ and concentrated in vacuo. The residue was purified by column chromatography on silica gel (PE:EtOAc=10:1~2:1) to give 122-4 (2.80 g) as a crude solid.

Synthesis of 122. A solution of 122-4 (2.80 g) in 4N EA/HCl (56 mL) was stirred at room temperature for 2 h and then concentrated in vacuo. The residue was diluted with water (5 mL) and the resultant was adjusted to pH=9~10 by saturated Na₂CO₃ solution. The formed precipitate was collected by filtration and dried to give 122 (1.40 g, 78%, over two steps) as a yellow solid.

Compounds 128, 131, 147, 150, 152 and 175 were synthesized in a similar manner using the appropriately substituted acid variant of 122.

Compound 128. 12 mg, 6%, a white solid.
Compound 131. 80 mg, 43%, a white solid.

Compound 147. 30 mg, 46%, a white solid.
Compound 150. 80 mg, 71%, a pink solid.
Compound 152. 30 mg, 28%, a yellow solid.
Compound 175. 60 mg, 31%, a pink solid.
Compounds 123 and 174 were synthesized in a similar manner using pyridin-4-ylboronic acid and the appropriately substituted acid variant of 122.
Compound 123. 100 mg, 44%, as a yellow solid.
Compound 174. 100 mg, 37%, a yellow solid.

Example 4

Synthesis of Compounds 124, 114, and 120 purified by column chromatography on silica gel (PE:EtOAc=50:1~5:1) to give 120-0 (10.0 g, 93%) as a yellow solid.

Synthesis of 120-1. To a solution of 120-0 (740 mg, 3.2 mmol), TEA (2.60 g, 25.0 mmol) in DCM (50 mL) was added triphosgene (1.05 g, 3.5 mmol) under ice bath. The solution was warmed to room temperature and stirred for 3 hrs. TEA (700 mg, 7.0 mmol) and SM-4 (745 mg, 3.5 mmol) was then added. The resulting solution was heated at 50° C. for 2 h. The solution was cooled and diluted with DCM. The resultant was washed with brine, dried over anhydrous $Na_2SO_4$ and concentrated in vacuo. The residue was purified by column chromatography on silica gel (DCM:MeOH=200:1~50:1) to give 120-1 (1.0 g, 67%) as a yellow solid.

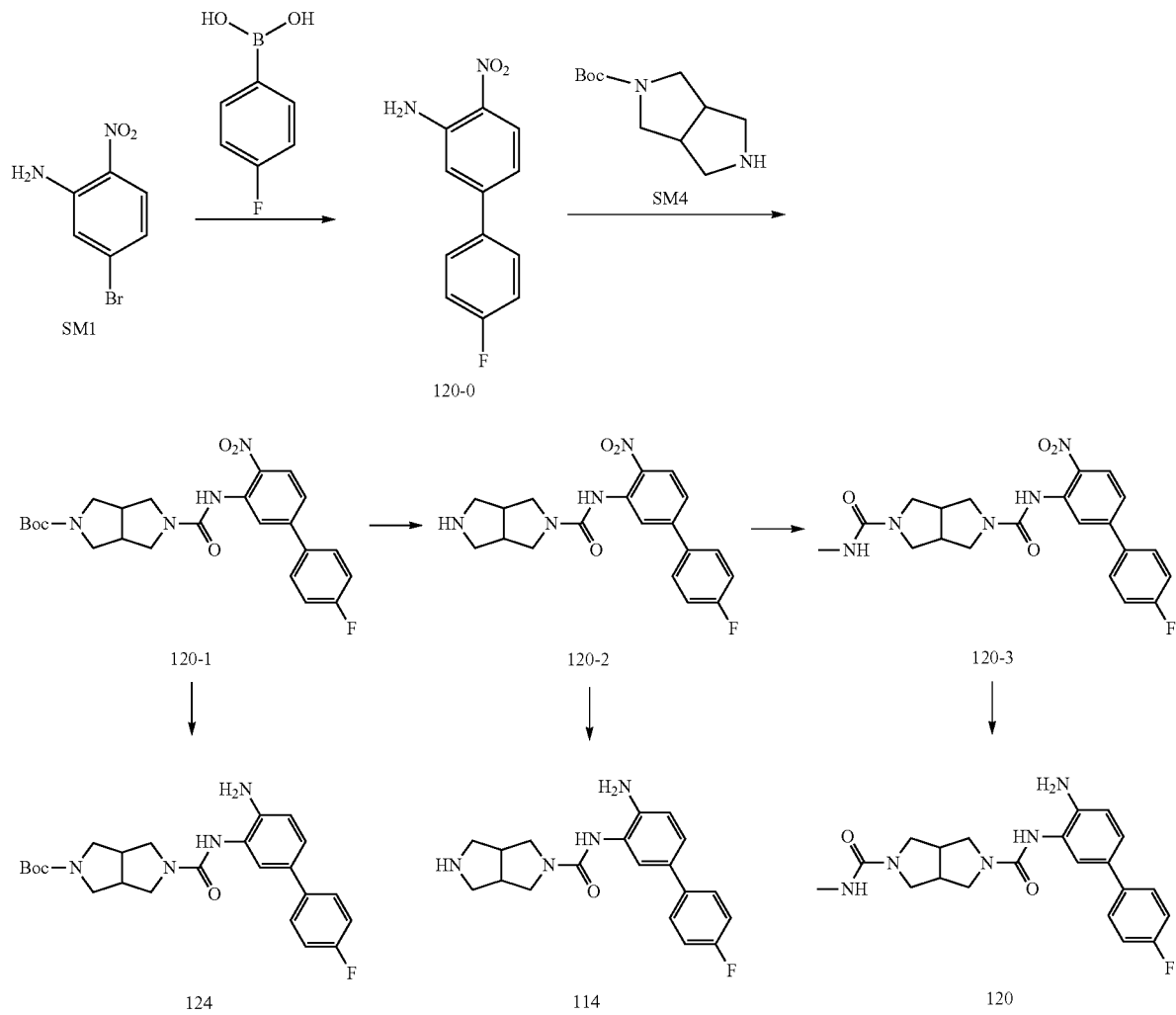

Synthesis of 120-0. To a mixture of SM-1 (10.0 g, 46.3 mmol), 4-fluorophenylboronic acid (6.8 g, 48.6 mmol) and $Cs_2CO_3$ (45.3 g, 138.9 mmol) in dioxane/$H_2O$ (200 mL/40 mL) was added Pd(PPh$_3$)$_4$ (5.3 g, 4.6 mmol) under $N_2$ atmosphere. The mixture was stirred at 95° C. for 2 h and then concentrated in vacuo. The residue was dissolved with EtOAc (300 mL) and the solution was washed with brine (100 mL×3). The organic layer was dried over anhydrous $Na_2SO_4$ and then concentrated in vacuo. The residue was Synthesis of 124. A solution of 120-1 (100 mg, 0.21 mmol), Pd/C (30 mg) in methanol (5 mL) was stirred at room temperature under $H_2$ atmosphere for 2 h. Pd/C was removed by filtration through the celite. The filtrate was concentrated in vacuo and the residue was recrystallized with PE/EA to give 124 (40 mg, 43%) as a white solid.

Synthesis of 120-2. A mixture of 120-1 (520 mg, 1.1 mmol) in TFA/DCM (3 mL/6 mL) was stirred at room temperature for 2 h. The solvent was removed in vacuo. The residue was dissolved with water and the resulting solution was adjusted to pH>7 by saturated NaHCO$_3$ solution. The resultant solution was extracted with DCM. The combined organic layers were washed with brine, dried over anhydrous Na$_2$SO$_4$ and concentrated in vacuo to give 120-2 (380 mg, 93%) as a yellow solid.

Synthesis of 114. A solution of 120-2 (160 mg, 0.4 mmol), Pd/C (30 mg) in methanol (10 mL) was stirred at room temperature under H$_2$ atmosphere for 2 h. Pd/C was removed by filtration through the celite. The filtrate was concentrated in vacuo and the residue was recrystallized with PE/EA to give pure 114 (80 mg, 55%) as a gray solid.

Synthesis of 120-3. To a solution of 120-2 (180 mg, 0.5 mmol), TEA (100 mg, 1.0 mmol) in DCM (10 mL) was added triphosgene (49 mg, 0.2 mmol) under ice bath. The solution was warmed to 0° C. for 1 h and then MeNH$_2$.HCl (33 mg, 0.5 mmol) was added. The mixture was warmed to room temperature and stirred for 40 h. The reaction mixture was quenched with saturate NH$_4$Cl. The resultant was extracted with DCM. The combined organic layer was washed with brine, dried over anhydrous Na$_2$SO$_4$ and concentrated in vacuo. The residue was purified by column chromatography on silica gel (DCM:MeOH=200:1~50:1) to give 120-3 (180 mg, 86%) as a yellow solid.

Synthesis of 120. A solution of 120-3 (180 mg, 0.43 mmol), Pd/C (30 mg) in methanol (10 mL) was stirred at room temperature under H$_2$ atmosphere for 2 h. Pd/C was removed by filtration through the celite. The filtrate was concentrated and the residue was recrystallized with methyl tert-butyl ether (MTBE) to give 120 (80 mg, 47%) as a gray solid.

Compounds 111, 112, 119, 127, 137, 138, 143, 148, 153, 161, 166, 171, 172 and 173 were synthesized in a similar manner using the appropriately substituted amine variant of 124.

Compound 111. 100 mg, 36%, a white solid.
Compound 112. 120 mg, 96%, a yellow solid.
Compound 119. 120 mg, 52%, a light yellow solid.
Compound 127. 46 mg, 20%, a gray solid.
Compound 137. 26 mg, 28%, a white solid.
Compound 138. 9 mg, 7%, a gray solid.
Compound 143. 60 mg, 32%, a white solid.
Compound 148. 100 mg, 41%, a white solid.
Compound 153. 60 mg, 32%, a white solid.
Compound 161. 60 mg, 32%, a white solid.
Compound 166. 30 mg, 36%, a yellow solid.
Compound 171. 150 mg, 77%, a gray solid.
Compound 172. 55 mg, 39%, a white solid.
Compound 173. 135 mg, 48%, a white solid.

Compounds 113, 118, 169 and 170 were synthesized in a similar manner using the appropriately substituted amine variant of 114.

Compound 113. 150 mg, 39%, a white solid.
Compound 118. 30 mg, 17%, a light yellow solid.
Compound 169. 30 mg, 39%, a white solid.
Compound 170. 150 mg, 64%, a red solid.

Example 5

Synthesis of Compound 158

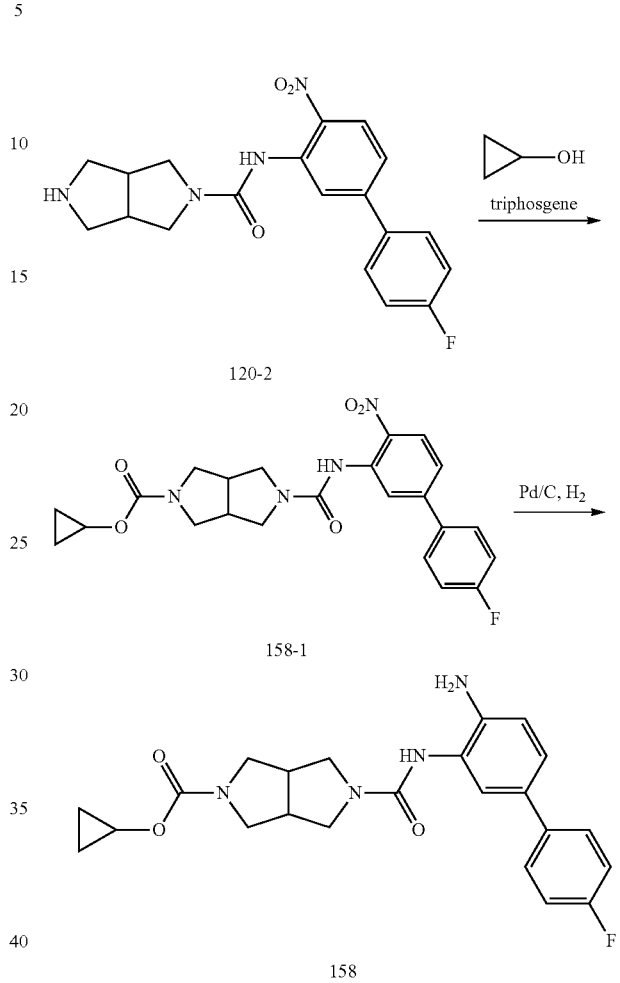

Synthesis of 158-1. To a solution of cyclopropanol (58 mg, 1.0 mmol), TEA (606 mg, 6.0 mmol) in DCM (10 mL) was added triphosgene (297 mg, 1 mmol) under ice bath. The solution was warmed to room temperature and stirred for 1 h. TEA (202 mg, 2.0 mmol) and 120-2 (370 mg, 1.0 mmol) were then added. The resulting solution was heated at 50° C. for 1 h. After cooling to room temperature, the solution was diluted with DCM. The resulting solution was washed with brine. The organic layer was dried over anhydrous Na$_2$SO$_4$ and concentrated in vacuo. The residue was purified by column chromatography on silica gel (DCM: MeOH=50:1~20:1) to give 158-1 (150 mg, 33%) as a gray solid.

Synthesis of 158. A solution of 158-1 (150 mg, 0.33 mmol), Pd/C (30 mg) in methanol (10 mL) was stirred at room temperature under H$_2$ atmosphere for 3 h. Pd/C was removed by filtration through the celite. The filtrate was concentrated in vacuo. The residue was purified by Pre-HPLC to give 158 (56 mg, 40%) as a white solid.

Compound 159 was synthesized by a similar procedure using the appropriately substituted alcohol variant of 158.

Compound 159. 57 mg, 34%, a white solid.

Example 6

Synthesis of Compound 121

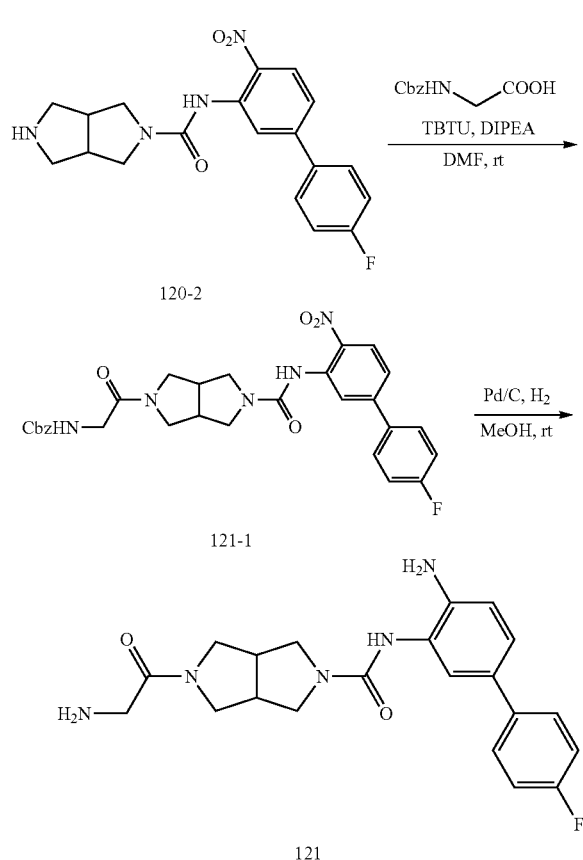

Example 7

Synthesis of Compound 154

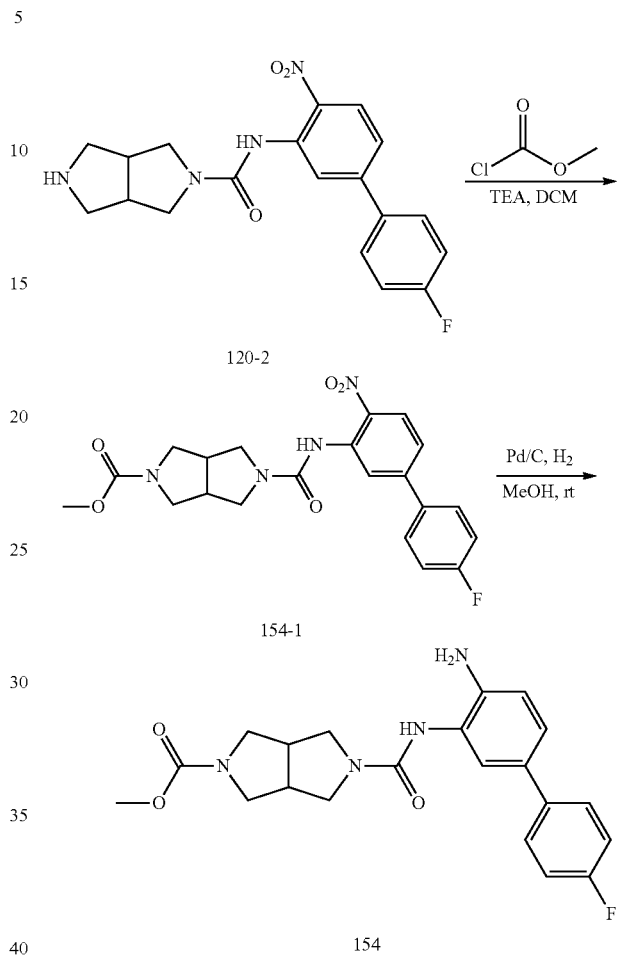

Synthesis of 121-1. A mixture of 120-2 (150 mg, 0.4 mmol), Cbz-Glycine (92 mg, 0.44 mmol), O-(Benzotriazol-1-yl)-N,N,N',N'-tetramethyluronium tetrafluoroborate (TBTU; 154 mg, 0.48 mmol) and DIPEA (103 mg, 0.8 mmol) in DMF (5 mL) was stirred at room temperature for 3 h. Water was added and the mixture was extracted with EA. The combined organic layers were washed with brine, dried over anhydrous $Na_2SO_4$ and concentrated in vacuo. The residue was purified by column chromatography on silica gel (DCM:MeOH=60:1) to give 121-1 (201 mg, 90%) as a yellow solid.

Synthesis of 121. A solution of 121-1 (200 mg, 0.356 mmol), Pd/C (50 mg) in methanol (15 mL) was stirred at room temperature under $H_2$ atmosphere for 2 h. Pd/C was removed by filtration through the celite. The filtration was concentrated in vacuo and the residue was purified by prep. HPLC to give pure 121 (90 mg, 47%) as a white solid.

Compound 117 and 125 were synthesized by a similar procedure using the corresponding amine precursor and appropriately substituted acid variant of 121.

Compound 117. 80 mg, 41%, a white solid.
Compound 125. 90 mg, 47%, a white solid Synthesis of 154-1. To a solution of 120-2 (200 mg, 0.54 mmol), TEA (111 mg, 1.1 mmol) in DCM (5 mL) was added methyl chloroformate (61 mg, 0.65 mmol) under ice bath. The solution was warmed to room temperature and stirred for 1 h. After the reaction was completed, the solution was diluted with DCM. The resultant was washed with brine, dried over $Na_2SO_4$ and concentrated. The residue was purified by column chromatography on silica gel (DCM:MeOH=50:1~20:1) to give 154-1 (210 mg, 91%) as a yellow solid.

Synthesis of 154. A solution of 154-1 (210 mg, 0.49 mmol), Pd/C (40 mg) in methanol (5 mL) was stirred at room temperature under $H_2$ atmosphere for 2 h. Pd/C was removed by filtration through the celite. The filtration was concentrated in vacuo and the residue was purified by prep. HPLC to give 154 (77 mg, 36%) as a white solid.

Compounds 116, 155, 156, 157 and 160 were synthesized by a similar procedure using the corresponding amine precursor and appropriately substituted acyl chloride variant of 154.

Compound 116. 70 mg, 22%, a white solid.
Compound 155. 80 mg, 36%, a white solid.
Compound 156. 84 mg, 35%, a white solid.
Compound 157. 85 mg, 36%, a white solid.
Compound 160. 80 mg, 33%, a white solid.

Example 8

Synthesis of Compound 126

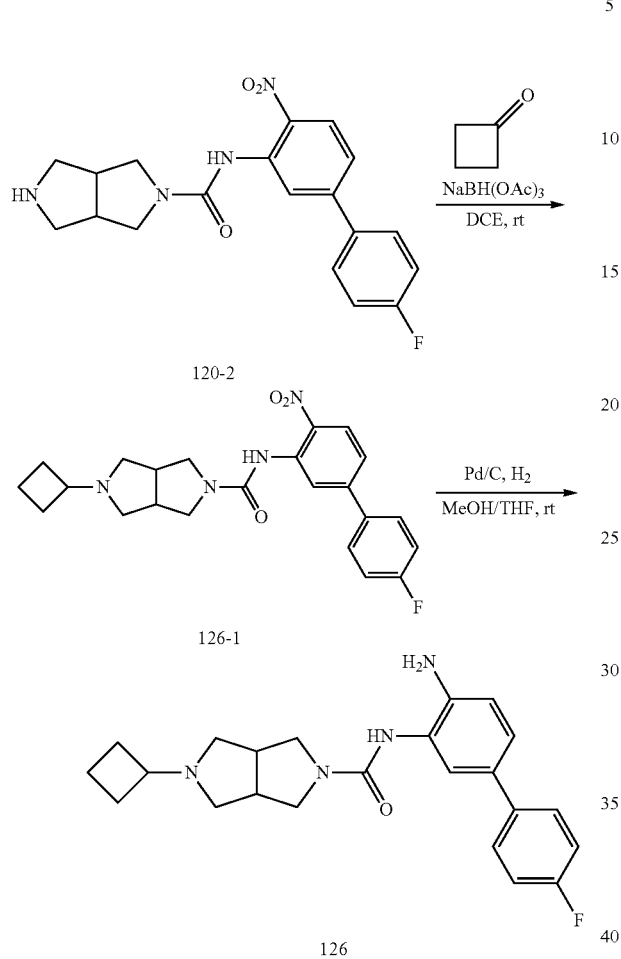

Synthesis of 126-1. A mixture of 120-2 (110 mg, 0.3 mmol), cyclobutanone (24 mg, 0.33 mmol) and NaBH(OAc)₃ (190 mg, 0.9 mmol) in dichloroethane (DCE; 10 mL) was stirred at room temperature overnight. Water was added and the mixture was extracted with dichloromethane. The combined organic layer was washed with brine, dried over anhydrous Na₂SO₄ and concentrated in vacuo. The residue was purified by column chromatography on silica gel (DCM:MeOH=30:1) to give 126-1 (100 mg, 78%) as a yellow solid.

Synthesis of 126. A solution of 126-1 (100 mg, 0.234 mmol), Pd/C (30 mg) in MeOH/THF (5/5 mL) was stirred at room temperature under H₂ atmosphere for 2 h. Pd/C was removed by filtration through the celite. The filtration was concentrated in vacuo and the residue was triturated in PE/EA to give 126 (50 mg, 54%) as a yellow solid.

Compounds 129, 164 and 165 were synthesized by a similar procedure using the corresponding amine precursor.

Compound 129. 45 mg, 37%, a yellow solid.

Compound 164. 10 mg, 9%, a white solid.

Compound 165. 10 mg, 13%, a yellow solid.

Example 9

Synthesis of Compound 130

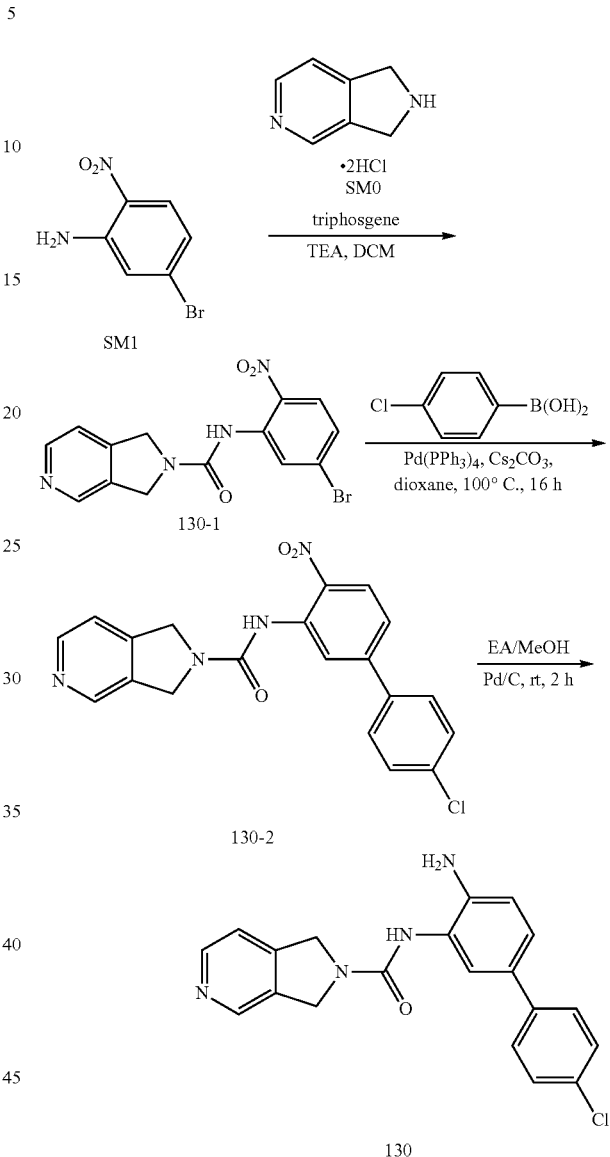

Synthesis of 130-1. To a solution of SM-1 (1.08 g, 5.0 mmol), TEA (3.03 g, 30.0 mmol) in DCM (20 mL) was added triphosgene (1.49 g, 5.0 mmol) under ice bath. The solution was warmed to room temperature and stirred for 1 h. TEA (2.02 g, 20.0 mmol) and SM-0 (965 mg, 5.0 mmol) was then added. The resulting solution was heated at 50° C. for 1 h. After cooling to room temperature, the solution was diluted with DCM. The resultant was washed with brine, dried over anhydrous Na₂SO₄ and concentrated in vacuo. The residue was purified by column chromatography on silica gel (DCM:MeOH=100:1~30:1) to give 130-1 (900 mg, 50%) as a yellow solid.

Synthesis of 130-2. To a solution of 130-1 (80 mg, 0.22 mmol) in dioxane (1.0 mL) was added 4-chlorophenylboronic acid (51 mg, 0.33 mmol), Cs₂CO₃ (143 mg, 0.44 mmol) and Pd(PPh₃)₄ (15 mg, 13 μmol) successively. The mixture was refluxed under argon atmosphere for 16 h. The solvent was removed in vacuo. The residue was purified by column chromatography on silica gel (DCM:MeOH=80:1) to afford 130-2 (40 mg, 46%) as a yellow solid.

Synthesis of 130. To a solution of 130-2 (40 mg, 0.10 mmol) in EA/MeOH (1.0 mL/1.0 mL) was added Pd/C (10 mg). The mixture was stirred under $H_2$ atmosphere for 2 h. Pd/C was removed by filtration through the celite. The filtrate was concentrated and the residue was purified by prep-HPLC to afford 130 (15 mg, 41%) as a white solid.

Compounds 132, 133, 134, 135, 139, 140, 141, 142, 145, 146, 149, 151, 162, 163, 167 and 168 were synthesized by a similar procedure using the appropriately substituted aryl boronic acid variant of 130.

Compound 132. 10 mg, 27%, a white solid.
Compound 133. 10 mg, 27%, a white solid.
Compound 134. 12 mg, 52%, a white solid.
Compound 135. 10 mg, 31%, a white solid.
Compound 139. 12 mg, 26%, a white solid.
Compound 140. 15 mg, 33%, a white solid.
Compound 141. 7 mg, 25%, a white solid.
Compound 142. 10 mg, 54%, a white solid.
Compound 145. 30 mg, 47%, a white solid.
Compound 146. 5 mg, 28%, a white solid.
Compound 149. 10 mg, 27%, a white solid.
Compound 151. 10 mg, 22%, a white solid.
Compound 162. 18 mg, 32%, a white solid.
Compound 163. 10 mg, 43%, a white solid.
Compound 167. 15 mg, 52%, a yellow solid.
Compound 168. 7 mg, 39%, a white solid.

Example 10

Reporter Displacement Assay

HDAC2 containing a C-terminal HIS-Tag (Proteros) and fluorescently-labeled anti-HIS-antibody are diluted in one vial in assay buffer 50 mM Tris, pH 8.0, 1 mM DTT, 150 mM NaCl, and 0.01% Tween20. Components are pre-incubated for 30 min, then a small volume of reporter probe (Proteros) is added from a highly concentrated stock and incubation is continued for another 30 min. Final concentrations after adding the reporter probe amount to 20 nM HDAC2, 4 nM antibody, and 180 nM probe.

Ten µl/well of pre-formed complex are transferred into 384 well assay plates (Corning). Compounds to be profiled are serially diluted from $1\times10^1$-$5.7\times10^5$ mM in DMSO and 60 nl are added to assay plates by pintool transfer (CybiWell, Cybio). Fluorescence intensity signal is read after 4 h in a Pherastar FS (BMG Labtech) at 337/665 nm.

For $K_d$ determination, percent probe displacement values are calculated for each compound concentration and plotted against the compound concentration. $IC_{50}$-like values (corresponding to 50% probe displacement) are calculated using standard fitting algorithms. Since the reporter probe is used at a concentration reflecting its own $K_d$ value, compound $K_d$ values can be calculated according to the Cheng Prusoff equation.

The results of this assay for compounds useful in this invention are reported in Table 2, below. In the table, "A" indicates a $K_d$ value of less than 0.1 µM; "B" a $K_d$ value of between 0.1 µM and 0.5 µM; "C" a $K_d$ value of greater than 0.5 µM and less than or equal to 5.0 µM; and "D" a $K_d$ value of greater than 5.0 µM.

TABLE 2

HDAC1 and HDAC2 $K_d$ Values for Exemplary Compounds Useful in the Invention

| Compound No. | HDAC2 $K_d$ (uM) | HDAC2 residence time (min) | HDAC1 $K_d$ (uM) | HDAC1 residence time (min) |
|---|---|---|---|---|
| 100 | 0 | 0 | B | 470 |
| 101 | B | 1932 | A | 906 |
| 102 | B | 1410 | A | 1238 |
| 103 | C | 1961 | C | 330 |
| 104 | D | 0 | D | 0 |
| 105 | D | 0 | D | 0 |
| 106 | D | 0 | D | 0 |
| 107 | D | 0 | D | 0 |
| 108 | D | 0 | D | 0 |
| 109 | D | 0 | D | 0 |
| 110 | D | 0 | D | 0 |
| 111 | D | 61 | D | 34 |
| 112 | D | 38 | D | 9 |
| 113 | D | 0 | D | 0 |
| 114 | C | 1468 | D | 127 |
| 115 | C | 0 | C | 98 |
| 116 | D | 30 | D | 16 |
| 117 | C | 36 | D | 29 |
| 118 | B | 636 | A | 1175 |
| 119 | B | 2151 | B | 1504 |
| 120 | B | 2359 | A | 1550 |
| 121 | C | 869 | B | 587 |
| 122 | B | 1950 | A | 1483 |
| 123 | B | 1606 | B | 1046 |
| 124 | B | 1789 | B | 584 |
| 125 | B | 1408 | A | 788 |
| 126 | B | 2624 | A | 937 |
| 127 | B | 2541 | A | 1518 |
| 128 | B | 1505 | A | 1727 |
| 129 | B | 1696 | A | 724 |
| 130 | B | 1300 | A | 1083 |
| 131 | B | 1199 | B | 695 |
| 132 | C | 111 | C | 47 |
| 133 | B | 1463 | A | 1303 |
| 134 | B | 790 | B | 192 |
| 135 | B | 1211 | B | 353 |
| 136 | B | 1535 | A | 941 |
| 137 | B | 1379 | B | 552 |
| 138 | B | 2370 | B | 724 |
| 139 | A | 2256 | A | 1454 |
| 140 | C | 341 | C | 34 |
| 141 | D | 0 | D | 1346 |
| 142 | C | 1014 | C | 982 |
| 143 | B | 1489 | A | 1199 |
| 144 | C | 1492 | C | 296 |
| 145 | B | 1250 | B | 876 |
| 146 | C | 1285 | B | 540 |
| 147 | B | 1620 | A | 1335 |
| 148 | C | 809 | C | 233 |
| 149 | B | 573 | B | 124 |
| 150 | C | 1009 | B | 1085 |
| 151 | A | 6283 | A | 1130 |
| 152 | A | 2326 | A | 1365 |
| 153 | C | 1287 | B | 457 |
| 154 | B | 1541 | B | 1352 |
| 155 | C | 1721 | B | 1634 |
| 156 | B | 1796 | A | 1202 |
| 157 | B | 1358 | A | 838 |
| 158 | B | 2135 | A | 1220 |
| 159 | B | 2642 | A | 1060 |
| 160 | B | 1731 | B | 848 |
| 161 | B | 2639 | A | 1172 |
| 162 | A | 1343 | A | 946 |
| 163 | C | 0 | B | 0 |
| 164 | B | 2213 | B | 1430 |
| 165 | B | 1718 | C | 259 |
| 166 | C | 521 | C | 84 |
| 167 | C | 864 | C | 140 |
| 168 | A | 5569 | A | 1380 |
| 169 | C | 716 | C | 120 |
| 170 | C | 2155 | C | 342 |
| 171 | B | 1611 | B | 765 |

TABLE 2-continued

HDAC1 and HDAC2 $K_d$ Values
for Exemplary Compounds Useful in the Invention

| Compound No. | HDAC2 $K_d$ (uM) | HDAC2 residence time (min) | HDAC1 $K_d$ (uM) | HDAC1 residence time (min) |
|---|---|---|---|---|
| 172 | B | 987.1 | B | 299 |
| 173 | B | 1252 | A | 1210 |
| 174 | A | 1940 | A | 1350 |
| 175 | A | 2710 | A | 1170 |

Morris Water Maze Task

The compounds described herein (e.g., compounds according to Formula (I) or any one of Compounds 100-175) can be examined for its efficacy in the model behavior paradigm, the Morris water maze task as described below:

The water maze task was originally designed by Morris et al. (J Neurosci Methods. 1984; 11: 47-60). Testing is performed in a large dark-colored tank (200 cm in diameter) filled with clear water at a temperature of 25.0±1.0° C. A submerged platform (square platform: 10×10 cm; 1.5 cm below water surface) is placed in the middle of the of the NW quadrant. The starting locations, which are labeled N, NE, E, SE, S, SW, W, NW, are located arbitrarily on the pool rim. The rats are lowered into the pool with their nose pointing toward the wall at one of the starting points. The release point adjacent to platform location (NW) is not used.

At first, before the compound treatment is started, the visible platform pre-training is performed to determine whether any non-cognitive performance impairments (e.g. visual impairments and/or swimming difficulties) are present, which might affect performance on the place or probe trials. All rats receive 4 trials in one day with inter-trial interval of 15 min. On each trial, rats are placed in a fixed position in the swimming pool facing the wall and are allowed to swim to a platform with a rod (cue) 20 cm above water level randomly placed in middle of the pool. They are allowed 60 s to find the platform, which they stay on for 15 s before being removed from the pool. If a rat does not find the platform within 60 s, the rat will be gently guided to the platform and allowed to remain there for 15 s. The time for each rat to reach the cued platform, distance swam, thigmotaxis, and the swim speed are recorded. After the visible platform pre-training is completed, the data is analyzed and the rats are assigned to the different treatment groups based on their pre-training performance. This procedure is performed to ensure that each treatment group consist equally both good and poor performers in the cued version of the water maze task.

Acquisition training—week 1: After completion of cued trials, acquisition (place) trials are executed to determine the rat's ability to learn the spatial relationship between distant cues and the escape platform (submerged, no cue rod), which remain in the same location for all place trials. The starting points are randomized (NW is not used). The rats receive four trials (15 min apart, 60 s maximum for each trial) each day for 4 days. Latency, path length, thigmotaxis and swim speed are recorded.

Acquisition training—week 2: A second set of acquisition trials is executed to determine the rat's ability to learn the spatial relationship between distant cues and the escape platform (submerged, no cue rod), which remain in the same location for all place trials. The starting points are randomized (NW is not used). The rats receive four trials (15 min apart, 60 s maximum for each trial) each day for 4 days. Latency, path length, thigmotaxis and swim speed are recorded.

Probe trial: A single probe trial is conducted 24 hours after the last place trials to evaluate memory retention capabilities. The platform is removed from the water maze and rat is started to swim in the quadrant opposite to one the platform was placed before. The rats are allowed to swim for 60 s during the probe trial. During the probe trial, the time spent in target quadrant and target platform annulus (36-cm-diameter circular area surrounding platform), and crosses over the target platform position are measured (memory retention).

After completing the behavioral tests, the rats are sacrificed and tissue collected for further analysis. Blood was collected and processed to peripheral mononuclear cells and plasma. The cells can be further assayed for acetylation marks to demonstrate that compounds were inhibiting HDAC2 activity. The plasma can be frozen and later assayed by mass spectrometry for the presence of compound. Brain can be collected, dissected into cerebellum and hippocampus. Cerebellum can be frozen and later homogenized and the compound can be extracted and measured by mass spectrometry.

Hippocampal brain tissue can be processed to extract RNA for gene expression analysis. Tissue can be washed with phosphate buffered saline (PBS). RNA can be isolated using the RNeasy isolation kit (Qiagen) according to manufacturer's instructions. The RNA is eluted in 30 μl RNAse free water. The concentration of the isolated RNA can be measured by nanodrop. The RNA can be converted into cDNA with the iScript kit (Biorad) according to manufacturer's instructions. 800 ng of RNA was used per sample. After cDNA synthesis the DNA was diluted 1:5 with milliQ water. Quantitative PCR was done with the SSo advanced supermix (Biorad). Reactions can be done in a white 96-well plate, each reaction contained 1 μl template, 0.75 μl primer mix (forward & reverse, both at 10 μM), 5.75 μl water and 7.5 μL SSo SYBR green advanced supermix. Detection can be done with a CFX Connect Instrument (Biorad). Gene-specific primers for the following genes can be used in these studies: GAPDH—glyceraldehyde-3-phosphate dehydrogenase: BDNF—Brain Derived Neurotrophic Factor: GRIN2A and GRIN2B Glutamate receptor N-methyl D-aspartate-associated proteins 1 & 2: CDK5—cyclin-dependent kinase 5: HOMER1: GRIA1 and GRIA2—glutamate receptor, AMPA 1 & 2: EGR1—early growth response 1: NEFL—neurofilament, light polypeptide: SYT1—Synaptotagmin 1: SYP—synaptophysin. Values can be normalized to expression levels of GAPDH. Three replicates of each sample can be run in each assay and the mean of the replicates can be compared for statistical significant changes.

Peripheral blood mononuclear cells can be isolated using a Ficoll-Paque Plus (GE Healthcare) and can be tested for acetylation marks following treatment with HDCA2 inhibitors. Blood cells can be lysed and proteins can be extracted using 13 RIPA buffer containing proteinase (complete, Roche) and phosphatase inhibitors (1 mMb-glycerophosphate, 10 mM NaF, 0.1 mM Na3VO4) and then can be transferred onto PVDF membranes (Biorad) and stripped using stripping buffer (Thermo Scientific). The following primary antibodies can be used: acetyl-K (Cell Signaling) and actin (Sigma). Secondary antibodies were horseradish peroxidase-linked (GE Healthcare). Signal intensities can be quantified using Image J 1.42q and normalized to values of actin.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:
1. A compound of Formula I:

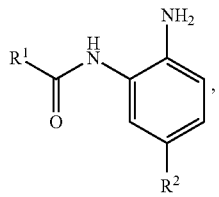

or a pharmaceutically acceptable salt thereof, wherein:
R¹ is an optionally substituted, bicyclic fused, spirofused or bridged, non-aromatic heterocyclyl, comprising at least two heteroatoms independently selected from N, O and S, wherein each ring of R¹ comprises at least one of the heteroatoms; and
R² is selected from heteroaryl and para-substituted aryl, wherein R² is optionally further substituted, and R² is other than optionally substituted biphenyl and optionally substituted thiophenyl;
wherein 1) the optional substituents for said heterocyclyl of R¹, biphenyl, and thiophenyl, 2) the optional further substituents for R², and 3) the substituents for said para-substituted aryl are independently selected from -halo, —NO₂, —CN, —R⁺, —C(R⁺)=C(R⁺)₂, —C≡C—R⁺, —OR⁺, —SR°, —S(O)R°, —SO₂R°, —SO₃, R⁺, —SO₂N(R⁺)₂, —N(R⁺)₂, —NR⁺C(O)R⁺, —NR⁺C(S)R⁺, —NR⁺C(O)N(R⁺)₂, —NR⁺C(S)N(R⁺)₂, —N(R⁺)C(=NR⁺)—N(R⁺)₂, —N(R⁺)C(=NR⁺)—R°, —NR⁺CO₂R⁺, —NR⁺SO₂R°, —NR⁺SO₂N(R⁺)₂, —O—C(O)R⁺, —O—CO₂R⁺, —OC(O)N(R⁺)₂, —C(O)R⁺, —C(S)R°, —CO₂R⁺, —C(O)—C(O)R⁺, —C(O)N(R⁺)₂, —C(S)N(R⁺)₂, —C(O)N(R⁺)—OR⁺, —C(O)N(R⁺)C(=NR⁺)—N(R⁺)₂, —N(R⁺)C(=NR⁺)—N(R⁺)—C(O)R⁺, —C(=NR⁺)—N(R⁺)₂, —C(=NR⁺)—OR⁺, —N(R⁺)—N(R⁺)₂, —C(=NR⁺)—N(R⁺)—OR⁺, —C(R°)=N—OR⁺, —P(O)(R⁺)₂, —P(O)(OR⁺)₂, —O—P(O)—OR⁺, and —P(O)(NR⁺)—N(R⁺)₂;
R⁺, independently, is hydrogen or an aliphatic, aryl, heteroaryl, cycloaliphatic, or heterocyclyl group, or two independent occurrences of R⁺ that are bound to the same atom are taken together with their intervening atom(s) to form a 5-7-membered aryl, heteroaryl, cycloaliphatic, or heterocyclyl ring; and
each R° is an aliphatic, aryl, heteroaryl, cycloaliphatic, or heterocyclyl group;
wherein the compound is other than

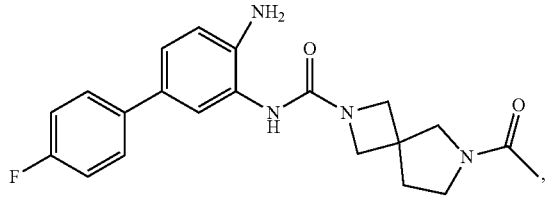

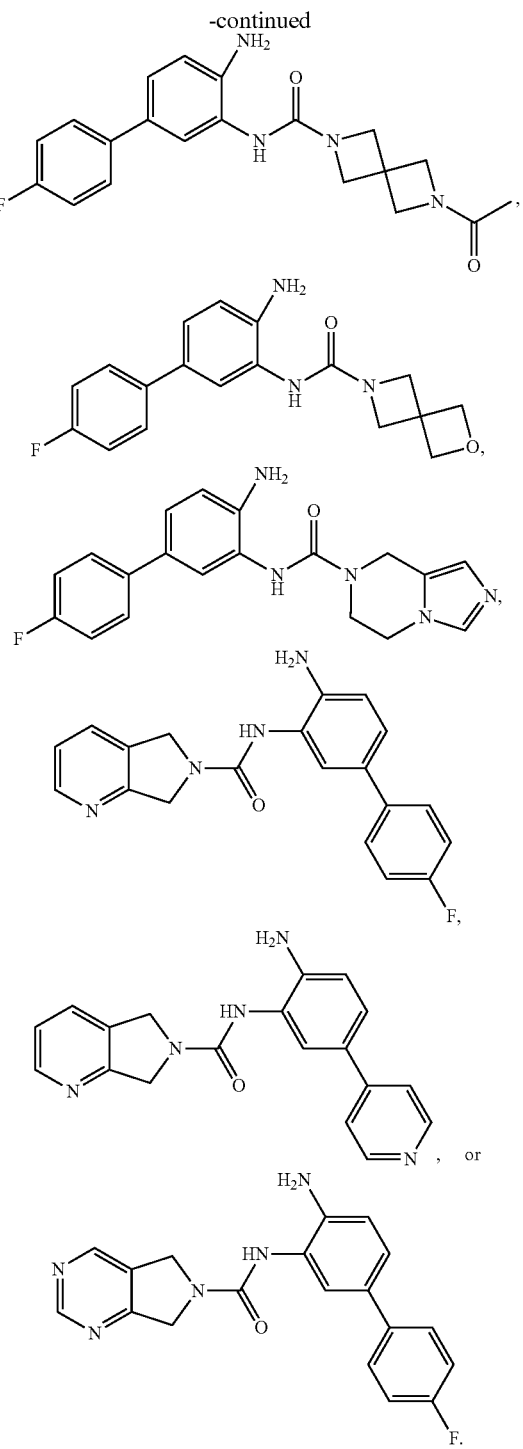

2. The compound of claim 1, wherein R¹ is selected from:
6,7-dihydrothiazolo[5,4-c]pyridin-2-yl,
4,5,6,7-tetrahydrothiazolo[4,5-c]pyridin-2-yl,
4,5,6,7-tetrahydrothiazolo[5,4-c]pyridin-2-yl,
2-oxa-8-azaspiro[4.5]decan-8-yl,
1,3-dihydro-2H-pyrrolo[3,4-c]pyridin-2-yl,
2,8-diazaspiro[4.5]decan-8-yl,
2,8-diazaspiro[4.5]decan-2-yl,
hexahydropyrrolo[3,4-c]pyrrol-2(1H)-yl,
5,6,7,8-tetrahydroimidazo[1,2-a]pyrazin-2-yl,
5,6,7,8-tetrahydroimidazo[1,2-a]pyridin-2-yl, 2-oxa-7-azaspiro[3.5]nonan-7-yl,
5,7-dihydro-6H-pyrrolo[3,4-b]pyrazin-6-yl,
octahydro-5H-pyrrolo[3,4-c]pyridin-5-yl,
5-oxa-2-azaspiro[3.5]nonan-2-yl,
5,7-dihydro-6H-pyrrolo[3,4-d]pyrimidin-6-yl,
8-oxa-2-azaspiro[4.5]decan-2-yl,
7-oxa-2-azaspiro[3.5]nonan-2-yl,
2,7-diazaspiro[3.5]nonan-2-yl,
2,7-diazaspiro[3.5]nonan-7-yl,
2,7-diazaspiro[4.4]nonan-2-yl
octahydro-2H-pyrrolo[3,4-c]pyridin-2-yl,
3,8-diazabicyclo[3.2.1]octan-3-yl,
3,8-diazabicyclo[3.2.1]octan-8-yl,
3,8-diazabicyclo[3.2.1]octan-8-yl,
2,5-diazabicyclo[2.2.1]heptan-2-yl,
8-oxa-3-azabicyclo[3.2.1]octan-3-yl,
5,6,7,8-tetrahydro-4H-thiazolo[4,5-d]azepin-2-yl,
6,7-dihydro-4H-pyrano[4,3-d]thiazol-2-yl,
5,7-dihydro-6H-pyrrolo[3,4-b]pyridin-6-yl,
2-oxa-6-azaspiro[3.4]octan-6-yl,
2-oxa-6-azaspiro[3.3]heptan-6-yl, and
2,6-diazaspiro[3.4]octan-6-yl, wherein $R^1$ is optionally substituted with up to 4 independently selected substituents.

3. The compound of claim 2, wherein $R^1$ is selected from:

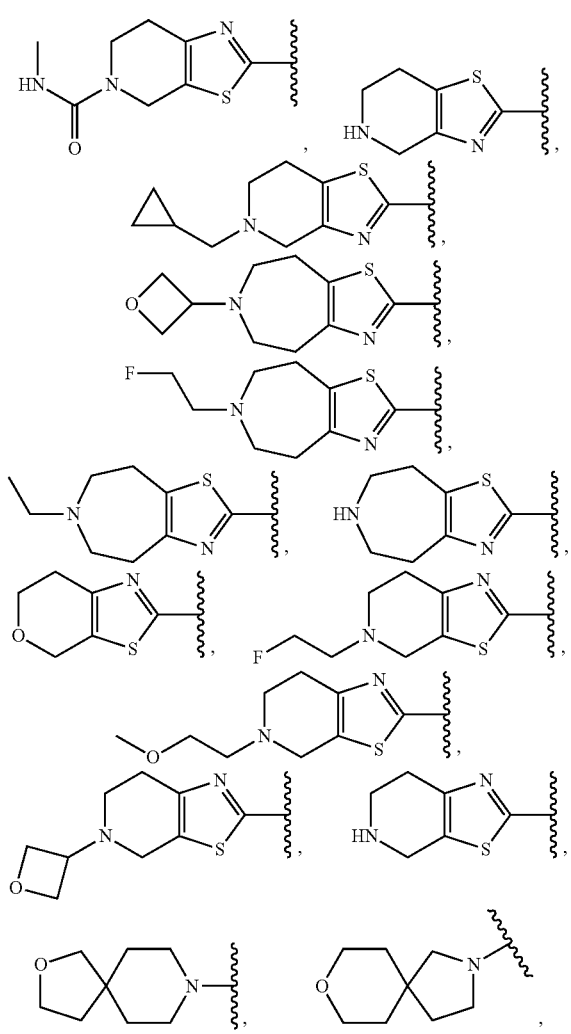

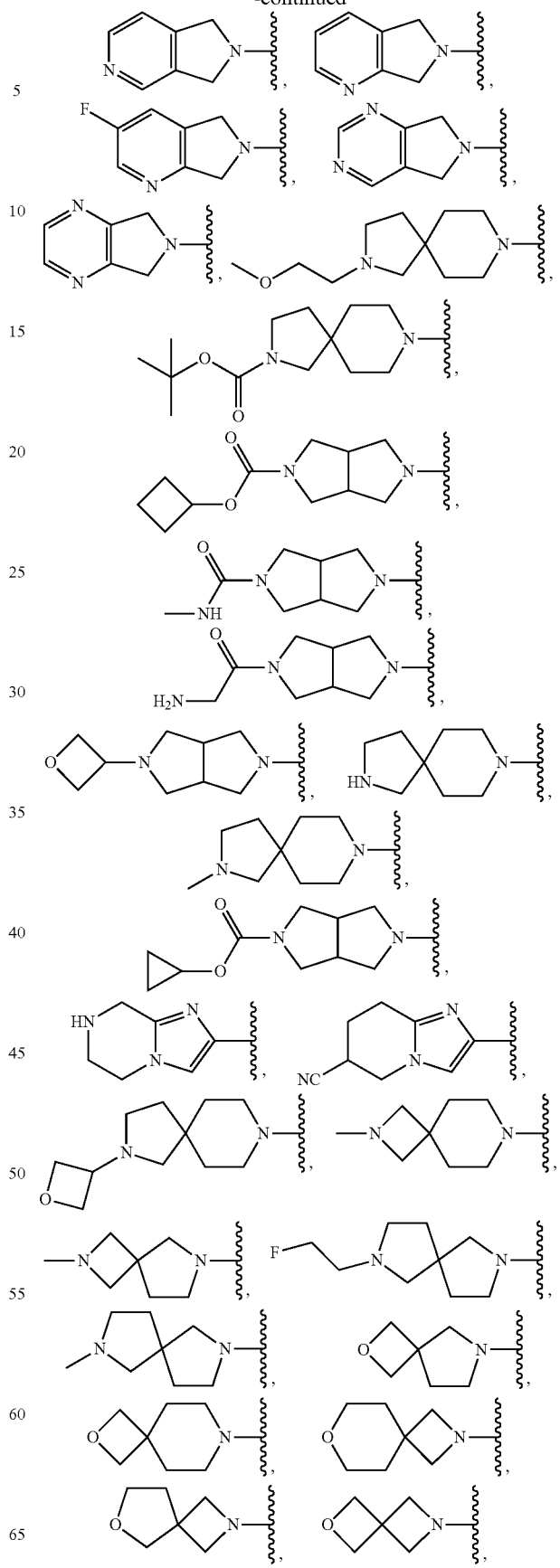

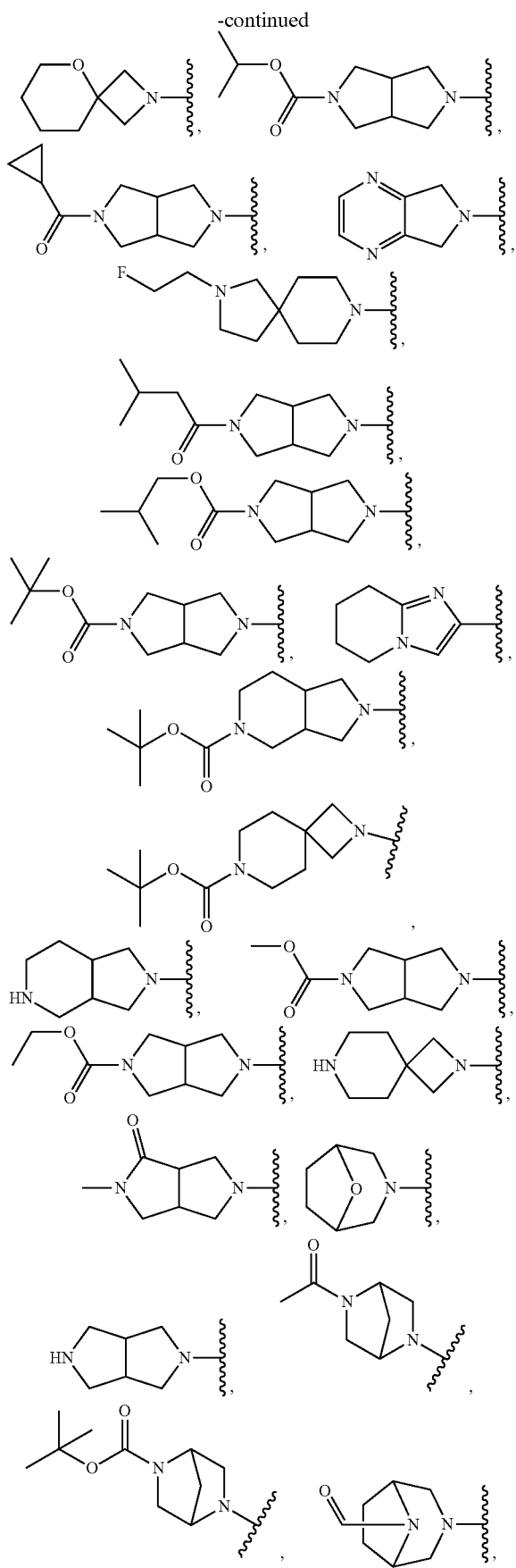
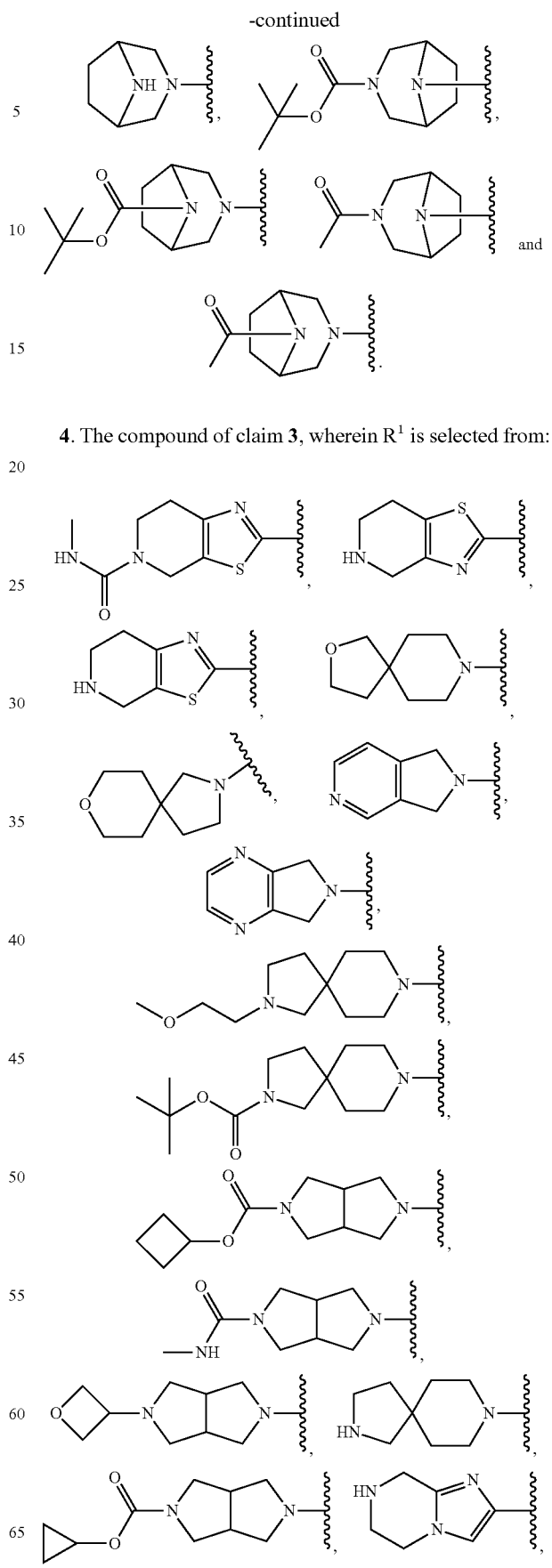
4. The compound of claim 3, wherein $R^1$ is selected from:

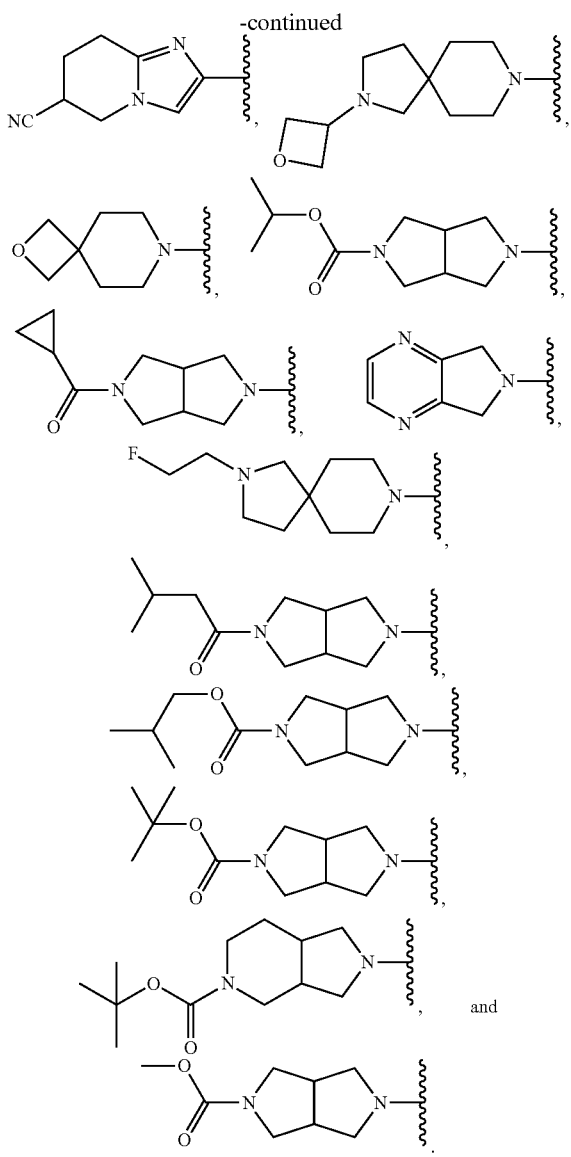

5. The compound of claim 4, wherein $R^1$ is selected from:

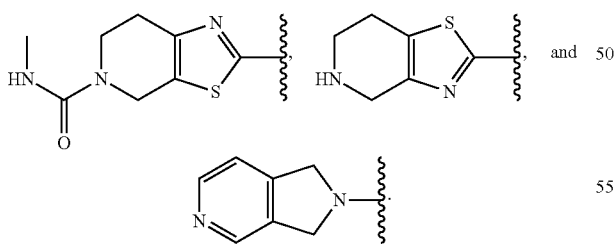

6. The compound of claim 5, wherein $R^2$ is selected from para-substituted phenyl, pyridinyl, furanyl, 1H-Pyrazolyl, thiazolyl, isoxazolyl, oxazolyl, isothiazolyl, 5,6-dihydro-4H-Pyrrolol[1,2-b]pyrazolyl, pyridazinyl, and pyrimidinyl, and wherein $R^2$ is optionally additionally substituted.

7. The compound of claim 6, wherein $R^2$ is selected from 4-fluorophenyl, 4-methoxyphenyl, 4-chlorophenyl, 4-difluromethoxyphenyl, 4-cyanophenyl, 4-trifluoromethylphenyl, 2,4-difluorophenyl, 3,4-difluorophenyl, 3-chloro-4-fluorophenyl, 3,4,5-trifluorophenyl, 2-fluoro-4-trifluoromethylphenyl, 2-methyl-4-fluorophenyl, pyridin-2-yl, pyridin-3-yl, pyridin-4-yl, 5-trifluoromethylpyridin-2-yl, 6-methoxypyridin-3-yl, 6-methylpyridin-3-yl, 6-fluoropyridin-3-yl, 2-methylpyridin-4-yl, 2-fluoropyridin-4-yl, furan-2-yl, 5-methylfuran-2-yl, 5-chlorofuran-2-yl, furan-3-yl, 5-methylfuran-3-yl, 5-chlorofuran-3-yl, 1H-pyrazol-4-yl, 1-ethyl-1H-Pyrazol-4-yl, 1-methyl-1H-Pyrazol-4-yl, 1-cyclobutyl-1H-pyrazol-4-yl, 1,5-dimethyl-1H-pyrazol-4-yl, 2-methylthiazol-5-yl, 3-methylisoxazol-5-yl, 2-methyloxazoly-5-yl, 3-methylisothiazol-5-yl, 5,6-dihydro-4H-Pyrrolol[1,2-b]pyrazol-3-yl, 6-methylpyridazin-4-yl, 6-methylpyridazin-3-yl, and pyrimidin-3-yl.

8. The compound of claim 7, wherein $R^2$ is selected from 4-fluorophenyl, 4-methoxyphenyl, 4-chlorophenyl, 4-difluromethoxyphenyl, 4-cyanophenyl, 2,4-difluorophenyl, 3,4-difluorophenyl, pyridin-3-yl, pyridin-4-yl, furan-2-yl, furan-3-yl, and 1-methyl-1H-Pyrazol-4-yl.

9. The compound of claim 8, wherein $R^2$ is selected from 4-fluorophenyl, 4-methoxyphenyl, 4-difluromethoxyphenyl, pyridin-4-yl, furan-2-yl, and furan-3-yl.

10. The compound of claim 1, wherein the compound is selected from:

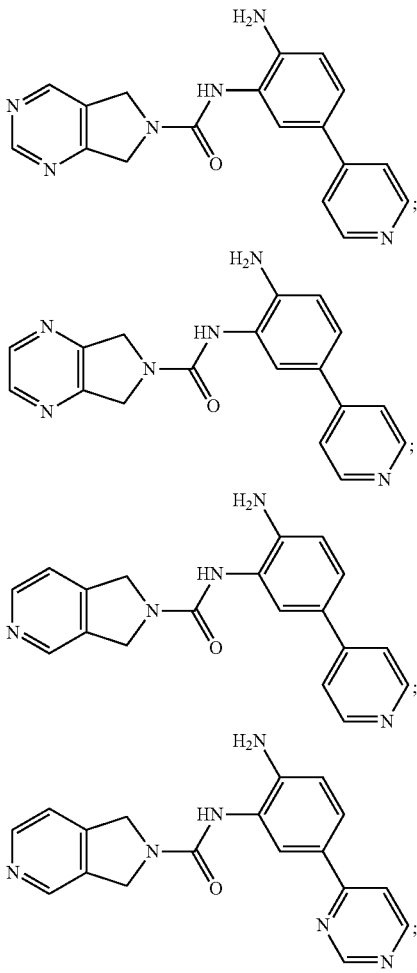

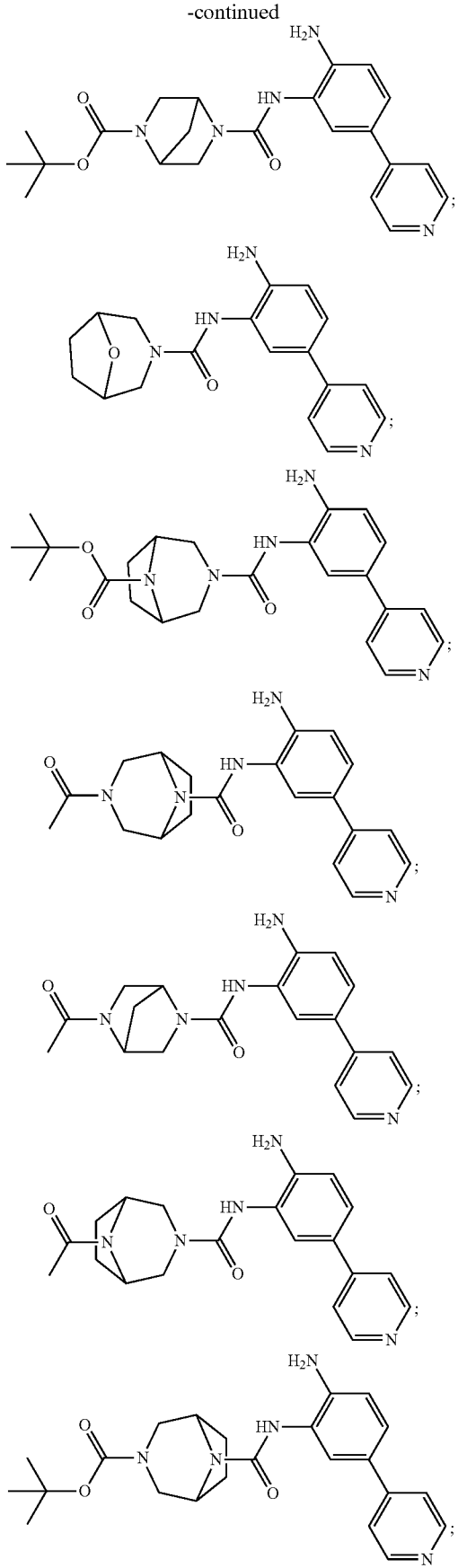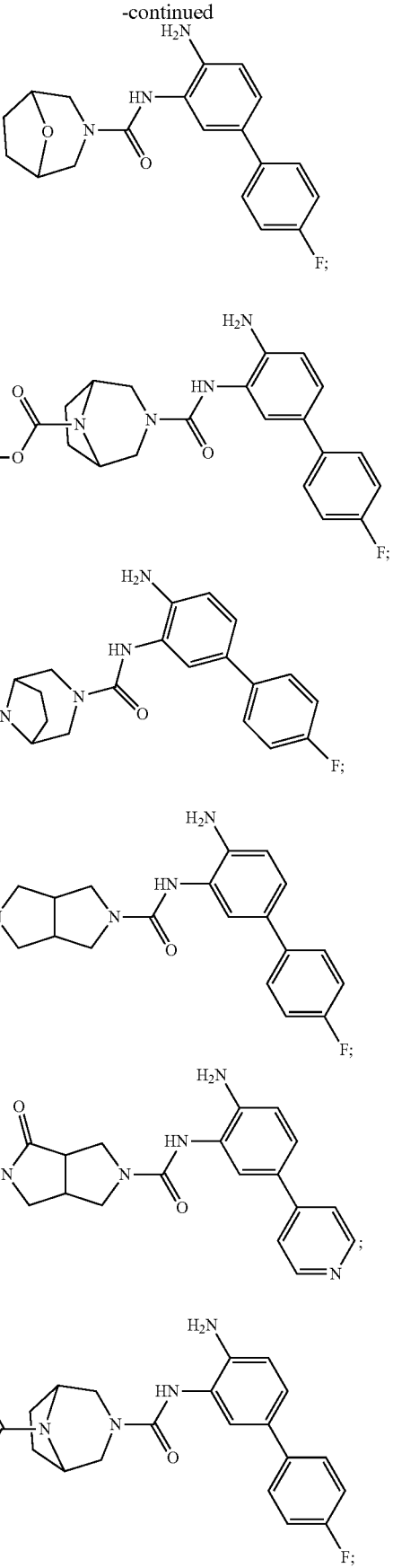

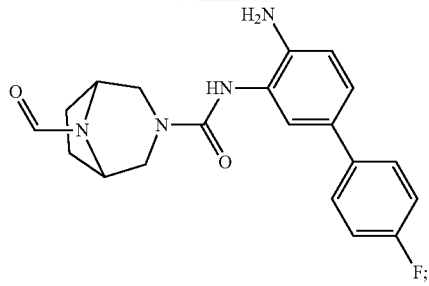
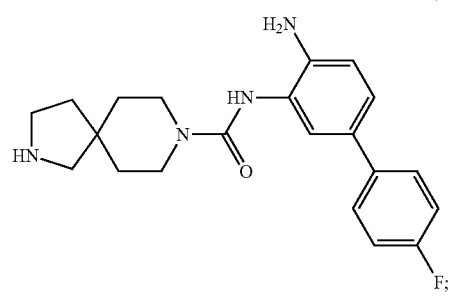
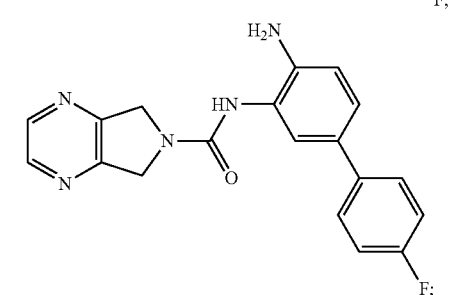
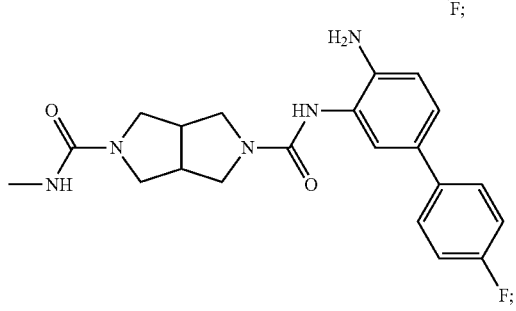
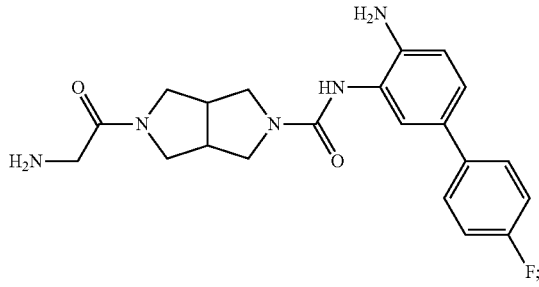
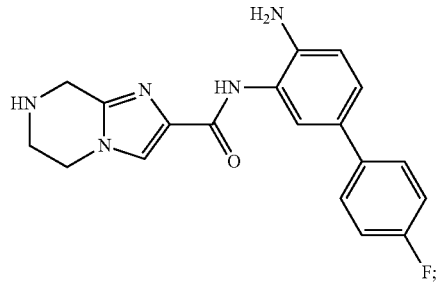
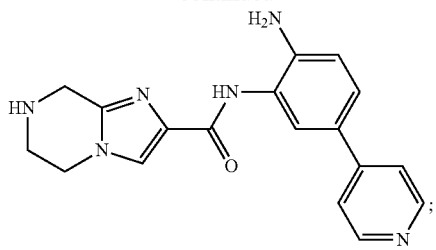
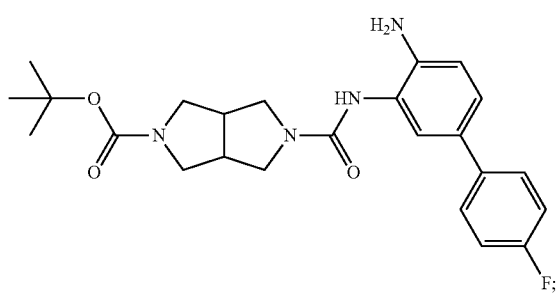
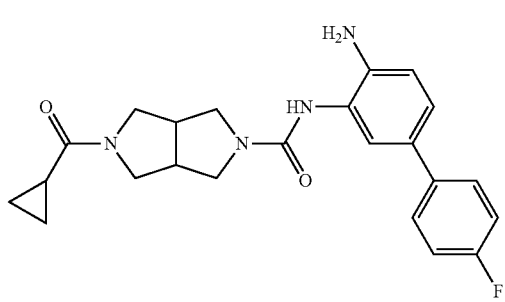
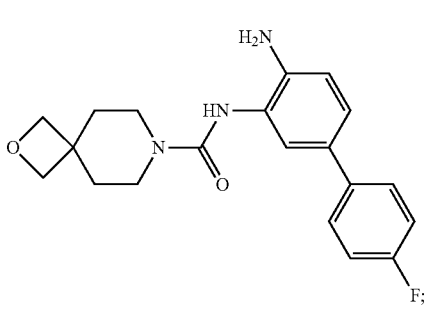
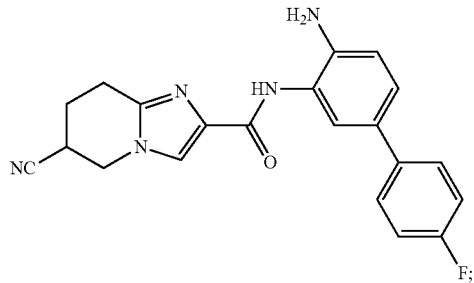
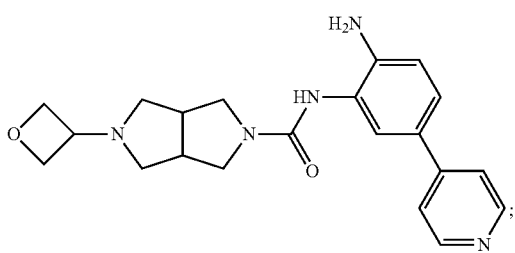

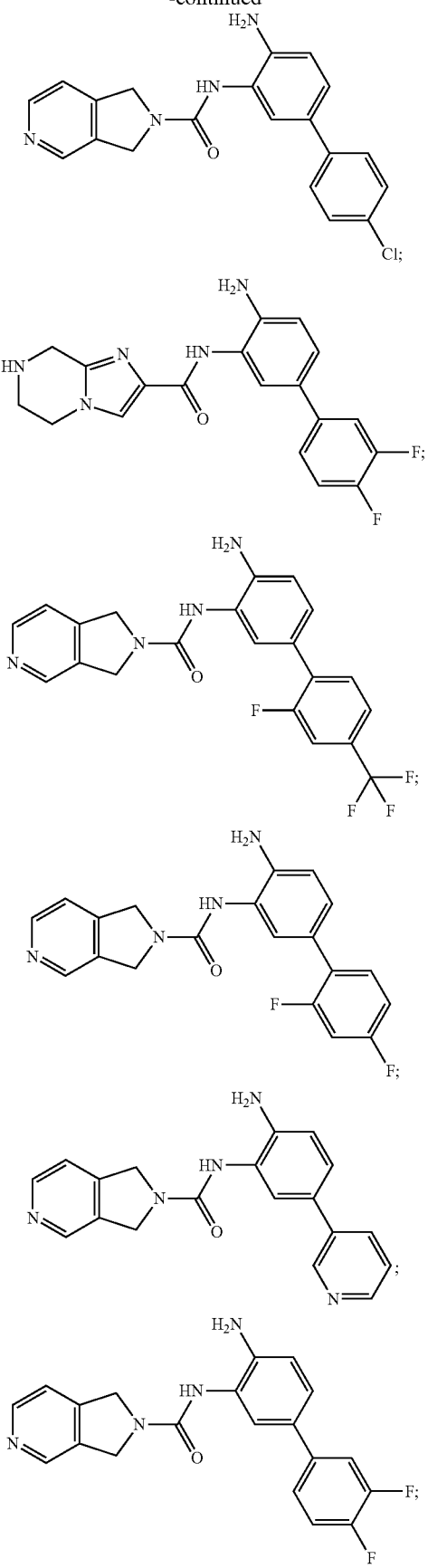
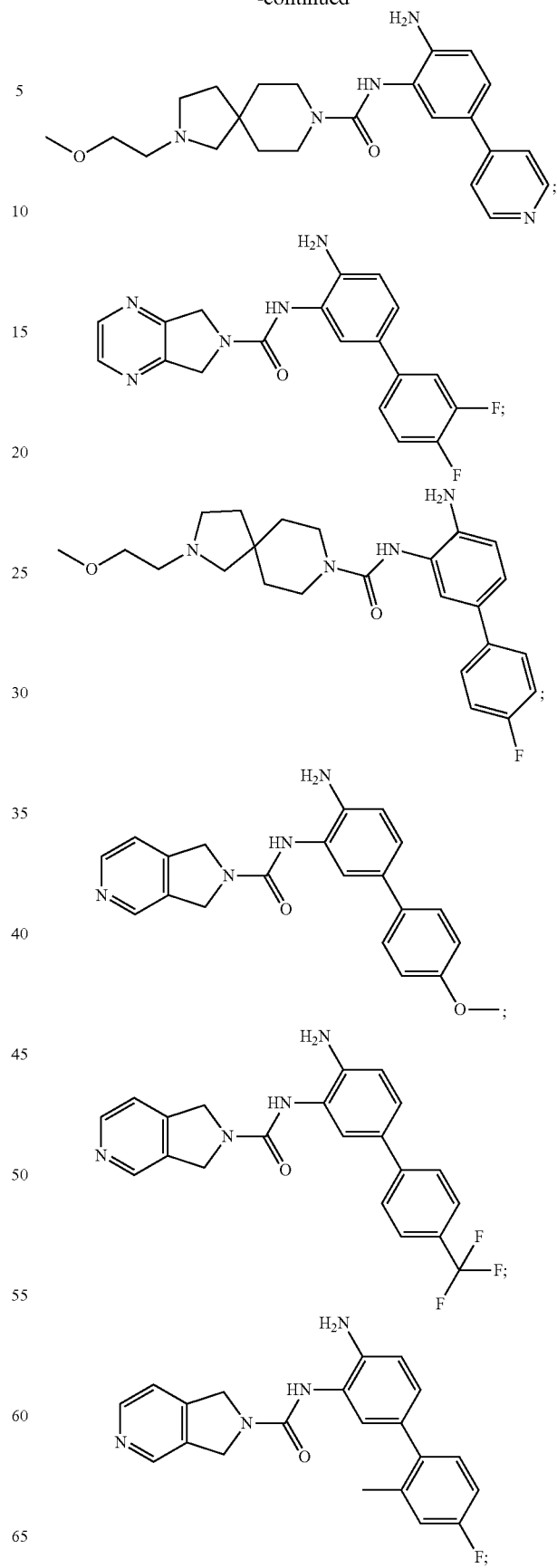

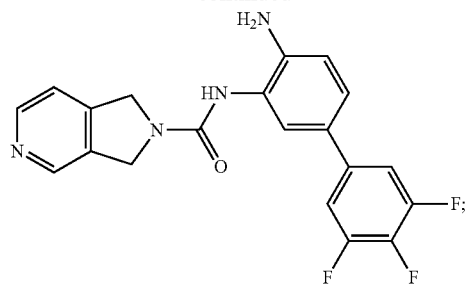
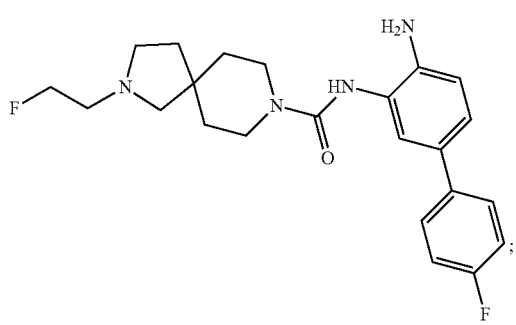
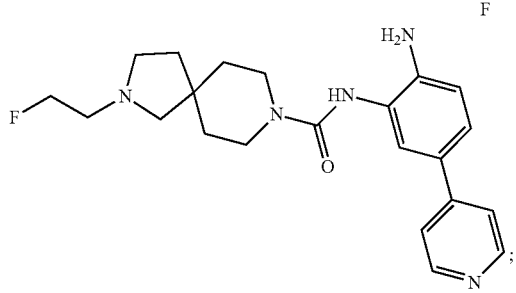
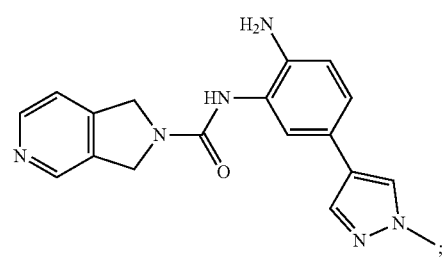
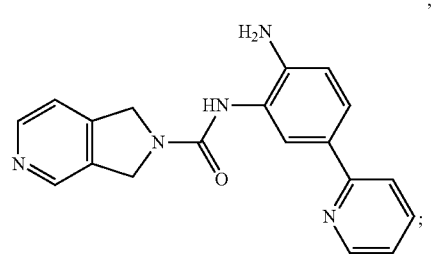
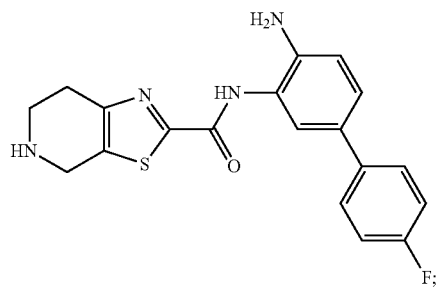
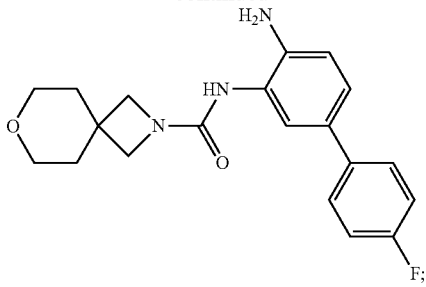
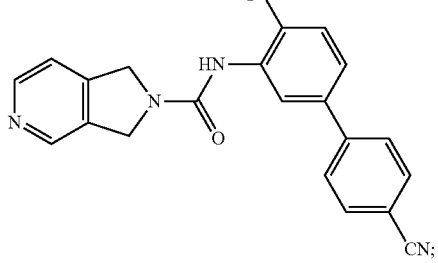
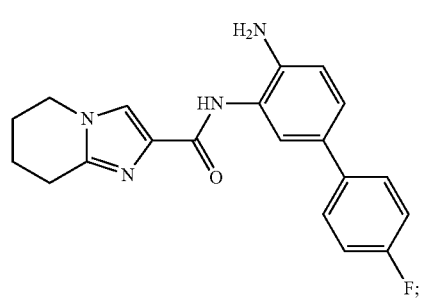
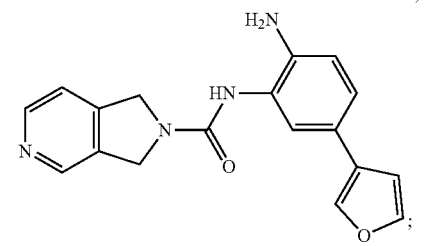
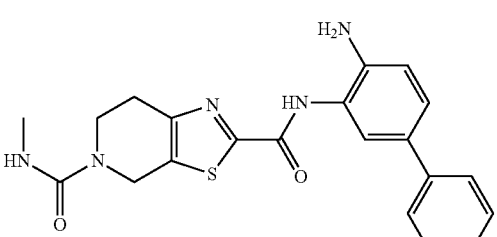
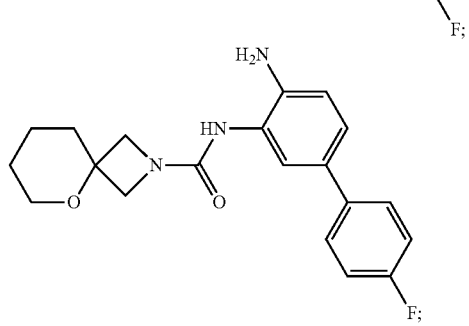

-continued

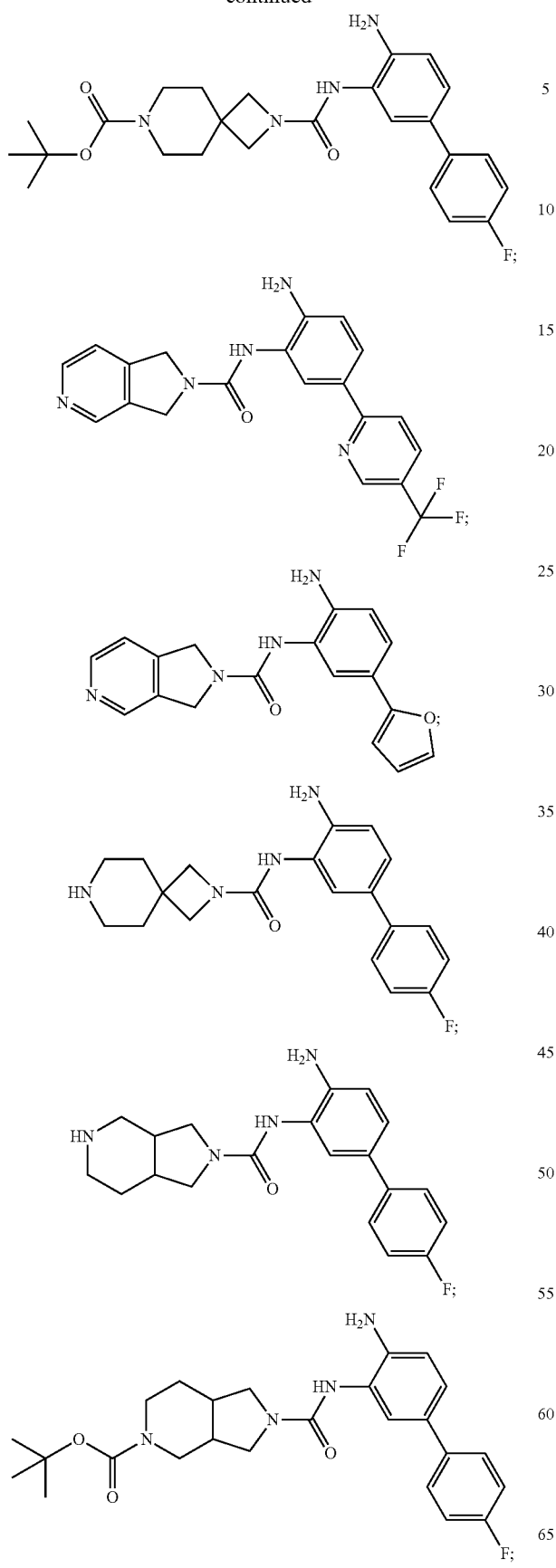

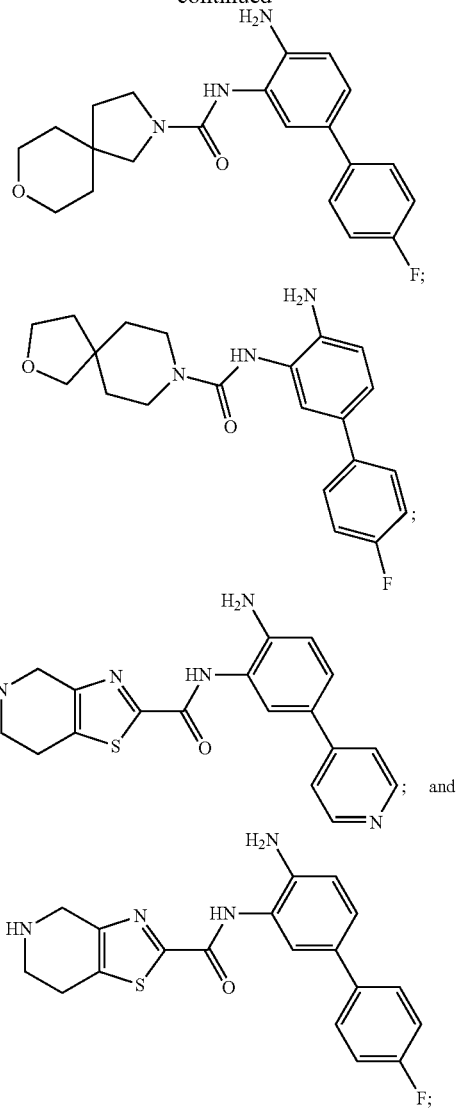

or a pharmaceutically acceptable salt thereof.

11. A pharmaceutical composition comprising a compound of claim 1 or a pharmaceutically acceptable salt thereof; and a pharmaceutically acceptable carrier.

12. A method of treating a condition in a subject selected from
a. a cognitive function disorder or impairment associated with Alzheimer's disease, Huntington's disease, seizure induced memory loss, schizophrenia, Rubinstein Taybi syndrome, Rett Syndrome, Fragile X, Lewy body dementia, vascular dementia, frontotemporal dementia, ADHD, dyslexia, bipolar disorder and social, cognitive and learning disorders associated with autism, traumatic head injury, attention deficit disorder, anxiety disorder, conditioned fear response, panic disorder, obsessive compulsive disorder, posttraumatic stress disorder (PTSD), phobia, social anxiety disorder, substance dependence recovery, Age Associated Memory Impairment (AAMI), Age Related Cognitive Decline (ARCD), ataxia, or Parkinson's disease;
b. a hematological disease selected from acute myeloid leukemia, acute promyelocytic leukemia, acute lymphoblastic leukemia, chronic myelogenous leukemia, myelodysplastic syndromes, and sickle cell anemia;
c. a neoplastic disease; and
d. an extinction learning disorder selected from fear extinction and post-traumatic stress disorder, comprising administering to the subject in need thereof an effective amount of a compound of claim 1, or a pharmaceutically acceptable salt thereof.

13. The method of claim 12, wherein the condition is Alzheimer's disease, Huntington's disease, frontotemporal dementia, Freidreich's ataxia, post-traumatic stress disorder (PTSD), Parkinson's disease, or substance dependence recovery.

* * * * *

UNITED STATES PATENT AND TRADEMARK OFFICE
CERTIFICATE OF CORRECTION

PATENT NO. : 10,421,756 B2
APPLICATION NO. : 15/741609
DATED : September 24, 2019
INVENTOR(S) : Martin R. Jefson et al.

Page 1 of 1

It is certified that error appears in the above-identified patent and that said Letters Patent is hereby corrected as shown below:

In the Claims

Column 85, Claim 1, Line 35, please replace "-SO$_3$, R$^+$" with -- -SO$_3$R$^+$--;
        Line 50, please replace "R$^+$that" with --R$^+$ that--.

Column 87, Claim 2, Lines 13-16, please replace "3,8-diazabicyclo[3.2.1]octan-3-yl, 3,8-diazabicyclo[3.2.1]octan-8-yl, 3,8-diazabicyclo[3.2.1]octan-8-yl, 2,5-diazabicyclo[2.2.1]heptan-2-yl," with --3,8-diazabicyclo[3.2.1]octan-3-yl, 3,8-diazabicyclo[3.2.1]octan-8-yl, 2,5-diazabicyclo[2.2.1]heptan-2-yl,--.

Column 91, Claim 6, Lines 63-64, please replace "5,6-dihydro-4H-Pyrrolol[1,2-b]pyrazolyl" with --5,6-dihydro-4H-pyrrolo[1,2-b]pyrazolyl--.

Column 92, Claim 7, Lines 14-15, please replace "5,6-dihydro-4H-Pyrrolol[1,2-b]pyrazol-3-yl" with --5,6-dihydro-4H-pyrrolo[1,2-b]pyrazol-3-yl--.

Signed and Sealed this
Fourteenth Day of April, 2020

Andrei Iancu
*Director of the United States Patent and Trademark Office*